(12) United States Patent
Blanchard

(10) Patent No.: US 12,098,358 B2
(45) Date of Patent: Sep. 24, 2024

(54) AUTOMATED INCUBATOR WITH ROBOTIC TRANSPORT

(71) Applicant: Thrive Bioscience, Inc., Beverly, MA (US)

(72) Inventor: Alan Blanchard, Topsfield, MA (US)

(73) Assignee: Thrive Bioscience, Inc., Beverly, MA (US)

( * ) Notice: Subject to any disclaimer, the term of this patent is extended or adjusted under 35 U.S.C. 154(b) by 780 days.

(21) Appl. No.: 17/225,944

(22) Filed: Apr. 8, 2021

(65) Prior Publication Data

US 2021/0222110 A1    Jul. 22, 2021

Related U.S. Application Data

(63) Continuation-in-part of application No. 15/931,927, filed on May 14, 2020, now Pat. No. 11,332,705.
(Continued)

(51) Int. Cl.
*C12M 1/00* (2006.01)
*C12M 1/34* (2006.01)
(Continued)

(52) U.S. Cl.
CPC ............ *C12M 41/14* (2013.01); *C12M 41/36* (2013.01); *C12M 41/40* (2013.01); *C12M 41/48* (2013.01);
(Continued)

(58) Field of Classification Search
CPC ...... C12M 41/14; C12M 41/36; C12M 41/40; C12M 41/48; G01N 15/1433;
(Continued)

(56) References Cited

U.S. PATENT DOCUMENTS

| | | |
|---|---|---|
| 3,887,436 A | 6/1975 | Haddad et al. |
| 4,871,676 A | 10/1989 | Yamada |

(Continued)

FOREIGN PATENT DOCUMENTS

| | | |
|---|---|---|
| CN | 101313196 A | 11/2008 |
| CN | 101501180 A | 8/2009 |

(Continued)

OTHER PUBLICATIONS

International Search Report and Written Opinion mailed Jun. 29, 2022, for Application No. PCT/US2022/023876.
(Continued)

*Primary Examiner* — Michael L Hobbs
(74) *Attorney, Agent, or Firm* — Wolf, Greenfield & Sacks, P.C.

(57) ABSTRACT

A cell incubator system comprising a housing having an internal chamber having a controlled temperature and gas mixture therein appropriate for the growth of particular cells for incubation of the particular cells in one or more cell culture vessels in the internal chamber and a plurality of cell operation stations in the internal chamber. The stations receive plates having wells for holding cells and wherein the cell operations stations perform operations on cells in the wells. The system has a robotic transport for moving plates from one station to another.

11 Claims, 26 Drawing Sheets

Related U.S. Application Data which is a continuation of application No. 15/563,383, filed as application No. PCT/US2016/025356 on Mar. 31, 2016, now Pat. No. 10,696,937, and a continuation-in-part of application No. 15/563,360, filed as application No. PCT/US2016/025362 on Mar. 31, 2016, now Pat. No. 11,168,297, and a continuation-in-part of application No. 15/563,375, filed as application No. PCT/US2016/025349 on Mar. 31, 2016, now Pat. No. 11,034,927, and a continuation-in-part of application No. 15/563,370, filed as application No. PCT/US2016/025339 on Mar. 31, 2016, now Pat. No. 11,319,523.

(60) Provisional application No. 62/141,196, filed on Mar. 31, 2015, provisional application No. 62/141,183, filed on Mar. 31, 2015, provisional application No. 62/141,191, filed on Mar. 31, 2015, provisional application No. 62/141,187, filed on Mar. 31, 2015.

(51) Int. Cl.

| | | |
|---|---|---|
| *C12M 1/36* | (2006.01) | |
| *G01N 15/1433* | (2024.01) | |
| *G01N 35/00* | (2006.01) | |
| *G01N 15/10* | (2006.01) | |
| *G01N 15/1434* | (2024.01) | |
| *G01N 35/04* | (2006.01) | |

(52) U.S. Cl.
CPC ... G01N 15/1433 (2024.01); G01N 35/00732 (2013.01); G01N 35/0099 (2013.01); *G01N 2015/1006* (2013.01); *G01N 2015/1454* (2013.01); *G01N 2035/00356* (2013.01); *G01N 2035/0463* (2013.01)

(58) Field of Classification Search
CPC ......... G01N 35/00732; G01N 35/0099; G01N 2015/1006; G01N 2015/1454; G01N 2035/00356; G01N 2035/0463
See application file for complete search history.

(56) References Cited

U.S. PATENT DOCUMENTS

| | | | |
|---|---|---|---|
| 5,906,943 A | 5/1999 | Skropik et al. | |
| 5,958,763 A | 9/1999 | Goffe | |
| 6,465,244 B1 | 10/2002 | Annable et al. | |
| 7,540,844 B2 | 6/2009 | Muser | |
| 8,548,745 B2 | 10/2013 | Callahan et al. | |
| 9,857,360 B2 | 1/2018 | Lim | |
| 10,201,896 B2 | 2/2019 | Kihara et al. | |
| 10,696,937 B2 | 6/2020 | Blanchard | |
| 11,034,927 B2 | 6/2021 | Blanchard | |
| 11,168,297 B2 | 11/2021 | Blanchard | |
| 11,319,523 B2 | 5/2022 | Blanchard | |
| 11,332,705 B2 | 5/2022 | Blanchard | |
| 11,879,120 B2 | 1/2024 | Blanchard | |
| 11,920,121 B2 | 3/2024 | Blanchard | |
| 11,920,122 B2 | 3/2024 | Blanchard | |
| 2001/0039032 A1 | 11/2001 | Matsumura et al. | |
| 2002/0090320 A1 | 7/2002 | Burrow et al. | |
| 2002/0146347 A1* | 10/2002 | McNeil | G05D 1/0291 422/65 |
| 2003/0040104 A1 | 2/2003 | Barbera-Guillem | |
| 2004/0029266 A1 | 2/2004 | Barbera-Guillem | |
| 2004/0064013 A1 | 4/2004 | Attias | |
| 2004/0215362 A1 | 10/2004 | Kokubo | |
| 2005/0170491 A1 | 8/2005 | Takagi | |
| 2005/0239040 A1 | 10/2005 | Lindenberg | |
| 2005/0260743 A1 | 11/2005 | Drake et al. | |
| 2006/0177922 A1 | 8/2006 | Shamah et al. | |
| 2006/0194193 A1 | 8/2006 | Tsuruta et al. | |
| 2006/0275888 A1* | 12/2006 | Hibino | C12M 41/14 435/286.2 |
| 2008/0090288 A1 | 4/2008 | Hibino et al. | |
| 2010/0099177 A1 | 4/2010 | Yang et al. | |
| 2010/0291619 A1 | 11/2010 | Robinson et al. | |
| 2010/0330651 A1 | 12/2010 | Venter et al. | |
| 2011/0027146 A1 | 2/2011 | Yokoi et al. | |
| 2012/0092478 A1 | 4/2012 | Honda et al. | |
| 2012/0122138 A1 | 5/2012 | Randles et al. | |
| 2012/0122143 A1 | 5/2012 | Mimura et al. | |
| 2012/0164721 A1 | 6/2012 | Kobayashi et al. | |
| 2012/0196316 A1 | 8/2012 | Sebesta et al. | |
| 2013/0074614 A1 | 3/2013 | Holmes et al. | |
| 2013/0079236 A1 | 3/2013 | Holmes | |
| 2013/0130361 A1 | 5/2013 | Okano et al. | |
| 2013/0210130 A1 | 8/2013 | Larcher et al. | |
| 2013/0273646 A1 | 10/2013 | Kobayashi et al. | |
| 2013/0316442 A1 | 11/2013 | Meurville et al. | |
| 2014/0051156 A1 | 2/2014 | Miyake et al. | |
| 2014/0057342 A1 | 2/2014 | Uozumi et al. | |
| 2014/0106386 A1 | 4/2014 | Umeno et al. | |
| 2014/0106389 A1 | 4/2014 | Loewke et al. | |
| 2014/0273191 A1 | 9/2014 | Tipgunlakant et al. | |
| 2015/0037206 A1 | 2/2015 | Akutsu | |
| 2015/0079584 A1 | 3/2015 | Gevaert et al. | |
| 2015/0079621 A1 | 3/2015 | An et al. | |
| 2015/0278625 A1 | 10/2015 | Finkbeiner et al. | |
| 2015/0298123 A1* | 10/2015 | Block, III | F04B 43/0054 435/284.1 |
| 2015/0322479 A1 | 11/2015 | Pettigrew et al. | |
| 2017/0137770 A1 | 5/2017 | Sakamoto et al. | |
| 2017/0361468 A1 | 12/2017 | Cheuvront et al. | |
| 2018/0066218 A1 | 3/2018 | Koike et al. | |
| 2018/0079999 A1 | 3/2018 | Blanchard | |
| 2018/0087020 A1 | 3/2018 | Blanchard | |
| 2018/0087021 A1 | 3/2018 | Blanchard | |
| 2018/0346868 A1 | 12/2018 | Blanchard | |
| 2020/0347339 A1 | 11/2020 | Blanchard | |
| 2020/0348324 A1 | 11/2020 | Wikholm et al. | |
| 2021/0261903 A1 | 8/2021 | Blanchard | |
| 2022/0243167 A1 | 8/2022 | Blanchard | |
| 2022/0259546 A1 | 8/2022 | Blanchard | |

FOREIGN PATENT DOCUMENTS

| | | |
|---|---|---|
| CN | 101987205 A | 3/2011 |
| CN | 102174395 A | 9/2011 |
| CN | 102321522 A | 1/2012 |
| CN | 102471744 A | 5/2012 |
| CN | 104245917 A | 12/2014 |
| EP | 1 460 126 A2 | 9/2004 |
| EP | 1 471 138 A1 | 10/2004 |
| EP | 1 553 166 A1 | 7/2005 |
| EP | 1 598 415 A1 | 11/2005 |
| EP | 1 650 291 A1 | 4/2006 |
| JP | 58-036383 A | 3/1983 |
| JP | H02-171866 A | 7/1990 |
| JP | 2003-052365 A | 2/2003 |
| JP | 2003-174870 A | 6/2003 |
| JP | 2004-511788 A | 4/2004 |
| JP | 2004-321111 A | 11/2004 |
| JP | 2005-102570 A | 4/2005 |
| JP | 2006-101781 A | 4/2006 |
| JP | 2006-174828 A | 7/2006 |
| JP | 2006-284288 A | 10/2006 |
| JP | 2009-511998 A | 3/2009 |
| JP | 3157029 U | 1/2010 |
| JP | 2010-154792 A | 7/2010 |
| JP | 2010-273603 A | 12/2010 |
| JP | 2011-030655 A | 2/2011 |
| JP | 2012-130297 A | 7/2012 |
| JP | 2012-524268 A | 10/2012 |
| JP | 2013-009618 A | 1/2013 |
| WO | WO 98/24883 A2 | 6/1998 |
| WO | WO 2005/009126 A1 | 2/2005 |
| WO | WO 2011/010449 A1 | 1/2011 |
| WO | WO 2011/089908 A1 | 7/2011 |
| WO | WO 2011/091333 A1 | 7/2011 |
| WO | WO 2013/016248 A1 | 1/2013 |

(56) References Cited

FOREIGN PATENT DOCUMENTS

| WO | WO 2014/044823 A1 | 3/2014 |
|----|-------------------|--------|
| WO | WO 2012/098931 A1 | 6/2014 |
| WO | WO 2015/019595 A1 | 2/2015 |

OTHER PUBLICATIONS

International Preliminary Report on Patentability mailed Oct. 19, 2023, for Application No. PCT/US2022/023876.

[No Author Listed] Incubator Fluorescence Microscope LCV110U VivaView FL. 2008. Brochure by Olympus America. Retrieved from the Internet.<http://www.olympus-lifesience.com/en/microscopes/inverted/incubator/#!cms[tab]=%2Fmicroscopes%2Finverted%2Fincubator%2Fresources>.; p. 5.

[No Author Listed], Digital holographic microscopy, Wikipedia. Archived Feb. 17, 2015. Last accessed Jul. 5, 2023 from <https://web.archive.org/web/20150217070233/https://en.wikipedia.org/wiki_Digital_holographic_microscopy.htm>. 12 pages.

[No Author Listed], Nikon. BioStation IM-Q product webpage. Archived Jan. 19, 2015. Last accessed Nov. 24, 2023 from <https://web.archive.org/web/20150119025735/http://www.nikon.com/products/instruments/lineup/bioscience/time/imq/index.htm>. 11 pages.

Buggenthin et al., An automatic method for robust and fast cell detection in bright field images from high-throughput microscopy. BMC Bioinformatics. Oct. 4, 2013;14:297.

Colomb et al., Advantages of digital holographic microscopy for real-time full field absolute phase imaging. Proceedings of SPIE. Feb. 2008; 6861: 10 pages.

\* cited by examiner

AUTOMATED INCUBATOR WITH ROBOTIC TRANSPORT

RELATED APPLICATIONS

This application is a continuation-in-part application and claims the benefit under 35 U.S.C. § 120 of U.S. application Ser. No. 15/563,370, filed Sep. 29, 2017, now U.S. Pat. No. 11,319,523, which is a National Stage filing under 35 U.S.C. § 371 of International Application No. PCT/US2016/025339, filed Mar. 31, 2016, which claims the benefit under 35 U.S.C. § 119(e) of U.S. Provisional Application Ser. No. 62/141,183, filed Mar. 31, 2015 and entitled "AUTOMATED CELL CULTURE INCUBATOR", the entire contents of each of which are incorporated by reference herein.

This application is also a continuation-in-part application and claims the benefit under 35 U.S.C. § 120 of U.S. application Ser. No. 15/931,927, filed May 14, 2020, now U.S. Pat. No. 11,332,705, which is a continuation application and claims the benefit under U.S.C. § 120 of Ser. No. 15/563,383, filed Sep. 29, 2017, now U.S. Pat. No. 10,696,937, which is a National Stage filing under 35 U.S.C. § 371 of International Application No. PCT/US2016/025356, filed Mar. 31, 2016, which claims the benefit under 35 U.S.C. § 119(e) of U.S. Provisional Application Ser. No. 62/141,191, filed Mar. 31, 2015 and entitled "CELL CULTURE INCUBATORS WITH INTEGRATED CELL MANIPULATION SYSTEMS", the entire contents of each of which are incorporated by reference herein, This application is also a continuation-in-part application and claims the benefit under 35 U.S.C. § 120 of U.S. application Ser. No. 15/563,360, filed Sep. 29, 2017, now U.S. Pat. No. 11,168,297, which is a National Stage filing under 35 U.S.C. § 371 of International Application No. PCT/US2016/025362, filed Mar. 31, 2016, which claims the benefit under 35 U.S.C. § 119(e) of U.S. Provisional Application Ser. No. 62/141,196, filed Mar. 31, 2015 and entitled "CELL MAINTAINER FOR AUTOLOGOUS CELL THERAPY PRODUCTION", the entire contents of each of which are incorporated by reference herein.

This application is also a continuation-in-part application and claims the benefit under U.S.C. § 120 of U.S. application Ser. No. 15/563,375, filed Sep. 29, 2017, now U.S. Pat. No. 11,034,927, which is a National Stage filing under 35 U.S.C. § 371 of International Application No. PCT/US2016/025349, filed Mar. 31, 2016, which claims the benefit under 35 U.S.C. § 119(e) of U.S. Provisional Application Ser. No. 62/141,187, filed Mar. 31, 2015 and entitled "CELL CULTURE INCUBATORS WITH INTEGRATED IMAGING SYSTEMS", the entire contents of each of which are incorporated by reference herein.

FIELD

Aspects relate to cell culture incubators and to methods for using such incubators.

BACKGROUND

Cell culture incubators are used to grow and maintain cells from cell culture, which is the process by which cells are grown under controlled conditions. Cell culture vessels containing cells are stored within the incubator, which maintains conditions such as temperature and gas mixture that are suitable for cell growth. Maintenance of cultures, tissue preparations, in vitro fertilization preparations, etc., in presently available cell incubators is a laborious process requiring highly trained personnel and stringent aseptic conditions. This high level of human involvement can introduce contaminants into the culture and cause shock from environmental changes, thereby lowering culture efficiency. Accordingly, new types of cell culture incubators that provide a culture system with minimal human involvement are needed.

SUMMARY

A cell culture incubator includes a cabinet or a housing having at least one chamber therein. Within the at least one chamber are at least two stations for operations on cells. Operations include, by way of example, storing, manipulating cells, imaging, pipetting fluids into and out of cell media, scraping, mixing, etc. A station for example can be a holding area for cell culture plates. Another station can be an imaging station wherein an imager is provided for taking images of cells in the wells of a plate. A further station is a pipette station wherein liquid is removed or inserted into the wells of a plate. A still further station is a manipulator station wherein manipulation of cells in the wells of a plate, for example scraping, is performed. In order for the plates to be acted upon at each station, a robotic transport is provided for moving the plates between stations.

According to one aspect of the disclosure, a cell culture incubator includes an incubator cabinet having a transfer chamber and an internal chamber. In some embodiments, a source of a sterilizing gas (e.g., a source of ozone gas such as an ozone generator, a source of hydrogen peroxide gas/vapor) is connected to or included in the incubator. In some embodiments, a source of sterilizing liquid (e.g., a source or dispenser of ethanol, hydrogen peroxide solutions or sodium hypochlorite solutions) is connected to or included in the incubator. In some embodiments, a sterilization gas source (e.g. an ozone generator) and one or more pumps operatively coupled with the sterilization gas source (e.g., ozone generator) are connected to or included in the incubator. The pump can be configured for supplying ozone gas to the transfer chamber, the internal chamber, or both. The pump can also be configured for removing sterilization gas (e.g., ozone gas) from the transfer chamber, the internal chamber, or both.

In some embodiments, the cell culture incubator also includes an external door opening from an external environment to the transfer chamber, a transfer chamber door opening from the transfer chamber to the internal chamber, and a transfer device for moving one or more items between the transfer chamber and the internal chamber. In some embodiments, the internal chamber is configured to hold a plurality of cell culture vessels (e.g. flasks, suspension culture flasks, spinner flasks, plates, petri dishes and bags) and/or other items (e.g., one or more supplies such as disposable supplies required for cell manipulation, for example, pipette tips). In some embodiments, the sterilization medium generator is in fluid communication with the transfer and/or internal chamber. In some embodiments, the external door forms a substantially gas-tight seal when closed. In some embodiments, the transfer chamber is configured to hold a plurality of cell culture vessels (e.g. flasks, plates, petri dishes and bags) and/or other items (e.g., one or more supplies such as disposable supplies required for cell manipulation, for example, pipette tips).

In some embodiments, the incubator further comprises a controller for controlling operation of the transfer device for moving one or more items into, within or out from the incubator. In some embodiments, the controller is located exterior to the incubator cabinet. In some embodiments, the controller comprises a computer. In some embodiments, the incubator further comprises a cell culture vessel transfer device for moving one or more cell culture vessels within the internal chamber. In some embodiments, the cell culture vessel transfer device comprises one or more robotic elements.

In some embodiments, one or more pumps are configured to remove the ozone gas or other gaseous sterilizing agent from the incubator cabinet. In some embodiments, one or more reversible pumps are provided that are configured to both supply and remove gas (depending on mode of operation) from the transfer chamber and/or internal chamber. In some embodiments, an incubator includes a decomposition catalyst (e.g., in the transfer chamber) to accelerate breakdown of a sterilizing gas and help remove it safely from the internal chamber. Non-limiting examples of decomposition catalysts include $MnO_2$, $NiO_2$, charcoal, etc., or a combination thereof.

In some embodiments, the incubator further comprises a monitoring system. In some embodiments, the monitoring system monitors the addition and/or removal of a sterilizing agent to or from the transfer chamber and/or the internal chamber. In some embodiments, the monitoring system monitors the temperature, humidity, gas (e.g. $O_2$, $CO_2$, $N_2$, etc.) concentration within the transfer chamber and/or the internal chamber. In some embodiments, the monitoring system comprises probes and/or sensors. In some embodiments, the probes and/or sensors are located in the internal chamber and/or transfer chamber of the incubator. In some embodiments, the probes and/or sensors are electronically connected to a display panel, e.g., present on the exterior of the incubator cabinet. In some embodiments, one or more controllers are attached to the sensors and other systems to control the internal environment of the incubator based on the sensed incubator conditions.

In some embodiments, the incubator further comprises a fluid filtration system. In some embodiments, the fluid filtration system filters gas or vapor that is entering and/or exiting the incubator. A fluid filtration system can be a liquid filter and/or a gas (e.g., air, ozone, etc.) filter. In some embodiments, the fluid filtration system filters liquids entering and/or exiting the incubator. In some embodiments, the fluid filtration system is a sterilizing filter (e.g. a UV filter sterilizer or heat sterilizer).

Autologous cell therapy is a personalized medicine technique in which human cells are implanted, transplanted, infused, or transferred back into the individual from whom the cells or tissue were originally recovered. For example, chondrocytes may be isolated from a patient having a cartilage injury, expanded in a culture system and then implanted back into the patient for the purposes of alleviating joint pain associated with the cartilage injury. Other examples of autologous cell therapies include autologous dendritic cells, mesenchymal stromal cells and T lymphocytes. Autologous cell therapies have many advantages including immediate donor availability, reduced cell or tissue rejection, and reduced graft-versus-host disease. Additionally, the autologous nature of the cells means there is no need for HLA matching and immunosuppression of the cell recipient. Although there are many therapeutic advantages of autologous cell therapy, several challenges in the manufacturing and production of autologous cell cultures impose barriers to commercial success.

One challenge for the manufacturing autologous cell therapies is "scale-out", or the ability to simultaneously produce multiple batches of autologous cell cultures from different donors. Strict aseptic conditions must be maintained in order to prevent cross-contamination between autologous cultures from different patients. Some currently used methods and devices for autologous cell culture rely on manual culture techniques, which can introduce contaminants to cultures and expose cultures to non-aseptic conditions and/or variations of the physical environment (e.g., changes in temperature, humidity, etc., or any combination thereof). Other cell culture apparatus do not provide the ability to culture cells from multiple donors with minimal risk of cross-contamination. Accordingly, new cell culture systems and methods are provided herein that permit remote maintenance and significant scale-out capabilities of multiple cell cultures while maintaining stringent aseptic conditions.

In some aspects, this document provides a method for producing a mammalian cell culture that include: (a) introducing a mammalian cell sample into a cell culture vessel in the presence of growth media, wherein the vessel includes a passage configured to permit materials to be aseptically transferred into or out of the vessel; and, (b) expanding the cell sample in an incubator into a mammalian cell culture, wherein the incubator comprises a sterile inner growth chamber.

In some embodiments, the cell sample is introduced into the cell culture vessel through the passage. In some embodiments, the passage of the vessel is covered by a gas-permeable membrane. In some embodiments, a membrane on a culture vessel provides a one-way valve or "environmental" interface through which the gaseous environment may be controlled within the closed, autologous culture vessel. In some embodiments, multiple closed systems (e.g., within a single, temperature-controlled environment) may be provided in the form of a plurality of autologous culture vessels. In some embodiments, an overall incubator environment maintains the environmental temperature of the collective system. In some embodiments, the internal gaseous environment of each closed vessel is maintained through an interface (e.g., a plumbing interface) which contains a set of membrane "valves" for gas exchange. In such embodiments, this configuration facilitates control, monitoring and documentation of independent autologous cultures.

In some embodiments, the method further comprises aseptically introducing growth media to the cell culture through the passage in the vessel.

In some embodiments, the method further comprises aseptically introducing a biological material to the cell culture through the opening in the vessel. In some embodiments, the biological material is a cell growth factor. In some embodiments, the biological material is a nucleic acid molecule. In some embodiments, the nucleic acid molecule is a nucleic acid vector. In some embodiments, the nucleic acid vector is a transfection vector. In some embodiments, the nucleic acid vector is a transduction vector. In some embodiments, the nucleic acid vector comprises transgenic material. In some embodiments, the biological material is an enzyme (e.g., a nuclease, a ligase, a polymerase, or other enzyme that modifies a nucleic acid). In some embodiments, the biological material comprises a mixture of nucleic acid modifying enzyme(s) and one or more nucleic acids.

In some embodiments, the methods further comprise aseptically monitoring conditions of the growth media. In some embodiments, the incubator is maintained at a constant temperature range. In some embodiments, the incubator is maintained at about 37 degrees Celsius.

In some embodiments, the methods further comprise aseptically monitoring conditions of the cell.

In some embodiments, the methods further comprise aseptically adding reagents to control the chemical composition of the growth media (e.g., the pH, the concentration of glucose, the concentration of lactate, the concentration of other small molecules, or the overall osmolality of the growth media).

In some embodiments, the methods further comprise aseptically imaging the cell culture. In some embodiments, the method further comprises filtering the cell culture. In some embodiments, the method further comprises aseptically removing an aliquot of the cell culture. In some embodiments, the incubator is a cell culture system as described herein.

In some aspects, this document provides a cell culture system comprising an incubator cabinet comprising: a transfer chamber; one or more internal chambers; an external door opening from an external environment to the transfer chamber; a first internal door opening from the transfer chamber to a first internal chamber; a second internal door opening from the transfer chamber to a second internal chamber; and a transfer device for moving one or more items between the transfer chamber and the first internal chamber, and/or between the transfer chamber and the second internal chamber and/or between the second internal chamber and the first internal chamber.

In some embodiments, the cell culture system further comprises a sterilization medium supply (e.g., an ozone generator) coupled to a pump, wherein the sterilization medium supply (e.g., the ozone generator) is configured for supplying sterilization medium (e.g., ozone gas) to the transfer chamber. In some embodiments, the sterilization medium supply (e.g., ozone generator) is configured for supplying sterilization medium (e.g., ozone gas) to the one or more internal chambers.

In some embodiments, the external door forms a substantially gas-tight seal when closed. In some embodiments, the first internal door and the second internal door each forms a substantially gas-tight seal when closed.

In some embodiments, the pump is configured to remove sterilization medium from the transfer chamber and/or one or more internal chambers.

In some embodiments, the storage chamber comprises a storage location. In some embodiments, the storage location is configured to hold a plurality of cell culture vessels. In some embodiments, each vessel of the plurality of cell culture vessels contains cells from a different patient. In some embodiments, each vessel of the plurality of cell culture vessels is tagged with a unique barcode.

In some embodiments, the internal chamber comprises an imager and an imaging location. In some embodiments, the imager is a holographic imager. In some embodiments, the imager is a microscope, such as a bright-field microscope or a fluorescence microscope. In some embodiments, the cell culture system further comprises a controller for the imager.

In some embodiments, the internal chamber comprises a manipulator and a manipulation location. In some embodiments, the manipulator is a cell picker. In some embodiments, the manipulator comprises a fluid handling system.

In some embodiments, the cell culture system further comprises a controller for the manipulator.

In some embodiments, the internal chamber comprises a fluid storage location. In some embodiments, the internal chamber comprises a cell sorting or cell isolation apparatus. In some embodiments, the cell sorting or cell isolation apparatus is a centrifuge. In some embodiments, the cell sorting or cell isolation apparatus is a Fluorescence-Activated Cell Sorting (FACS) machine. In some embodiments, the internal chamber comprises a microfluidic device for imaging and/or manipulating individual cells.

In some embodiments, a transfer device or transport is used to move cells, cell media, or cell plates from one location to another.

In some embodiments, the transfer device comprises one or more robotic elements. The robotic elements in some embodiments is a wheeled robotic element or transport. In some embodiments the wheeled robotic element is trackless. In some embodiments, the cell culture system further comprises a controller for the transfer device. In some embodiments, the controller for the imager, the controller for the manipulator, and/or the controller for the transfer device are external to the incubator cabinet. In some embodiments, the controller for the imager, the controller for the manipulator and/or the controller for the transfer device comprises a single processor. In some embodiments, the controller for the imager, the controller for the manipulator, and/or the controller for the transfer device comprise a computer. In some embodiments, a single computer controls the imager, the manipulator, and/or the transfer device.

In some embodiments, the cell culture system further comprises a barcode scanner. In some embodiments, the barcode scanner is connected to a computer, wherein the computer is external to the incubator cabinet.

In some aspects, this document provides a cell culture system comprising two or more cell culture vessels, wherein each vessel comprises cells from a different patient and wherein each vessel comprises a passage configured to permit materials to be aseptically passed into or out from the vessel.

The cell culture incubator may include one or more imagers to image cells. In some embodiments, incubator cabinets provided herein are configured with a microscope or other imager for purposes of monitoring cell growth, viability or other aspect of cells. In some embodiments, the microscope or imager is used in conjunction with an assay performed within the incubator cabinet, such as an image based phenotypic screen or assay. In certain embodiments, an imager includes one or more lenses, fibers, cameras (e.g., a charge-coupled device camera), apertures, mirrors, light sources (e.g., a laser or lamp), or other optical elements. An imager may be a microscope. In some embodiments, the imager is a bright-field microscope. In other embodiments, the imager is a holographic imager or microscope. In other embodiments the imager is a phase-contrast microscope. In other embodiments, the imager is a fluorescence imager or microscope.

As used herein, the fluorescence imager is an imager which is able to detect light emitted from fluorescent markers present either within or on the surface of cells or other biological entities, said markers emitting light in a specific wavelength when absorbing a light of different specific excitation wavelength.

As used herein, a "bright-field microscope" is an imager that illuminates a sample and produces an image based on the light absorbed by the sample. Any appropriate bright-field microscope may be used in combination with an incubator provided herein.

As used herein, a "phase-contrast microscope" is an imager that converts phase shifts in light passing through a transparent specimen to brightness changes in the image. Phase shifts themselves are invisible but become visible when shown as brightness variations. Any appropriate phase-contrast microscope may be used in combination with an incubator provided herein.

As used herein, a "holographic imager" is an imager that provides information about an object (e.g., sample) by measuring both intensity and phase information of electromagnetic radiation (e.g., a wave front). For example, a holographic microscope measures both the light transmitted after passing through a sample as well as the interference pattern (e.g., phase information) obtained by combining the beam of light transmitted through the sample with a reference beam.

A holographic imager may also be a device that records, via one or more radiation detectors, the pattern of electromagnetic radiation, from a substantially coherent source, diffracted or scattered directly by the objects to be imaged, without interfering with a separate reference beam and with or without any refractive or reflective optical elements between the substantially coherent source and the radiation detector(s).

In some embodiments, an incubator cabinet includes a single imager. In some embodiments, an incubator cabinet includes two imagers. In some embodiments, the two imagers are the same type of imager (e.g., two holographic imagers, two phase-contrast microscopes or two bright-field microscopes). In some embodiments, the first imager is a bright-field microscope and the second imager is a holographic imager. In some embodiments, the first imager is a phase-contrast microscope and the second imager is a holographic imager. In some embodiments, the first imager is a phase-contrast microscope and the second imager is a bright-field microscope. In some embodiments, an incubator cabinet comprises more than 2 imagers. In some embodiments, cell culture incubators comprise three imagers. In some embodiments, cell culture incubators having 3 imagers comprise a holographic microscope, a bright-field microscope, and a fluorescence microscope. In some embodiments, cell culture incubators having 3 imagers comprise a holographic microscope, a phase-contrast microscope, and a fluorescence microscope.

As used herein, an "imaging location" is the location where an imager images one or more cells. For example, an imaging location may be disposed above a light source and/or in vertical alignment with one or more optical elements (e.g., lens, apertures, mirrors, objectives, and light collectors).

Holographic Microscopy

In some embodiments, holographic microscopy is used to obtain images (e.g., a collection of three-dimensional microscopic images) of cells for analysis (e.g., cell counting) during culture (e.g., long-term culture) in an incubator (e.g., within an internal chamber of an incubator as described herein). In some embodiments, a holographic image is created by using a light field, from a light source scattered off objects, which is recorded and reconstructed. In some embodiments, the reconstructed image can be analyzed for a myriad of features relating to the objects. In some embodiments, methods provided herein involve holographic interferometric metrology techniques that allow for non-invasive, marker-free, quick, full-field analysis of cells, generating a high resolution, multi-focus, three-dimensional representation of living cells in real time.

In some embodiments, holography involves shining a coherent light beam through a beam splitter, which divides the light into two equal beams: a reference beam and an illumination beam. In some embodiments, the reference beam, often with the use of a mirror, is redirected to shine directly into the recording device without contacting the object to be viewed. In some embodiments, the illumination beam is also directed, using mirrors, so that it illuminates the object, causing the light to scatter. In some embodiments, some of the scattered light is then reflected onto the recording device. In some embodiments, a laser is generally used as the light source because it has a fixed wavelength and can be precisely controlled. In some embodiments, to obtain clear images, holographic microscopy is often conducted in the dark or in low light of a different wavelength than that of the laser in order to prevent any interference. In some embodiments, the two beams reach the recording device, where they intersect and interfere with one another. In some embodiments, the interference pattern is recorded and is later used to reconstruct the original image. In some embodiments, the resulting image can be examined from a range of different angles, as if it was still present, allowing for greater analysis and information attainment.

In some embodiments, digital holographic microscopy is used in incubators described herein. In some embodiments, digital holographic microscopy light wave front information from an object is digitally recorded as a hologram, which is then analyzed by a computer with a numerical reconstruction algorithm. In some embodiments, the computer algorithm replaces an image forming lens of traditional microscopy. The object wave front is created by the object's illumination by the object beam. In some embodiments, a microscope objective collects the object wave front, where the two wave fronts interfere with one another, creating the hologram. Then, the digitally recorded hologram is transferred via an interface (e.g., IEEE1394, Ethernet, serial) to a PC-based numerical reconstruction algorithm, which results in a viewable image of the object in any plane.

In some embodiments, in order to procure digital holographic microscopic images, specific materials are utilized. In some embodiments, an illumination source, generally a laser, is used as described herein. In some embodiments, a Michelson interferometer is used for reflective objects. In some embodiments, a Mach-Zehnder interferometer for transmissive objects is used. In some embodiments, interferometers can include different apertures, attenuators, and polarization optics in order to control the reference and object intensity ratio. In some embodiments, an image is then captured by a digital camera, which digitizes the holographic interference pattern. In some embodiments, pixel size is an important parameter to manage because pixel size influences image resolution. In some embodiments, an interference pattern is digitized by a camera and then sent to a computer as a two-dimensional array of integers with 8-bit or higher grayscale resolution. In some embodiments, a computer's reconstruction algorithm then computes the holographic images, in addition to pre- and post-processing of the images.

Phase Shift Image

In some embodiments, in addition to the bright field image generated, a phase shift image results. Phase shift images, which are topographical images of an object, include information about optical distances. In some embodiments, the phase shift image provides information about transparent objects, such as living biological cells, without distorting the bright field image. In some embodiments, digital holographic microscopy allows for both bright field and phase contrast images to be generated without distortion. Also, both visualization and quantification of transparent objects without labeling is possible with digital holographic microscopy. In some embodiments, the phase shift images from digital holographic microscopy can be segmented and analyzed by image analysis software using mathematical morphology, whereas traditional phase contrast or bright field images of living unstained biological cells often cannot be effectively analyzed by image analysis software.

In some embodiments, a hologram includes all of the information pertinent to calculating a complete image stack. In some embodiments, since the object wave front is recorded from a variety of angles, the optical characteristics of the object can be characterized, and tomography images of the object can be rendered. From the complete image stack, a passive autofocus method can be used to select the focal plane, allowing for the rapid scanning and imaging of surfaces without any vertical mechanical movement. Furthermore, a completely focused image of the object can be created by stitching the sub-images together from different focal planes. In some embodiments, a digital reconstruction algorithm corrects any optical aberrations that may appear in traditional microscopy due to image-forming lenses. In some embodiments, digital holographic microscopy advantageously does not require a complex set of lenses; but rather, only inexpensive optics, and semiconductor components are used in order to obtain a well-focused image, making it relatively lower cost than traditional microscopy tools.

Applications

In some embodiments, holographic microscopy can be used to analyze multiple parameters simultaneously in cells, particularly living cells. In some embodiments, holographic microscopy can be used to analyze living cells, (e.g., responses to stimulated morphological changes associated with drug, electrical, or thermal stimulation), to sort cells, and to monitor cell health. In some embodiments, digital holographic microscopy counts cells and measures cell viability directly from cell culture plates without cell labeling. In other embodiments, the imager can be used to examine apoptosis in different cell types, as the refractive index changes associated with the apoptotic process can be quantified via digital holographic microscopy. In some embodiments, digital holographic microscopy is used in research regarding the cell cycle and phase changes. In some embodiments, dry cell mass (which can correlate with the phase shift induced by cells), in addition to other non-limiting measured parameters (e.g., cell volume, and the refractive index), can be used to provide more information about the cell cycle at key points.

In some embodiments, the method is also used to examine the morphology of different cells without labeling or staining. In some embodiments, digital holographic microscopy can be used to examine the cell differentiation process; providing information to distinguish between various types of stem cells due to their differing morphological characteristics. In some embodiments, because digital holographic microscopy does not require labeling, different processes in real time can be examined (e.g., changes in nerve cells due to cellular imbalances). In some embodiments, cell volume and concentration may be quantified, for example, through the use of digital holographic microscopy's absorption and phase shift images. In some embodiments, phase shift images may be used to provide an unstained cell count. In some embodiments, cells in suspension may be counted, monitored, and analyzed using holographic microscopy.

In some embodiments, the time interval between image acquisitions is influenced by the performance of the image recording sensor. In some embodiments, digital holographic microscopy is used in time-lapse analyses of living cells. For example, the analysis of shape variations between cells in suspension can be monitored using digital holographic images to compensate for defocus effects resulting from movement in suspension. In some embodiments, obtaining images directly before and after contact with a surface allows for a clear visual of cell shape. In some embodiments, a cell's thickness before and after an event can be determined through several calculations involving the phase contrast images and the cell's integral refractive index. Phase contrast relies on different parts of the image having different refractive index, causing the light to traverse different areas of the sample with different delays. In some embodiments, such as phase contrast microscopy, the out of phase component of the light effectively darkens and brightens particular areas and increases the contrast of the cell with respect to the background. In some embodiments, cell division and migration are examined through time-lapse images from digital holographic microscopy. In some embodiments, cell death or apoptosis may be examined through still or time-lapse images from digital holographic microscopy.

In some embodiments, digital holographic microscopy can be used for tomography, including but not limited to, the study of subcellular motion, including in living tissues, without labeling.

In some embodiments, digital holographic microscopy does not involve labeling and allows researchers to attain rapid phase shift images, allowing researchers to study the minute and transient properties of cells, especially with respect to cell cycle changes and the effects of pharmacological agents.

As used herein, a "manipulator for manipulating cells" refers to a device for manipulating cells in the internal chamber. The manipulator may include one or more needles, capillaries, pipettes, and/or micromanipulators. In some embodiments, a manipulator comprises one or more cell scrapers. As used herein, "cell scraper" refers to a device comprising a scraping edge suitable for scraping cells off of a surface. In some embodiments, a cell scraper comprises a handle portion comprising a elongate member extending from a proximal region that is attachable or connectable with a manipulator base and a distal region that comprises a scraping edge. In some embodiments, a cell scraper is a contiguous structure (e.g., a molded structure) comprising a scraping edge. However, in some embodiments, a cell scraper comprises one or more interconnected parts. For example, in some embodiments, a cell scraper comprises a handle having an interface for replaceably connecting or attaching a scraping edge or scraping edge assembly to the handle. In some embodiments, the scraping edge is a portion of a cell scraper contactable with the surface of a cell culture vessel or other surface and suitably configured for scraping matter from the surface for cleaning the surface and/or for scraping cells adhering to the surface without substantially killing the cells, e.g., by mechanically lysing the cells. In some embodiments, it is desirable for a scraping edge or scraping edge assembly to be disposable in order to prevent cross-contamination between cell cultures. Thus, in some embodiments, the scraping edge or scraping edge assembly is disposable.

In some embodiments, a scraping edge comprises a blade, wiper or an otherwise substantially planar surface comprising an edge (e.g., a beveled edge) that is configured for removing cells from the surface of a cell culture vessel when pushed or pulled along the surface of the cell culture vessel. In some embodiments, a scraping edge can be made of a polymer or combination of polymers (e.g., plastic, silicone), glass, metal or any other suitable material. However, in some embodiments, the scraping edge comprises mechanical/material properties that allow for a definable range of scraping edge deflection on contact, which allows for close control of angle of contact with the cell culture vessel surface/adherent cells. In some embodiments, edge of the cell scraper is formed from a polymer. Examples of polymers used to form scraping edge include, but are not limited to, silicone, polyurethane, polyethylene, polyester, polypropylene, polybutylene, polystyrene, polyvinyl chloride (PVC), and nylon. In some embodiments, a blade comprises a geometry configured for excision of certain cells (e.g., pre-differentiated cells) from a larger population of cells (e.g., healthy stem cell colonies).

In certain embodiments, a cell scraper is configured to perform scraping and liquid handling functions. For example, in some embodiments a scraper further comprises an opening(s) (e.g., orifice(s)) in close proximity to a scraping edge (e.g., blade) together with an accompanying port to a pipet head or other fluid movement device (e.g., a pump, vacuum chamber), thus allowing simultaneous scraping and aspiration of cellular material. Such a configuration is useful, in some embodiments, for the option for cell cleaning or colony picking (e.g., in the context of stem cells separation).

In some embodiments, the manipulator comprises one or more cell scrapers. In some embodiments, each cell scraper comprises a handle portion comprising a elongate member extending from a proximal region that is attachable or connectable with a manipulator base and a distal region that comprises a scraping edge. In some embodiments, each cell scraper comprises a contiguous structure (e.g., a molded structure) comprising a scraping edge. In some embodiments, each cell scraper comprises one or more interconnected parts. In some embodiments, each cell scraper comprises a handle having an interface for replaceably connecting a scraping edge assembly to the handle. Thus, in some embodiments, a disposable scraper edge is provided that is detachable or releasable from the scraper handle. In some embodiments, each cell scraper comprises a scraper edge contactable with the surface of a cell culture vessel and configured for scraping cells adhering to the surface without substantially killing the cells. In some embodiments, the incubator further comprises a controller configured for controlling the manipulator to modulate the contact pressure between a scraping edge of the cell scraper and the surface of a cell culture vessel.

In some embodiments, the incubator further comprises a sensor connected to the cell scraper (e.g., a strain gauge sensor) that provides signal to a controller informative of a sensed pressure between a scraping edge of the cell scraper and the surface of a cell culture vessel, wherein the controller is configured to transmit a control signal to the manipulator to increase or decrease the pressure between a scraping edge of the cell scraper and the surface of a cell culture vessel in response to the sensed pressure. In some embodiments, each cell scraper is readily removable from the manipulator. In some embodiments, each cell scraper is configured to perform scraping and liquid handling functions. In some embodiments, each cell scraper comprises a scraping edge configured to allow a definable range of scraping edge deflection on contact with a cell culture vessel. In some embodiments, each cell scraper comprises one or more components formed from a polymer. In some embodiments, each cell scraper further comprises an opening configured for aspirating cells and/or cell culture media, wherein the opening is positioned in close proximity to a scraping edge.

In some embodiments, the cell scraper is disposable. In some embodiments, the cell scraper is configured to perform scraping and liquid handling functions. In some embodiments, the cell scraper comprises a scraping edge configured to allow a definable range of scraping edge deflection on contact with a cell culture vessel. In some embodiments, a scraping edge is formed from a polymer. In some embodiments, the edge comprises a geometry configured for excision of certain cells (e.g., pre-differentiated cells) from a larger population of cells (e.g., healthy stem cell colonies). In some embodiments, the scraping edge further comprises an opening (e.g., an orifice) configured for transporting (e.g., aspirating, depositing, or aspirating and depositing) cells and or cell culture media, wherein the opening (e.g., orifice) is positioned in close proximity to the scraping blade.

In some embodiments, an opening (e.g., orifice). In some embodiments, the opening is configured for transporting (e.g., aspirating, depositing, or aspirating and depositing) cells and/or cell culture media and forms part of (e.g., is connected to) a channel. In some embodiments, a channel is integrated into a cell scraper (e.g., running along the inside or outside of a cell scraper handle and/or scraping blade). In some embodiments, the incubator further comprises one or more additional manipulators, each having at least one cell scraper. In some embodiments, the at least one cell scraper (e.g., of the one or more manipulators) is at least 2, 3, 4, 5, 10, 15, 20, 50, 100, 200, 300, 500, or up to 1000 cell scrapers.

In some embodiments, the cell culture incubator further comprises a controller of the manipulator for manipulating the cells. In some embodiments, the controller of the manipulator is configured to quantify and modulate the contact force between the scraping edge and the surface of a cell culture vessel to which cells are adhered. In some embodiments, the controller is located exterior to the incubator cabinet. In some embodiments, the controller is inside or integrated into the incubator cabinet. In some embodiments, the controller comprises a computer.

In some embodiments, an imager is provided in the incubator cabinet. In some embodiments, the imager is configured to enable selective scraping of cells with the manipulator while imaging the cells to be scraped or that are scraped. In some embodiments, the imager is a holographic microscope. In some embodiments, the imager is a bright-field microscope. In some embodiments, the imager is a fluorescence microscope. In some embodiments, the imager is a phase-contrast microscope. In some embodiments, cell culture incubators further comprise a second imager, or a second imager and a third imager. In some embodiments, cell culture incubators having 3 imagers comprise a holographic microscope, a bright-field microscope, and a fluorescence microscope. In some embodiments, cell culture incubators having 3 imagers comprise a phase-contrast microscope, a holographic microscope, and a fluorescence microscope. In some embodiments, the imager is used to analyze the cells and determine automatically an area to be scraped. In other embodiments, the automatic selection of an area to be scraped is modified by an operator. In other embodiment, the operator selects manually an area to be scraped from the plurality of images acquired by the imagers.

In some embodiments, the one or more cell culture vessels are flasks, suspension culture flasks, spinner flasks, plates, petri dishes and/or bags. In some embodiments, the one or more cell culture vessels comprise fiducial marks for facilitating alignment of the one or more cell culture vessels to the imager and the manipulator.

In some embodiments, the manipulator for manipulating the cells is a cell picker. In some embodiments, the cell culture incubator further comprises a controller of the manipulator for manipulating the cells. In some embodiments, when the one or more cell culture vessels are moved from an imaging location to a manipulating location or from a manipulating location to an imaging location, the one or more cell culture vessels are substantially aligned.

In some aspects, this document provides a cell culture incubator comprising: an incubator cabinet comprising an internal chamber for incubation of cells in one or more cell culture vessels, wherein the internal chamber is configured to hold the one or more cell culture vessels; a door opening to the internal chamber; a holographic imager comprising a first imaging location, the holographic imager configured for imaging the cells within the internal chamber when the one or more cell culture vessels are at the first imaging location; a second imager comprising a second imaging location, the imager configured for imaging the cells within the internal chamber when the one or more cell culture vessels are at the second imaging location; a manipulator for manipulating the cells in the one or more cell culture vessels at the second imaging location; and a cell culture vessel transfer device for moving the one or more cell culture vessels from the first imaging location to the second imaging location or from the second imaging location to the first imaging location.

In some embodiments, the holographic imager is a holographic microscope. In some embodiments, the second imager is a bright-field microscope. In some embodiments, the second imager is a fluorescence microscope. In some embodiments, cell culture incubators further comprise a third imager. In some embodiments, cell culture incubators comprise three imagers. In some embodiments, cell culture incubators having three imagers comprise a holographic microscope, a bright-field microscope, and a fluorescence microscope.

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which:

BRIEF DESCRIPTION OF DRAWINGS

FIG. 11 shows a schematic of a cell culture incubator having a second imager; FIG. 12 shows a schematic of a cell culture incubator, wherein the imaging location and the manipulating location are the same location;

FIG. 14 shows a schematic of a cell culture incubator having a manipulator comprising a cell scraper; FIG. 15 is a schematic of an illustrative embodiment of a cell culture system comprising an incubator cabinet comprising an internal chamber containing a plurality of cell culture vessels. Each cell culture vessel contains a cell culture from a different subject;

FIG. 16A shows a schematic of a cell culture system comprising an incubator cabinet comprising a transfer chamber and an internal chamber; FIG. 16B shows a schematic of a cell culture incubator comprising an incubator cabinet comprising a transfer chamber, an internal chamber containing a plurality of cell culture vessels, an ozone generator, and a pump;

DETAILED DESCRIPTION

Figure 1:
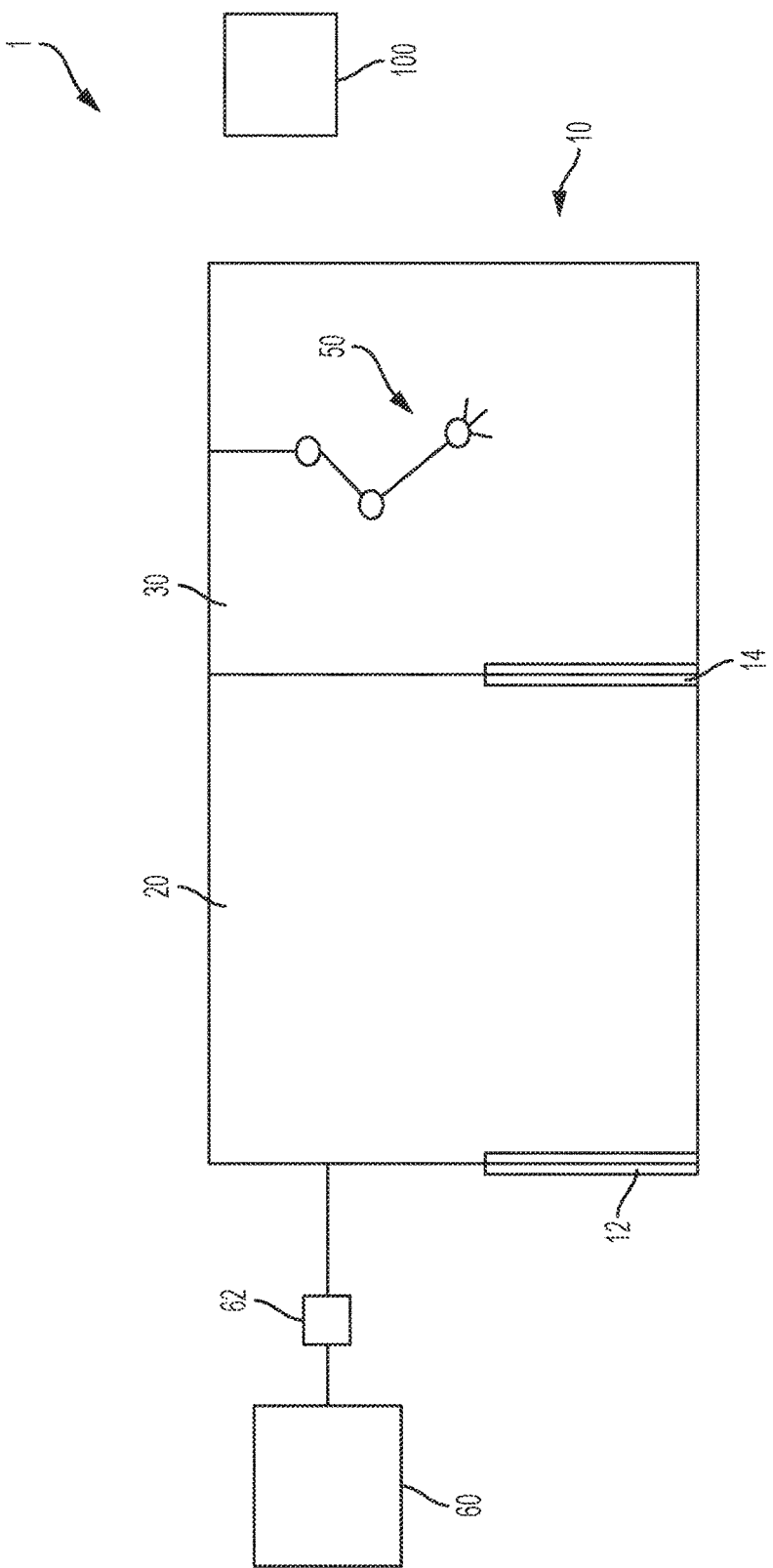
FIG. 1 is a schematic of an illustrative embodiment of a cell culture incubator having an incubator cabinet with a transfer chamber and an internal chamber according to one embodiment.

Aspects of the disclosure relate to automated incubators that enable productive long-term cell culture. It has been appreciated that, when items from the external environment are inserted into a cell culture incubator, such items may bring along contaminants that may contaminate the cells held inside the incubator. Furthermore, it has been recognized that there is a need for a cell culture incubator that reduces exposure of cells to contaminants. It has also been appreciated that, each time the door to a conventional single-chamber cell culture incubator is opened, the internal conditions (e.g., temperature, gas mixture, and/or humidity) are changed due to exposure to the external environment. It takes time for the incubator to adjust back to desirable levels. In the meantime, the cells held within the incubator are subjected to fluctuating conditions, which may negatively affect the health or activity of the cells. It has been recognized that there is a need for a cell culture incubator that reduces the amount of condition fluctuations that cells are subjected to when items are moved in and out of an incubator.

According to one aspect, a cell culture incubator includes an airlock arrangement that permits items to be transferred from an external environment into an internal chamber of the cell culture incubator while helping to maintain the conditions and/or sterility of the internal chamber.

In some embodiments, the cell culture incubator may include an incubator cabinet with a transfer chamber and an internal chamber. The transfer chamber serves as an intermediate space in which items can be sterilized before entering the internal chamber and/or conditions can be equilibrated with the internal chamber before communication with the internal chamber is opened. The cell culture incubator may include at least two doors to create an airlock arrangement. In some embodiments, an external door is configured to open and close to permit communication between the transfer chamber and the external environment. In some embodiments, an internal door is configured to open and close to permit communication between the transfer chamber and the internal chamber. Operation of the external and/or internal doors may be provided in an automated fashion.

In some embodiments, a door is an element that permits communication between two or more environments or regions when opened and prevents communication between the two or more environments or regions when closed. A door may be of any type, such as a sliding door, pocket door, swinging door, hinged door, revolving door, pivot door, or folding door. The door may be manually, mechanically, or electrically operated. For example, an operator may open or close a door by manually grasping, pulling, pushing, and/or otherwise physically interacting with the door or an element thereof (e.g., a handle) or by operating a mechanical control (e.g., a button, toggle, spin-wheel, key, switch, cursor, screw, dial, screen, or touch-screen). In certain embodiments, a door may be controlled by electrical or digital controls, such as by a computer. A door may be an automatically opening door. For example, a door may include a sensor, such as a pressure, infrared, motion, or remote sensor, that detects whether the door is open or closed and/or controls when the door opens or closes. A door may open by mechanical, pneumatic, electrical, or other means. In some embodiments, one or more doors may include one or more locking mechanisms. In particular environments, one or more doors may include one or more interlocks (e.g., a mechanical interlock such as a pin, bar, or lock or an electrical interlock such as a switch) to prevent one or more doors from opening at an undesirable time (e.g., when one or more chambers are open to the outside environment).

The airlock arrangement may be used to help decrease exposure of the internal chamber to the external environment, or exposure of the external environment to the internal chamber. In some embodiments, to utilize the airlock arrangement, one door is opened at a time. For example, an operator may open the external door to gain access to the transfer chamber. The operator may then insert item(s) such as pipette tips into the transfer chamber. An operator may operate the external door by directly manipulating the door. However, in some embodiments, an operator may operate the door indirectly by controlling the operation of the door remotely, e.g., through the use of automation configured to control opening and closing of the doors. In some embodiments, the transfer chamber door remains closed while the external door is open. In some embodiments, after item(s) are inserted into the transfer chamber, the external door is closed (e.g., directly or indirectly by an operator). Once the external door is closed, a sterilization process inside the transfer chamber is used to sterilize the inserted item(s). Once sterilization is complete, the internal door is opened and the sterilized items are moved from the transfer chamber into the internal chamber (e.g., by one or more transfer devices).

An illustrative example of how the transfer chamber helps to preserve the internal conditions of the internal chamber will now be described. When the transfer chamber is opened to the external environment, the internal chamber remains closed such that there is no communication between the external environment and the internal chamber. Once the transfer chamber is closed to the external environment, sensors inside the transfer chamber detect one or more internal conditions associated with the transfer chamber, such as temperature, humidity, gas content, air pressure, light, etc. The conditions within the transfer chamber are then adjusted (e.g., by raising/lowering the temperature, increasing/decreasing humidity, etc.) to become closer to or substantially match those of the internal chamber. Once the internal conditions between the transfer chamber and the internal chamber are sufficiently similar, the internal chamber opens to the transfer chamber. Items from the transfer chamber can then be moved into the internal chamber. With the conditions in the transfer chamber being close to or substantially matching those in the internal chamber, the conditions of the internal chamber are not subjected to significant fluctuations when the internal door is opened (e.g., when items are moved from the transfer chamber to the internal chamber).

In some embodiments, the environment inside an incubator is controlled by a control system that may be configured to control the temperature, humidity, carbon dioxide, oxygen and other gaseous components (e.g., sterilization gases, such as, ozone, and hydrogen peroxide) inside the incubator (e.g., in one or more internal chambers). In some embodiments, a control system controls the environmental conditions (e.g., temperature, humidity, carbon dioxide, oxygen and other gaseous components) within each internal chamber separately. For example, in order to protect sensitive mechanical, electronic and optical components, the humidity of an internal chamber may be maintained at a lower level than an internal chamber (e.g., a level in a range of 30% to under 70% relative humidity). In some embodiments, the incubator is further provided with a monitoring system with predefined sensors. Examples of monitoring devices include but are not limited to oxygen monitors, carbon dioxide monitors, ozone gas detectors, hydrogen peroxide monitors and multi gas monitors. For example, in some embodiments, an incubator includes a plurality of sensors responsive to different parameters relevant to cell growth, which may include temperature, air purity, contaminant levels, pH, humidity, N2, CO2, O2 and light. By means of this monitoring system, parameters in the incubator can be measured using sensors for the duration of a culture or process. In some embodiments, parameters measured by the sensors are transmitted by the monitoring system via a line to a computer-controlled monitoring and control system for further processing as discussed elsewhere herein.

In some embodiments, an environmental monitoring system can be used in conjunction with an incubator described herein. In some embodiments, one or more sensors that provide for the measurement of temperature, air composition (e.g., CO2 concentration, O2 concentration, etc.), and/or humidity of the system can be associated with an incubator (e.g., fitted within an incubator cabinet). In some embodiments, one or more such sensors can be incorporated as part of an incubator (e.g., attached to, integral to, or otherwise connected to an internal wall or door of the incubator). In some cases, one or more sensors can be positioned at any suitable location(s) outside or inside an incubator cabinet (e.g., within a transfer chamber and/or an internal chamber, for example attached to an internal wall, and/or upper or lower internal surface).

In some embodiments, a gas sensor is provided that can provide a reading in real time of the concentration of gas in contact with the sensor (e.g., gas in a cabinet, or ambient air) in percent, parts per million, or any other standard unit. Gas sensors for use in the methods and incubators provided herein include CO2 sensors, O2 sensors, N2 sensors, ozone gas detectors, hydrogen peroxide monitors, multi gas monitors, and CO sensors. Such sensors are available from a number of commercial sources. In some cases, the environment of the incubator may be modulated or controlled based upon the information provided by the sensors described herein. For example, the level of CO2 in an incubator may be increased upon indication from a CO2 sensor that a lower than desirable concentration of CO2 is present in the incubator.

In some embodiments, one or more heating or cooling elements can be incorporated within the incubator (e.g., on an inner surface of the cabinet or door, and/or integrated within one or more of the walls and/or the base of the cabinet) for purposes of controlling the temperature within the incubator. In some embodiments, a heating element can be used for thawing liquids, for example, cell culture media or other reagents. In some embodiments, one or more air or oxygen sources, carbon filters, and/or one or more humidification or dehumidification systems are connected to the incubator and configured to control the level of oxygen, carbon dioxide, and/or humidity within the incubator (e.g., in response to signals from the one or more sensors in or attached to the incubator).

In some embodiments, the incubator further comprises a fluid filtration system. Generally, fluid filtration systems are used to filter gas or vapor that is entering and/or exiting the incubator. For example, a fluid filtration system may sterilize the air entering the incubator from the exterior environment, or sterilize the air exiting the incubator prior to being released into the exterior environment. Liquid filtration systems are also contemplated herein. Non-limiting examples of fluid filtration systems include air filters, carbon filters and sterilizing filters (e.g. a UV filter sterilizer or heat sterilizer).

In some embodiments, one or more controllers are attached to the sensors and other systems to control the internal environment of the incubator.

In some embodiments, an incubator can include one or more light sources (e.g., an incandescent bulb, LED, UV, or other light source). These can be placed within the incubator to illuminate regions within the cabinet. In some embodiments, the culture system operation is monitored using a camera or other light sensitive device that can be placed within or outside the incubator. In some embodiments, the light source is a sterilizing light source. For example, a UV lamp may be located within the transfer chamber and/or the interior chamber of the incubator provided herein.

In some embodiments, the incubator includes a transparent object (e.g., window) that allows visible light or other light wavelengths from within the incubator to be detected by a camera or other light sensitive device placed outside the incubator. In some embodiments, the inner surface of the transparent object can be wiped (e.g., from the inside of the cabinet) to prevent or remove condensation droplets that may accumulate (e.g., due to the humid air inside the incubator) on the inner surface and interfere with the monitoring of the system. In some embodiments, the surface can be wiped by a wiper that is automatically controlled by a controller.

In some embodiments, mechanical or electrical controls may be used to open one or more doors. In certain embodiments, an interlock arrangement is included such that only one door may be opened at a time, for example, to prevent contamination of an internal chamber by exposure to the external environment. In some embodiments, the airlock arrangement prevents the contents of the incubator from entering the external environment. For example, the airlock arrangement may prevent the release of biohazardous agents that are being cultured in the incubator. An operator may open (e.g., mechanically or by activating an electrical or digital control) the external door to gain access to the transfer chamber (e.g., to insert a pipette tip). During the time that the external door is open, the interlock may prevent the internal door from opening. After the external door is closed (e.g., mechanically or by activation of an electrical or digital control), the internal door may be opened (e.g., to transfer the pipette tip from the transfer chamber to an internal chamber).

The transfer chamber may be of any appropriate size and geometry and may be made of any suitable material. In some embodiments, a transfer chamber may include one or more plastics, polymers, metals, or glasses.

The internal chamber may include one or more windows (e.g., optical windows made of glass, plastic, composite, or other substantially transparent material for viewing an area inside the incubator cabinet). The internal chamber may be of any appropriate size and geometry. In some embodiments, an incubator cabinet may include more than one internal chamber. In other embodiments, an internal chamber may include one or more partitions to define different regions of an internal chamber. One or more internal chambers or partitions thereof may have different environmental conditions. The environment (e.g., air pressure, gas content, temperature, light, and humidity) inside an internal chamber may be measured and/or controlled by one or more meters, monitors, sensors, controls, pumps, valves, apertures, and/or light sources.

An internal chamber may be made of any useful material. In some embodiments, an internal chamber may include one or more plastics, polymers, metals, or glasses.

In some embodiments, the transfer chamber and/or the internal chamber may have a gas-tight or hermetic seal, e.g., around one or more windows or doors. In particular embodiments, sealants such as grease and/or mechanical elements such as o-rings, gaskets, septa, KF, LF, QF, quick coupling, or other sealing mechanisms may be used to establish one or more gas-tight seals. In some embodiments, grooves, depressions, protrusions, and/or molded plastic elements may facilitate in establishing one or more gas-tight seals.

In some embodiments, an incubator (e.g., an internal chamber, and/or a transfer chamber of an incubator cabinet) includes one or more windows and/or doors, that, when closed, are sealed to preserve sterility (e.g., after one or more chambers of the incubator have been sterilized). In some embodiments, each seal of the incubator is air tight up to a threshold level of pressure (e.g., up to 1 atm). In some embodiments, a gasket is provided to ensure a desired level of sealing capacity. In general, a "gasket" is understood as a mechanical seal that fills the space between two objects, generally to prevent leakage between the two objects while under compression. Gaskets are commonly produced by cutting from sheet materials, such as gasket paper, rubber, silicone, metal, cork, felt, neoprene, nitrile rubber, fiberglass, or a plastic polymer (such as polychlorotrifluoroethylene). It is often desirable that a gasket be made from a material that provides some degree of yielding such that it is able to deform and fill tightly the space it is designed for, including any slight irregularities. In some embodiments, gaskets can be used with an application of sealant directly to the gasket surface to function properly. In some embodiments, a gasket material can be a closed-cell neoprene foam which is non-reactant with carbon dioxide or ozone.

In some embodiments, a pressure test may be used to detect leaks in the internal chamber and/or the transfer chamber. In one illustrative example of a pressure test, pressurized air is delivered into a chamber and the pressure level inside the chamber is measured. A dropping pressure level may indicate a leak. For example, to test the internal chamber for leaks, pressurized air is delivered into the internal chamber with the internal door closed. A pressure sensor in the internal chamber measures pressure levels. If the pressure does not increase inside the internal chamber as pressurized air is delivered and/or if pressure levels drop once pressurized air delivery is stopped, such a condition may indicate a leak.

In some embodiments, the cell culture system further comprises a sterilization medium supply (e.g., an ozone generator) coupled to a pump, wherein the sterilization medium supply (e.g., the ozone generator) is configured for supplying sterilization medium (e.g., ozone gas) to the transfer chamber. In some embodiments, the sterilization medium supply (e.g., ozone generator) is configured for supplying sterilization medium (e.g., ozone gas) to the one or more internal chambers.

As discussed above, a sterilization process may be used to sterilize items that have been placed into the internal chamber. In some embodiments, the sterilization process uses ozone to sterilize the items. In some embodiments, the ozone is stored as a compressed gas source. The compressed ozone source can be located exterior to the incubator or within the incubator. The cell culture incubator may include an ozone generator that produces and introduce ozone gas into the incubator. In some embodiments, the ozone generator is positioned outside of the incubator cabinet, and is in fluid communication with the incubator cabinet via one or more ports into the transfer chamber and appropriate fluid conduits (e.g., tubing such as—Teflon, viton, polycarbonate, polyurethane, or other ozone-compatible tubing). One or more valves, flow meters, ozone sensors, pumps, or other devices may control the amount of ozone introduced to one or more portions of the incubator cabinet and/or be used to remove excess ozone from the incubator cabinet.

The ozone generator may operate by converting oxygen gas from ambient air into ozone gas e.g., by means of a coronal discharge, ultraviolet light, dielectric barrier discharge, or electrolysis. An ozone generator for use in conjunction with an incubator provided herein may be of any useful type, size, or geometry. In some embodiments, an incubator includes both an incubator cabinet and an ozone generator. The ozone generator may be positioned outside the incubator cabinet or may be positioned inside the incubator cabinet. Ozone gas produced by the ozone generator may be introduced into the incubator cabinet or portion thereof (e.g., a transfer chamber or an internal chamber) by means of tubing (e.g., Teflon, viton, polycarbonate, polyurethane, or other ozone-compatible tubing) and one or more ports. One or more valves, flow meters, ozone sensors, pumps, or other mechanisms may control the amount of ozone introduced to one or more portions of the incubator cabinet and/or be used to remove excess ozone from the incubator cabinet or portion thereof. In some embodiments, one or more ozone sensors may provide information to an interlock system to prevent the inner door from being opened if ozone is present at a detectable level (or above a threshold level that can be specified) in the transfer chamber. This can be useful to prevent ozone from entering the internal chamber.

In some embodiments, the sterilization process uses hydrogen peroxide gas or hydrogen peroxide vapor to sterilize the items. In some embodiments, the hydrogen peroxide vapor is stored as a compressed gas source and distributed as a low pressure, dry vapor. A hydrogen peroxide vapor generator for use in conjunction with an incubator provided herein may be of any useful type, size, or geometry. In some embodiments, an incubator includes both an incubator cabinet and a hydrogen peroxide vapor generator. The hydrogen peroxide vapor generator may be positioned outside the incubator cabinet or may be positioned inside the incubator cabinet. Hydrogen peroxide vapor produced by the hydrogen peroxide vapor generator may be introduced into the incubator cabinet or portion thereof (e.g., a transfer chamber or an internal chamber) by means of tubing (e.g., Teflon, viton, polycarbonate, polyurethane, or other ozone-compatible tubing) and one or more ports. One or more valves, flow meters, hydrogen peroxide vapor sensors, pumps, or other mechanisms may control the amount of hydrogen peroxide vapor introduced to one or more portions of the incubator cabinet and/or be used to remove excess hydrogen peroxide vapor from the incubator cabinet or portion thereof. In some embodiments, one or more hydrogen peroxide vapor sensors may provide information to an interlock system to prevent the inner door from being opened if hydrogen peroxide vapor is present at a detectable level (or above a threshold level that can be specified) in the transfer chamber. This can be useful to prevent hydrogen peroxide vapor from entering the internal chamber.

The sterilization process may be used to sterilize not only items that are inserted into the incubator but may be used to sterilize the chamber(s) of the incubator, such as in a cleaning cycle. In some embodiments, the incubator is emptied of cells and other items that would be harmed by a sterilization process. In one embodiment, a cleaning cycle entails applying 100 ppm ozone at 37 degrees C. and 80% for 15 minutes. In some cases, the transfer chamber alone may be sterilized while the internal door is closed. In other embodiments, the internal chamber alone is sterilized while the internal door is closed. In yet other embodiments, the internal chamber may be sterilized by opening the internal door or by routing sterilization medium (e.g., ozone or other gas) directly into the internal chamber.

It should be appreciated that other sterilization mediums and processes other than ozone can be used. For example, items may be sterilized using other types of chemical sterilization, steam, heat, radiation, or any other suitable type of sterilization.

A transfer device for moving one or more items may be used to move items between the transfer chamber and the internal chamber. In some embodiments, the transfer device includes a conveyor belt or other similar device for maneuvering items. In some embodiments, more than one transfer device may be included. In some embodiments, one or more transfer devices are located in the transfer chamber and/or in the internal chamber. In some embodiments, a transfer device may include one or more robotic elements. For example, a transfer device may include one or more robotic arms capable of gripping, lifting, pushing, grabbing, sliding, rotating, translating, releasing, raising, lowering, and/or tilting one or more items (e.g., pipettes).

In some embodiments, a transfer device selectively and/or releasably grips one or more pipettes or cell culture vessels or other items. In certain embodiments, a transfer device may include an arm coupled to a mechanical gripper. For example, an arm may include a mechanical gripper at or near one end for releasably gripping a pipette and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more items (e.g., pipettes or vessels) at different horizontal and vertical positions within an incubator (e.g., within a storage array located in an internal chamber).

The transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements.

As used herein, a "transfer device for moving one or more items" refers to a device that can transfer one or more items from a first location to a second location. In some embodiments, the one or more items are one or more cell culture vessels. In other embodiments, the one or more items are useful for maintenance of one or more cell culture vessels and include, but are not limited to, pipettes, capillaries, liquids (e.g., cell culture medium), nutrients, and other materials. In certain embodiments, the transfer device may transfer one or more items to or from multiple locations in an incubator. For example, a transfer device may be used to move a pipette to a maintenance location in an internal chamber for maintenance of one or more cell culture vessels. In some embodiments, an incubator includes more than one transfer device for moving one or more items (e.g., two or more separate transfer devices for transferring items between and within chambers).

In some embodiments, a transfer device includes a device that can transfer one or more cell culture vessels from a first location to a second location. In certain embodiments, the transfer device may transfer one or more items to or from multiple locations in an incubator. For example, a cell culture vessel transfer device may be used to move a cell culture vessel from a transfer chamber to an internal chamber, and/or from a storage location to an imaging location. In some embodiments, an incubator includes more than one cell culture vessel transfer device for moving one or more items (e.g., two or more separate cell culture vessel transfer devices for transferring cell culture vessels between and within chambers). A cell culture vessel transfer device may include one or more elements such as valves (e.g., electromagnetic or pneumatic valves), gears, motors (e.g., electrical or stepper motors), stages (e.g., xy or xyz stages), pistons, brakes, cables, ball-screw assemblies, rack-and-pinion arrangements, grippers, arms, pivot points, joints, translational elements, or other mechanical or electrical elements. In some embodiments, a cell culture vessel transfer device may include one or more robotic elements. For example, a cell culture vessel transfer device may include a robotic arm capable of gripping, lifting, pushing, grabbing, sliding, rotating, translating, releasing, raising, lowering, and/or tilting one or more cell culture vessels. In preferred embodiments, the cell culture vessel transfer device selectively and releasably grips one or more cell culture vessels. In certain embodiments, a cell culture vessel transfer device may include an arm coupled to a mechanical gripper. For example, an arm may include a mechanical gripper at or near one end for releasably gripping a cell culture vessel and be securely coupled to a surface or element of the incubator at or near the other end. In some embodiments, a robotic arm includes a pivot point where the mechanical gripper couples to the arm and one or more pivot and/or translational joints along the arm to permit flexible rotation and translation of a portion of the arm. In this manner, a robotic arm may access one or more cell culture vessels at different horizontal and vertical positions within an incubator (e.g., within a storage array in an internal chamber).

In some embodiments, a transfer device comprises a robotic arm. In some embodiments, the robotic arm includes a platform within an incubator cabinet that may move along a rail or conveyor running in various directions along an inner surface (e.g., inner wall, base, etc.) of incubator cabinet. In some embodiments, an incubator cabinet may be configured with more than one (e.g., 2, 3, 4, or 5, or more) robotic arms to increase the throughput of the instrument and to provide redundancy in the event that one of the robotic arms fail.

In some embodiments, a transfer device further includes a gripper assembly coupled to a robotic arm. In some embodiments, the gripper assembly includes one or more grippers mounted on the end of the robotic arm, each gripper having two or more (e.g., 3, 4, 5, or more) gripper fingers. In some embodiments, each of the gripper fingers on the robotic arm has a groove, friction plate, rubber pad, or other gripping surface. The gripping surface can allow the fingers to grip and transport various types of containers (e.g., culture vessels) within the cabinets. In some embodiments, the robotic arm may have an absolute encoder either coupled to the gripper assembly, or the platform, or a separate absolute encoder for each of the gripper assembly and/or the platform to determine whether the robotic arm is in a position where it may be safely homed (e.g., returned to a resting or storage configuration and/or location or origin of an operational coordinate system) without hitting an obstruction.

In some embodiments, because it may be desirable in certain situations for the reach of the robotic arm not to extend to some areas of the incubator cabinet, the robotic arm may instead reach these locations by inserting a container into or removing a container from a shuttle or conveyor belt located, for example on the incubator cabinet floor or other surface that moves along an axis (e.g., x-axis, y-axis) and provides access to at least some of those locations to which the robotic arm cannot reach.

In some embodiments, an incubator cabinet is designed to be used in conjunction with an external assay or laboratory automation system. For example, in some embodiments, the incubator cabinet may have a door having an opening large enough to allow the gripper arm to pivot outside of the incubator cabinet with a sufficient reach for the fingers to transport culture vessels or other containers or components between a transport line of the laboratory automation system and the incubator cabinet or the external assay components and the incubator cabinet.

In some embodiments, a robotic arm is designed to carry, among other things, culture vessels, in which case movements of the robotic arm are controlled to prevent jerking or accelerations of such vessels or other movements which may cause the spilling of samples from the vessels. In some embodiments, a robotic arm is designed to carry, among other things, culture vessels, in which case movements of the robotic arm are controlled to prevent movement of such vessels in ways which cause newly plated cells to congregate/concentrate in specific areas of the culture vessel.

In some embodiments, because a robotic arm transports vessels or other containers between specific positions in the incubator cabinet, the robotic arm or other components of the incubator can be designed to track precisely where the vessels or other containers are located. In some case, in an incubator cabinet with which a robotic arm may be used, there are likely to be areas, such as where other components of the incubator cabinet or walls of the incubator cabinet are located, and thus where certain movements of the robotic arm may be limited. In these cases, a homing mechanism can be used for each of various motors of the arms (e.g., x-motor, theta-motor and z-motor) to properly position the robotic arm to a known location after it is powered up or if a robotic arm collides with another object before resuming operation.

In some embodiments, an uninterruptible power supply ("UPS") is attached to or within the incubator cabinet, or contained with it, to allow for an orderly shut-down of incubator operations, including saving of various automation and sample information and the completion of any transport or transfer process that is underway (e.g., the transport of a container or vessel that is being carried by the robotic arm to its destination). The operator may be alerted to unauthorized opening of the incubator by an audible signal, a visual signal, an electronic signal (e.g., an email or a text message), or in some other manner. e.g. In some embodiments, a sensor or other feature is provided to detect when one or more doors of an incubator are opened (e.g., when an incubator cabinet door, such as an external or internal door, is opened). Such features are useful because they allow operators to keep track of or be warned of any unscheduled or unauthorized openings of the incubator (e.g., the incubator cabinet) that could jeopardize sterility, spoil a production, compromise an assay or experiment, etc.

In some embodiments, a radiofrequency beacon or other signal source is located within the incubator (e.g., within the incubator cabinet) that can be used to determine the location of one or more devices within the incubator cabinet (e.g., devices having sensors that can detect the signal and use it to determine their location). In some embodiments, the devices could have signal sources and the sensor(s) could be located within one or more of the chambers of an incubator cabinet (e.g., located on an internal surface of an internal chamber).

In some embodiments, light signals or lasers (e.g., a grid of laser signals) can be used to determine the location of one or more devices or components within the incubator cabinet. Such information can be communicated, e.g., wired or wirelessly, to an external computer or monitoring station. The information can be used to control operation of a transfer device, e.g., a robotic arm, within the incubator cabinet to ensure that the transfer device can grab, manipulate or maneuver devices or items appropriately within the incubator cabinet.

In some embodiments, before containers or vessels are brought into an incubator cabinet, a user can select an automation system protocol based on the particular containers, vessels, ingredients, or cells that are being inserted into the incubator cabinet. Relevant information related to the incubator and/or one or more incubator components, and the cells being grown can be entered into a data system. For example, one or more identifiers such as barcodes (e.g., 1D or 2D barcodes) can be placed on the container or vessel, and other significant information, such as, the type of container, the contents of the container, what assays or manipulations are to be performed on the sample in the container can be specified. In some embodiments, information related to the incubator system and/or cells can be contained in one or more barcodes, on a separate data system, or a combination thereof. The user may also enter information that identifies the dimensionality (e.g., height, diameter) of the vessel or other container or the system itself can be configured to determine the height or other dimensions of the vessel or other container. Using this information, the robotic arm may be requested to transport a particular container, such as when an analytical module is ready to perform an assay or other manipulation on cells grown in the vessels or has completed performing an assay or manipulation.

The incubators provided herein include several components, including sensors, environmental control systems, robotics, etc. which may operate together at the direction of a computer, processor, microcontroller or other controller. The components may include, for example, a transfer device (e.g., robotic arm), a liquid handling devices, a delivery system for delivering culture vessels, or other components to or from the incubator cabinet, an environmental control system for controlling the temperature and other environmental aspects of the incubator cabinet, a door operation system, an imaging or detection system, and a cell culture assay system.

In some cases, operations such as controlling operations of a cell culture incubator and/or components provided therein or interfacing therewith may be implemented using hardware, software, or a combination thereof. When implemented in software, the software code can be executed on any suitable processor or collection of processors, whether provided in a single component or distributed among multiple components. Such processors may be implemented as integrated circuits, with one or more processors in an integrated circuit component. A processor may be implemented using circuitry in any suitable format.

A computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable, mobile or fixed electronic device, including the incubator itself.

In some cases, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. In other examples, a computer may receive input information through speech recognition or in other audible format, through visible gestures, through haptic input (e.g., including vibrations, tactile and/or other forces), or any combination thereof.

One or more computers may be interconnected by one or more networks in any suitable form, including as a local area network or a wide area network, such as an enterprise network or the Internet. Such networks may be based on any suitable technology and may operate according to any suitable protocol and may include wireless networks, wired networks, or fiber optic networks.

The various methods or processes outlined herein may be coded as software that is executable on one or more processors that employ any one of a variety of operating systems or platforms. Such software may be written using any of a number of suitable programming languages and/or programming or scripting tools, and may be compiled as executable machine language code or intermediate code that is executed on a framework or virtual machine.

One or more algorithms for controlling methods or processes provided herein may be embodied as a readable storage medium (or multiple readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible storage medium) encoded with one or more programs that, when executed on one or more computers or other processors, perform methods that implement the various methods or processes described herein.

In some embodiments, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the methods or processes described herein.

As used herein, the term "computer-readable storage medium" encompasses only a computer-readable medium that can be considered to be a manufacture (e.g., article of manufacture) or a machine. Alternatively or additionally, methods or processes described herein may be embodied as a computer readable medium other than a computer-readable storage medium, such as a propagating signal.

The terms "program" or "software" are used herein in a generic sense to refer to any type of code or set of executable instructions that can be employed to program a computer or other processor to implement various aspects of the methods or processes described herein. Additionally, it should be appreciated that according to one aspect of this embodiment, one or more programs that when executed perform a method or process described herein need not reside on a single computer or processor, but may be distributed in a modular fashion amongst a number of different computers or processors to implement various procedures or operations.

Executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. Non-limiting examples of data storage include structured, unstructured, localized, distributed, short-term and/or long-term storage. Non-limiting examples of protocols that can be used for communicating data include proprietary and/or industry standard protocols (e.g., HTTP, HTML, XML, JSON, SQL, web services, text, spreadsheets, etc., or any combination thereof). For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

In some embodiments, information related to the operation of the incubator (e.g., temperature, humidity, gas composition, images, cell culture conditions, etc., or any combination thereof) can be obtained from one or more sensors associated with the incubator (e.g., located within the incubator cabinet, or located within the incubator but outside the incubator cabinet), and can be stored in computer-readable media to provide information about conditions during a cell culture incubation. In some embodiments, the readable media comprises a database. In some embodiments, said database contains data from a single incubator. In some embodiments, said database contains data from a plurality of incubators. In some embodiments, data is stored in a manner that makes it tamper-proof. In some embodiments, all data generated by the instrument (e.g., an incubator) is stored. In some embodiments, a subset of data is stored.

In some embodiments, the component (e.g., a computer) controls various processes performed inside the incubator. For example, a computer may direct control equipment (e.g., a manipulator, an imager, a fluid handling system, etc.). In some embodiments, the computer controls imaging of cell cultures, picking of cells, weeding of cells (e.g., removal of cell clumps), monitoring of cell culture conditions, adjustment of cell culture conditions, tracking of cell culture vessel movement within the incubator, and/or scheduling of any of the foregoing processes.

Turning to the figures, FIG. 1 depicts one illustrative embodiment of a cell culture incubator 1. The cell culture incubator includes an incubator cabinet 10 having a transfer chamber 20 and an internal chamber 30. An external door 12 opens and closes to permit communication between the transfer chamber 20 and the external environment (e.g. the environment external to the incubator cabinet 10). A transfer chamber door 14 opens and closes to permit communication between the transfer chamber 20 and the internal chamber 30.

The transfer chamber 20 and/or the internal chamber 30 may include one or more sensors for determining various internal conditions such as, but not limited to, temperature, humidity, gas content, pressure, and light levels. The transfer chamber 20 and/or the internal chamber 30 may include components for adjusting such internal conditions, such as a heater, humidifier, gas generator, air pump, etc.

In some embodiments, a transfer device is positioned within the internal chamber 30. In other embodiments, the transfer device is positioned within the transfer chamber 20.

In yet other embodiments, the transfer device is positioned in both the transfer chamber and the internal chamber. In other embodiments, the transfer device can freely move between the chambers (such as with a robot that can move between the chambers).

In the illustrative embodiment shown in FIG. 1, a transfer device 50 moves one or more items between the transfer chamber 20 and the internal chamber 30. The transfer device 50 may reach into transfer chamber 20, pick up one or more items from the transfer chamber 20, and move the item(s) into the internal chamber 30. The transfer device 50 may be a robotic arm or any other suitable transfer device described herein.

Figure 8:
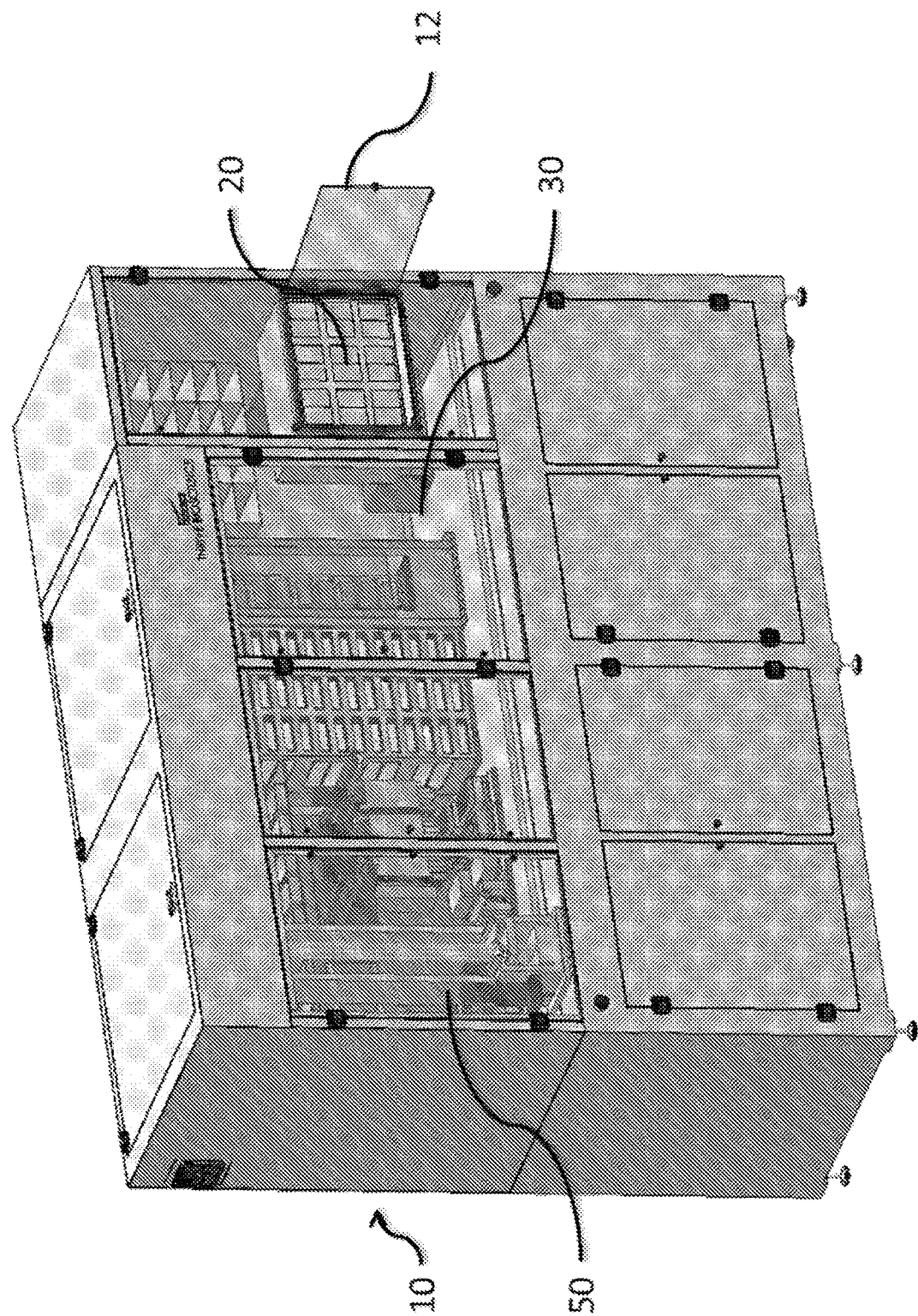
FIG. 8 is a schematic of an illustrative embodiment of a cell culture incubator having an incubator cabinet with a transfer chamber and an internal chamber according to one embodiment.

In an additional illustrative embodiment shown in FIG. 8, a transfer device 50 moves one or more items between the transfer chamber 20 and the internal chamber 30. The transfer device 50 may reach into transfer chamber 20, pick up one or more items from the transfer chamber 20, and move the item(s) into the internal chamber 30. The transfer device 50 may be a robotic arm or any other suitable transfer device described herein.

Figure 2:
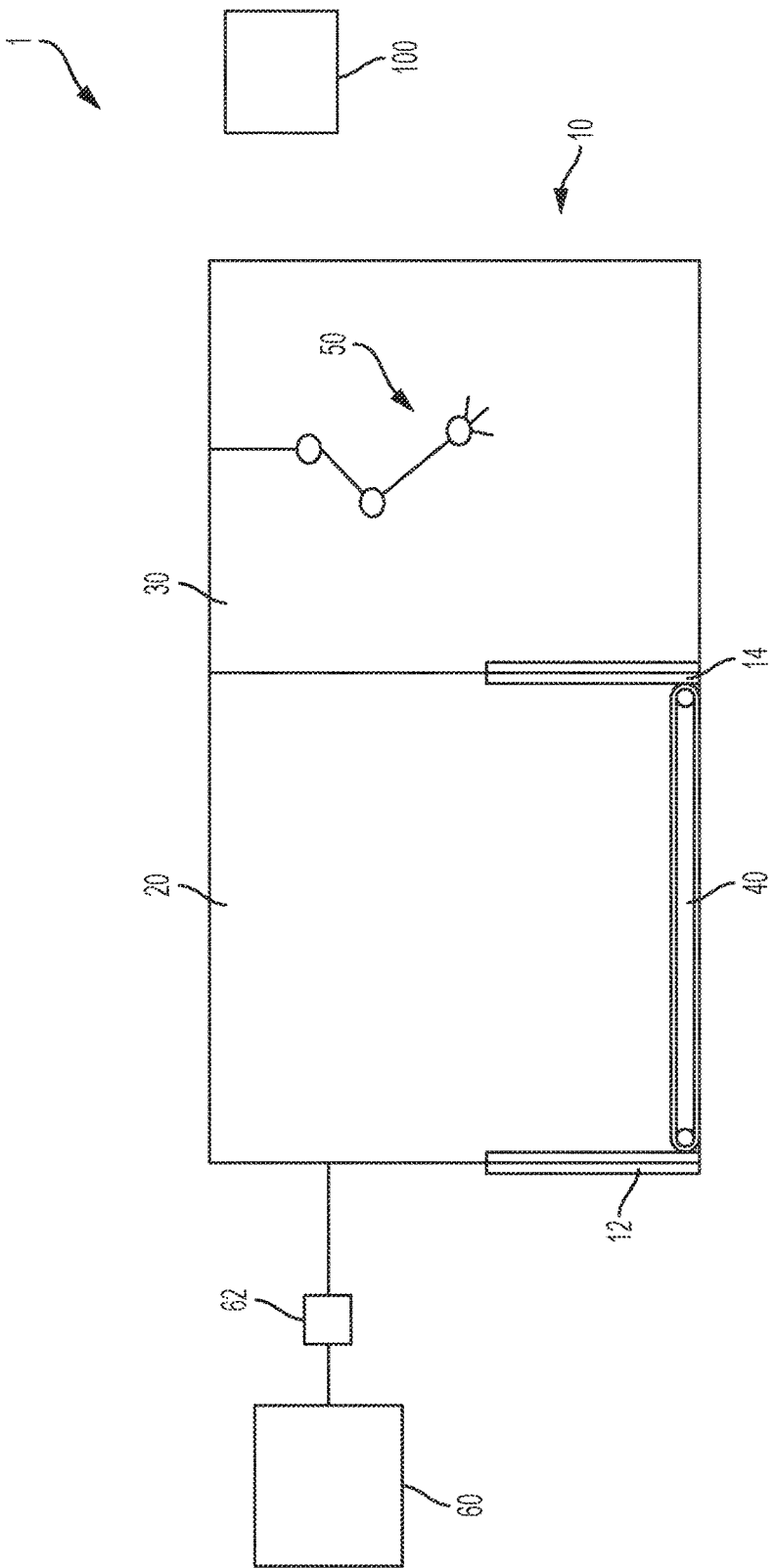
FIG. 2 is a schematic of an illustrative embodiment of a cell culture incubator having a transfer device in a transfer chamber according to one embodiment.

In some embodiments, more than one transfer device may be included in the cell culture incubator cabinet. In the illustrative embodiment shown in FIG. 2, in addition to the transfer device 50 of the internal chamber 30, a transfer device 40 is included in the transfer chamber 20. The transfer device 40 is a belt conveyor system that conveys items from one end of the transfer chamber 20 to the other end of the transfer chamber 20. As one illustrative example, a user opens external door 12 and places an item on the transfer device 40. The transfer device 40 conveys the item towards transfer chamber door 14, which opens to receive the item. A robotic arm 50 of the internal chamber 30 may move the item off the transfer device 40 and move the item to an appropriate location in the internal chamber 30. Alternatively, the item falls off the conveyor 40 as it approaches the end of the conveyor and lands in internal chamber 30. The item may be moved within the internal chamber 30 by a robotic arm 50 or other transfer device.

In some embodiments, one or more components in an incubator cabinet and/or one a transfer device may be used to locate and/or align the transfer device. In some embodiments, a location or alignment component may be a physical feature (e.g., one or more protrusions, indentations, guides, etc., or any combination thereof). In some embodiments, a location or alignment component may be a signal and/or sensor (e.g., a laser, a camera, an ultrasonic range finder, etc., or any combination thereof).

It should be appreciated that other types of transfer devices may be used as part of the cell culture incubator. In one illustrative embodiment shown in FIG. 5, the cell culture incubator 1 includes a transfer device 70 that includes a linearly actuated receptacle. As shown in more detail in FIG. 6, the transfer device 70 includes a housing 76 and a receptacle 78 that is translated through housing 76 via an actuator 79. The actuator 79 moves the receptacle 78 from the first end 71 of the device to the second end 73 of the device. The receptacle 78 can extend at least partially through a first opening 72 at the first end 71 of the transfer device 70 and through a second hole 74 at the second end 73 of the device.

Figure 5:
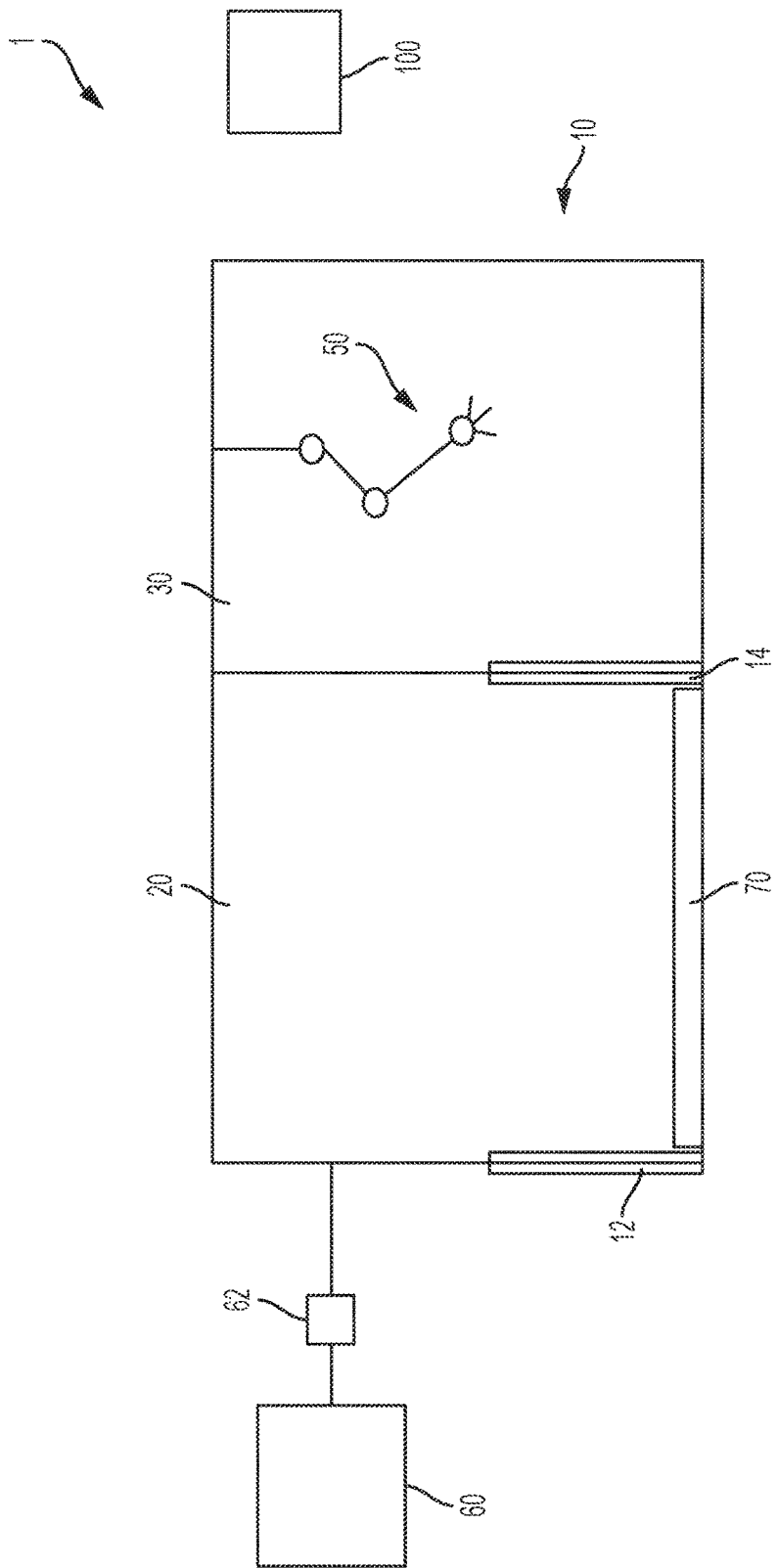
FIG. 5 is a schematic of an illustrative embodiment of a cell culture incubator having a linearly translating transfer device according to one embodiment.
Figure 6:
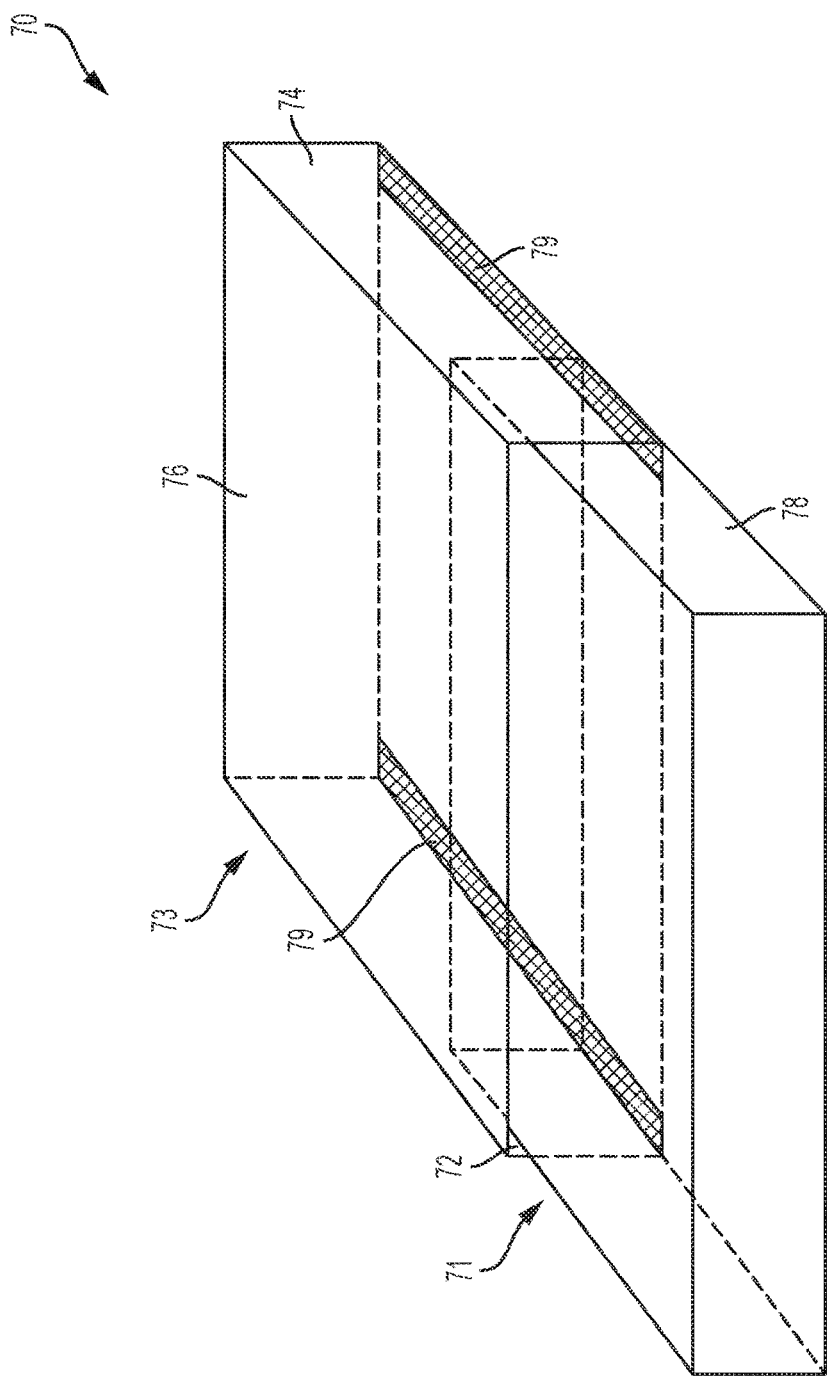
FIG. 6 is a perspective view of the transfer device shown in FIG. 5.

One illustrative example involving an operation of transfer device 70 will now be discussed in reference to FIGS. 5-6. First, a user opens the external door 12. The actuator 79 of the transfer device 70 moves receptacle 78 out through the first opening 72 so that a user can place one or more items into the receptacle 78. The user places any desired items into the receptacle 78 through an open top or through an opening of the receptacle. A user may then indicate to the transfer device 70 that all desired items have been placed into the receptacle 78 by pushing a button, pushing the receptacle 78 toward the second end 73, or otherwise providing a signal to the transfer device 70. The actuator 79 then moves the receptacle 78 back into the housing 76 toward the second end 73. Once the receptacle 78 has been retracted into the housing 76, the external door 12 is closed. Once the external door 12 is closed, and any appropriate sterilization and/or condition equilibration processes inside transfer chamber 20 are completed, the internal door 14 is opened. The actuator 79 of the transfer device 70 moves the receptacle 78 at least partially through the second opening 74. In some cases, the receptacle 78 may be moved at least partially into the internal chamber 30. The transfer device 50 of the internal chamber picks up the item(s) in the receptacle 78 and places the item(s) in an appropriate location in the internal chamber 30.

Figure 7:
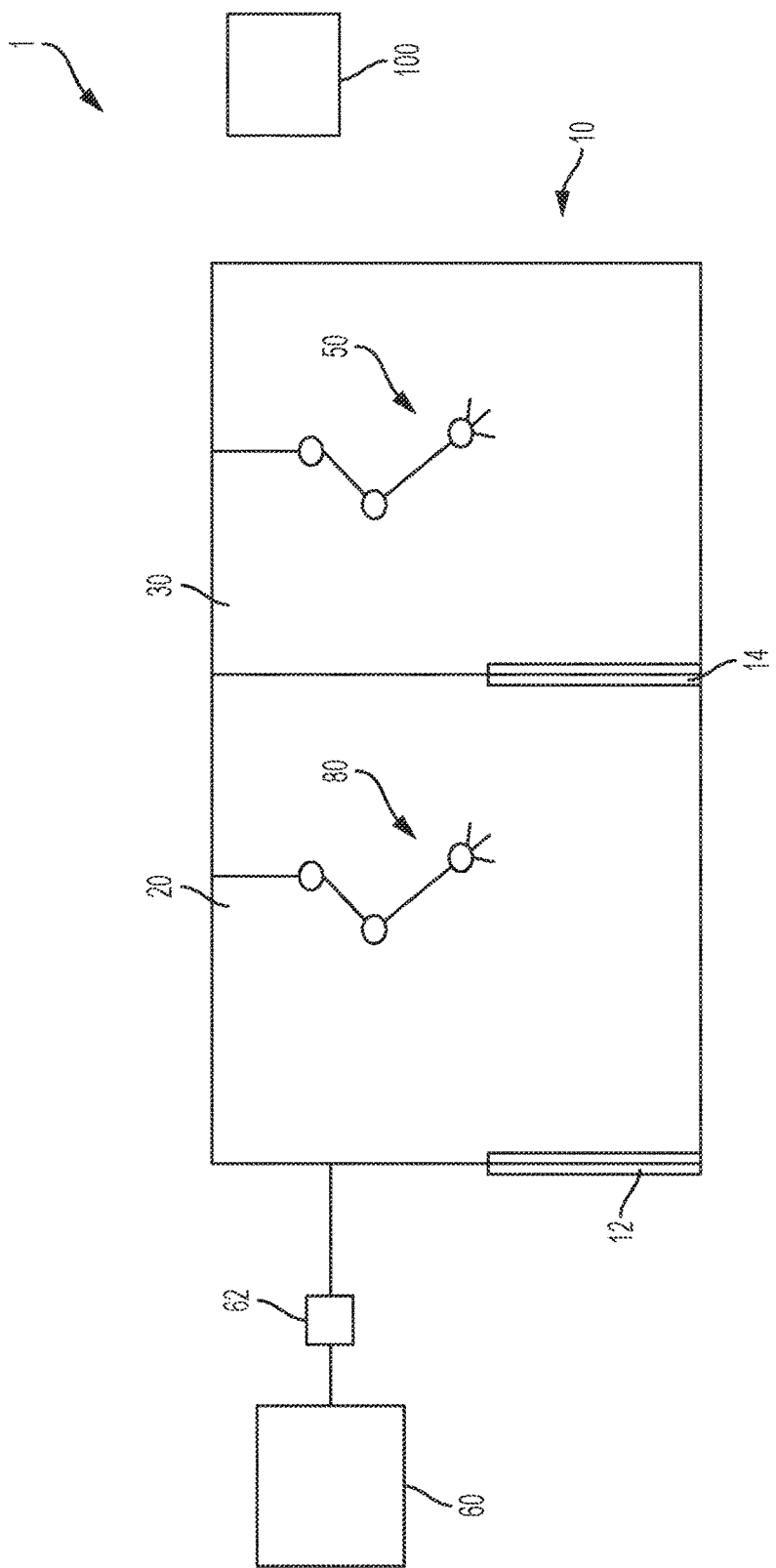
FIG. 7 is a schematic of an illustrative embodiment of a cell culture incubator having a robotic arm in the transfer chamber according to one embodiment.

In yet another illustrative embodiment, shown in FIG. 7, the transfer chamber 20 includes a transfer device 80 that is a robotic arm type transfer device. It should be appreciated that any number and any type of transfer devices may be included in an incubator (e.g., within one or more chambers of an incubator cabinet).

As described herein, a sterilization process may occur within transfer chamber 20 to sterilize any items added into the transfer chamber 20 from the external environment. In one embodiment, a sterilization medium is used as part of the sterilization process. As seen in FIG. 1, a sterilization medium source 60 is in fluid communication with the transfer chamber 20. A pump 62 may be used to convey sterilization medium from the sterilization medium source 60 to the transfer chamber 20. Alternatively or in addition, the pump 62 may move sterilization medium from the transfer chamber 20 to the sterilization medium source 60. It should be appreciated that pump 62 may be integrated with the source 60 itself. In some embodiments, no pump is included at all.

In one embodiment, the sterilization medium used is ozone. However, it should be appreciated that other types of sterilization medium and corresponding source may be used other than ozone. As such, sterilization medium source 60 may be a source of any suitable sterilization medium.

The sterilization medium provided to the transfer chamber may be used to sterilize the incubator cabinet or other parts of the incubator as part of a cleaning cycle. In one embodiment, during a cleaning cycle, sterilization medium provided by the source 60 is provided into the transfer chamber 20 to sterilize the chamber itself. The internal door 14 may remain closed to prohibit sterilization medium from entering internal chamber 30.

In another embodiment, both the transfer chamber 20 and the internal chamber 30 are sterilized. During a cleaning cycle, the internal door 14 may be opened while ozone gas or other sterilization medium is generated or provided from source 60. With the internal door 14 open, sterilization medium may enter into both transfer chamber 20 and internal chamber 30.

Figure 3:
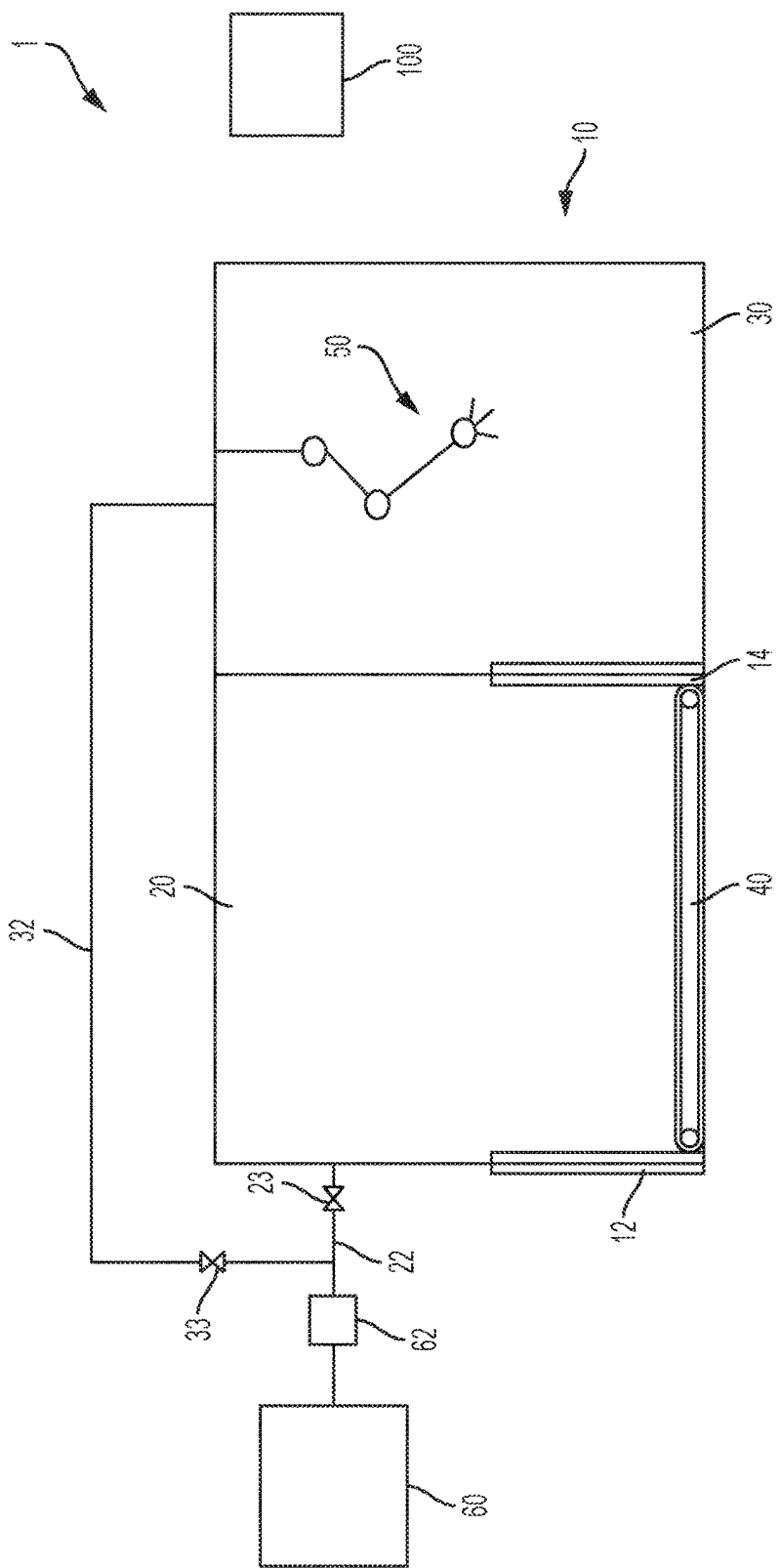
FIG. 3 is a schematic of an illustrative embodiment of a cell culture incubator having an ozone flow system according to one embodiment.

In one illustrative embodiment, shown in FIG. 3, sterilization medium may be directly routed to internal chamber 30. The sterilization medium flow path includes one or more flow controllers 23, 33 (such as valves) to control the sterilization medium flow path. Flow controller 23 controls flow through a transfer chamber path 22 and flow controller 33 controls flow through an internal chamber path 32. In one mode, where sterilization medium is desired only in the transfer chamber 20, flow controller 33 is closed while flow controller 23 is open, and the external door 12 and internal door 14 are closed. In another mode, where sterilization medium is desired only in the internal chamber, flow controller 23 is closed while flow controller 33 is open, and internal door 14 is closed. In yet another mode, where sterilization medium is desired in both chambers, both flow controllers 23, 33 are open while external door 12 is closed. Internal door 14 may be open or closed.

Figure 4:
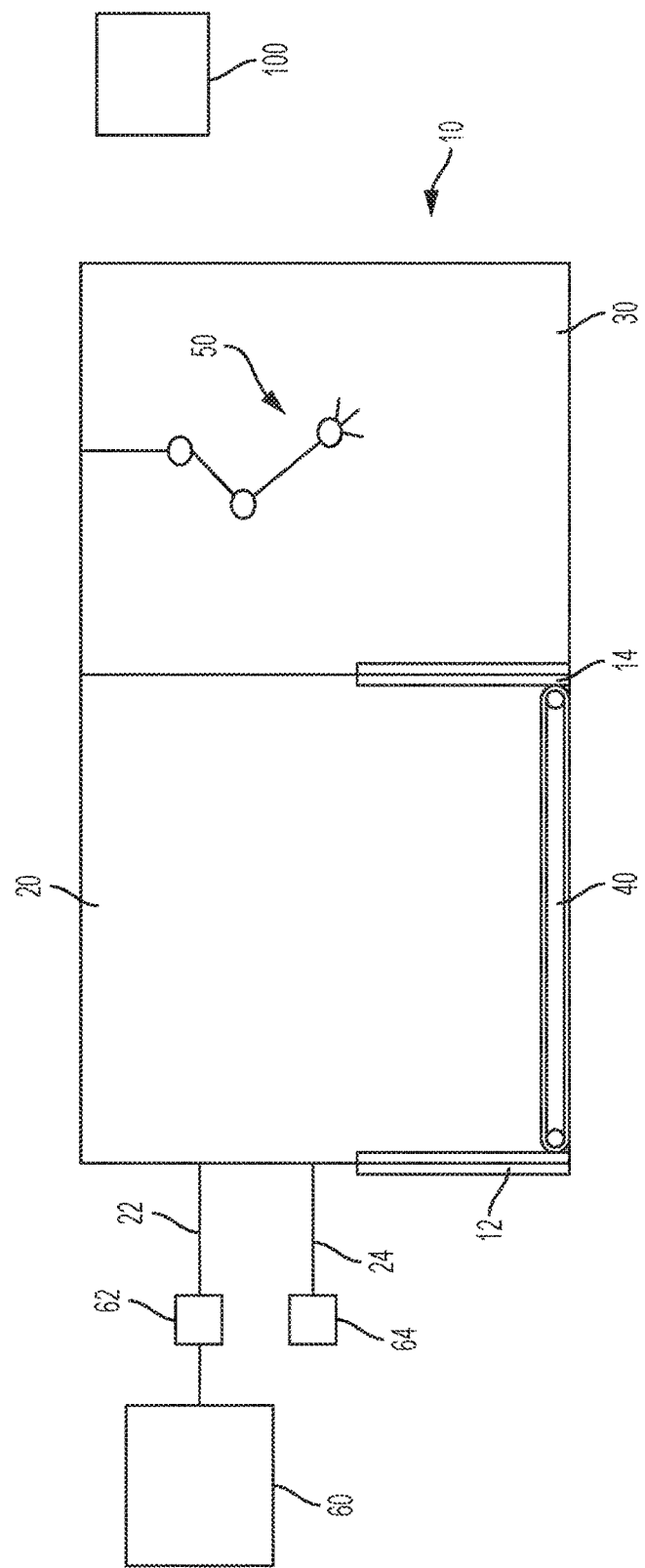
FIG. 4 is a schematic of an illustrative embodiment of a cell culture incubator having a second pump according to one embodiment.

In some embodiments, as seen in FIG. 4, a second pump 64 is included to remove ozone gas and/or other fluids from the transfer chamber 20 through an exit path 24.

Figure 9:
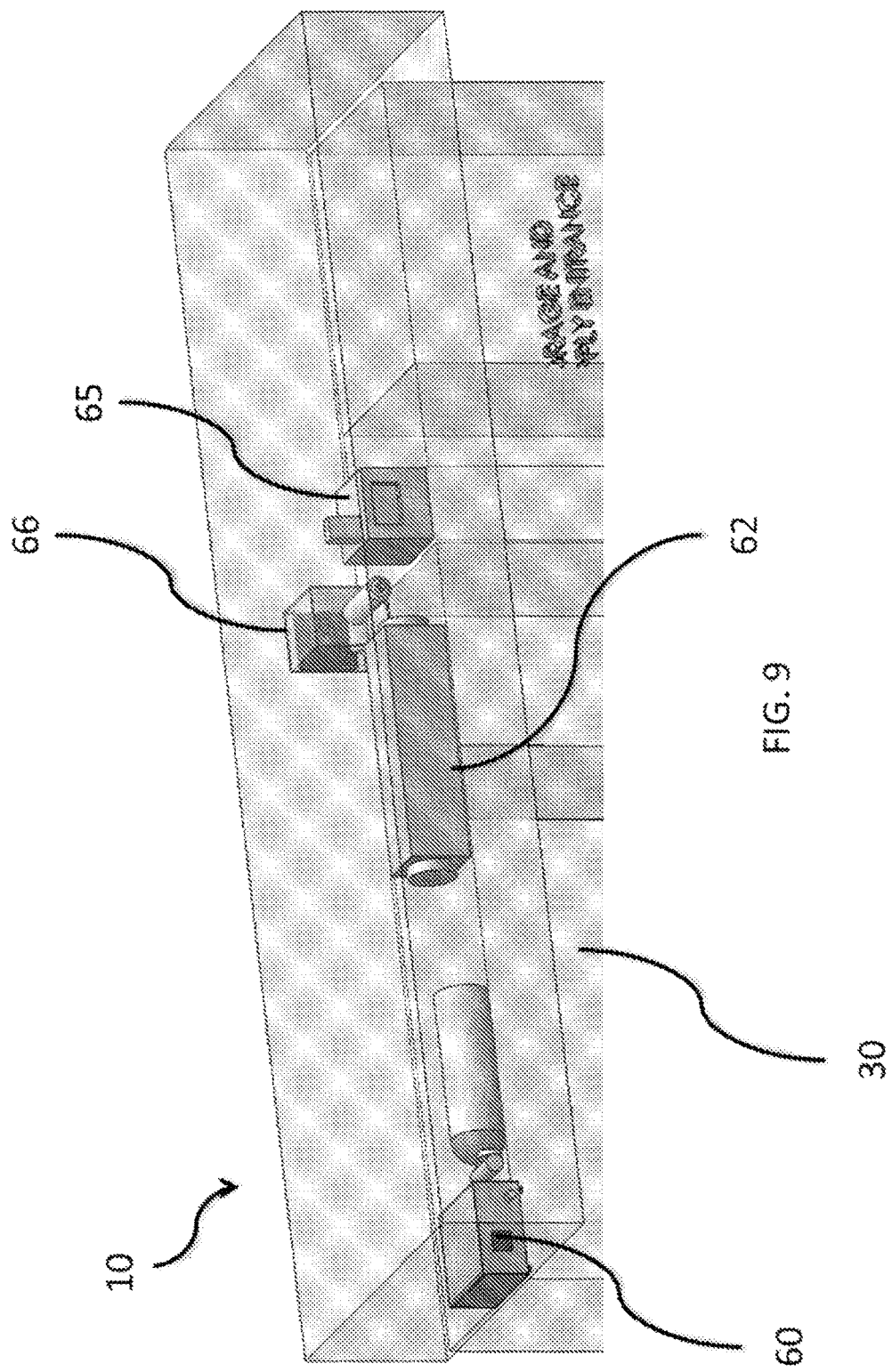
FIG. 9 is a schematic of an illustrative embodiment of a cell culture incubator having an ozone flow system according to one embodiment.

In one illustrative embodiment, shown in FIG. 9, sterilization medium may be directly routed to internal chamber 30. A pump 62 may be used to convey sterilization medium from the sterilization medium source 60 to the internal chamber 30. The controller may receive information from one or more sensors 65 located inside the incubator cabinet 10 (sensors may be in the transfer chamber 20 and/or the internal chamber 30), or from one or more sensors 66 located on the exterior of the incubator cabinet 10. The controller may communicate with one or more components of the cell culture incubator 1 and/or the sensors via wireless signals and/or wired signals.

In some embodiments, a controller 100 may be used to control one or more components of the cell culture incubator 1. For example, the controller 100 may control the sterilization medium source 60, pump 62 and/or 64, external door 12, internal door 14, transfer device 40, 50 and/or 70, sensors, and any components that affect the internal conditions of the incubator (e.g., heaters, humidifiers, gas generators, etc.). The controller 100 may be external to the incubator cabinet, as seen in FIG. 1. The controller may receive information from one or more sensors located inside the incubator cabinet 10 (sensors may be in the transfer chamber 20 and/or the internal chamber 30). The controller may communicate with one or more components of the cell culture incubator 1 and/or the sensors via wireless signals and/or wired signals.

Automated Cell Culture

Aspects of the disclosure relate to incubators and methods for culturing, manipulating, and/or monitoring cells under controlled conditions (e.g., under aseptic and/or sterile conditions). In some aspects, incubators and methods include automated components. In some aspects, incubators and methods are useful for long term cell culture (e.g., to grow and maintain cells for recombinant protein expression or to grow and/or differentiate cells for therapeutic applications such as implantation). In some embodiments, cell cultures are grown within a culture vessel in an incubator of the disclosure.

Culture Vessel

As used herein, a "cell culture vessel" is a device including a housing and one or more chambers for culturing cells. In some embodiments, the housing is a frame. The frame may be coupled to a lid. The one or more chambers may include cell culturing media including one or more membranes. In some embodiments, a cell culture vessel may include nutrients for promoting the growth of cells. In certain embodiments, a cell culture vessel may entirely enclose one or more cells or groups thereof. The housing of a cell culture vessel may include one or more pores or openings to permit the transfer of gases between a cell culture vessel and its surrounding environment. In certain embodiments, a cell culture vessel includes a transparent or optically clear window. For example, a lid coupled to the housing of a cell culture vessel may include an optically clear portion for viewing cells e.g., with a microscope or other imager. In some embodiments, a cell culture vessel includes one or more portions that are substantially non-reflective.

Cell culture vessels may be configured for culturing cells of different types, including eukaryotic or prokaryotic cells. In some embodiments, cells are mammalian cells (e.g., human cells, canine cells, bovine cells, ovine cells, feline cells, or rodent cells such as rabbit, mouse, or rat cells). In some embodiments, cells are insect cells, avian cells, microbial cells (e.g., yeast cells such as *Saccharomyces cerevisiae, Kluyveromyces lactis,* or *Pischia pastoris* cells, or bacterial cells such as *Escherichia coli, Bacillus subtilis,* or *Corynebacterium* cells), insect cells (e.g., *Drosophila* cells, or Sf9 or Sf21 cells), plant cells (e.g., algal cells) or cells of any other type.

In some embodiments, cell culture vessels may be pre-kitted with one or more reagents desired for a particular purpose, e.g., for growing cells, for differentiating cells, for subjecting cells to a particular assay condition, etc. In some embodiments, pre-kitted cell culture vessels contain reagents useful for performing a particular experiment (e.g., cell growth media, growth factors, selection agents, labeling agents, etc.) on a cell culture, in advance of the experiment. Pre-kitted cell culture vessels may facilitate experimental protocols by providing cell culture-ready vessels that do not require the addition of reagents. For example, progenitor cells from a patient may be added to a cell culture vessel pre-kitted with reagents for cell differentiation for the purpose of expanding a population of differentiated cells for autologous cell therapy. Pre-kitted cell culture vessels can be stored at any appropriate temperature, which is determined by the recommended storage parameters of the reagents within the pre-kitted cell culture vessel. In some embodiments, pre-kitted cell culture storage vessels are stored prior to use at temperatures between about −80 degrees C. and about 37 degrees C. In some embodiments, pre-kitted cell culture storage vessels are stored prior to use at temperatures between about −80 degrees C. and about −20 degrees C. In some embodiments, pre-kitted cell culture storage vessels are stored prior to use at temperatures between about −20 degrees C. and about 4 degrees C. In some embodiments, pre-kitted cell culture storage vessels are stored prior to use at temperatures between about 4 degrees C. and about 37 degrees C. In some embodiments, pre-kitted cell culture vessels are disposable. In some embodiments, pre-kitted cell culture vessels are reusable and/or refillable.

In some embodiments, cells are cultured for producing natural products (e.g., taxols, pigments, fatty acids, biofuels, etc.). In some embodiments, cells are cultured to express recombinant products (e.g., recombinant protein products such as antibodies, hormones, growth factors, or other therapeutic peptides or proteins). In some embodiments, cells are expanded and/or differentiated for therapeutic use such as implantation into a subject (e.g., a human subject) in order to provide or supplement a cellular, tissue, or organ function that is missing or defective in the subject.

In some embodiments, cells are from immortalized cell lines. Non-limiting examples of cell lines include human cells, for example, HeLa cells, prostate cancer cells (e.g., DU145, PC3 and/or Lncap cells), breast cancer cells (e.g., MCF-7, MDA-MB-438, and/or T47D cells), acute myeloid leukemia cells (e.g., THP-1 cells), glioblastoma cells (e.g., U87 cells), neuroblastoma cells (e.g., SHSY5Y cells), bone cancer cells (e.g., Saos-2 cells), and chronic myelogenous leukemia cells (e.g., KBM-7 cells). In some embodiments, cell lines include primate cell lines, rodent cell lines (e.g., rat or mouse cell lines), canine cell lines, feline cell lines, Zebrafish cell lines, *Xenopus* cell lines, plant cell lines, or any other cell lines. In some embodiments, cells are human 293 cells (e.g., 293-T or HEK 293 cells), murine 3T3 cells, Chinese hamster ovary (CHO) cells, CML T1 cells, or Jurkat cells.

In some embodiments, cells are primary cells, feeder cells, or stem cells. In some embodiments, cells are isolated from a subject (e.g., a human subject). In some embodiments, cells are primary cells isolated from a tissue or a biopsy sample. In some embodiments, cells are hematopoietic cells. In some embodiments, cells are stem cells, e.g., embryonic stem cells, mesenchymal stem cells, cancer stem cells, etc. In some embodiments, cells are isolated from a tissue or organ (e.g., a human tissue or organ), including but not limited to, solid tissues and organs. In some embodiments, cells can be isolated from placenta, umbilical cord, bone marrow, liver, blood, including cord blood, or any other suitable tissue. In some embodiments, patient-specific cells are isolated from a patient for culture (e.g., for cell expansion and optionally differentiation) and subsequent re-implantation into the same patient or into a different patient. Accordingly, in some embodiments, cells grown in the incubators disclosed herein may be used for allogenic or autogeneic therapy. In some embodiments, cells grown in the incubators disclosed herein may be genetically modified, expanded and reintroduced into a patient for the purpose of providing an immunotherapy (e.g., chimeric antigen receptor therapy (CAR-T), or delivery of CRISPR/Cas modified cells).

In some embodiments, a primary cell culture includes epithelial cells (e.g., corneal epithelial cells, mammary epithelial cells, etc.), fibroblasts, myoblasts (e.g., human skeletal myoblasts), keratinocytes, endothelial cells (e.g., microvascular endothelial cells), neural cells, smooth muscle cells, hematopoietic cells, placental cells, or a combination of two or more thereof.

In some embodiments, cells are recombinant cells (e.g., hybridoma cells or cells that express one or more recombinant products). In some embodiments, cells are infected with one or more viruses.

Primary Cell Isolation

In some embodiments, cells are isolated from tissues or biological samples for ex vivo culture in the incubators provided herein. In some embodiments, cells (e.g., white blood cells) are isolated from blood. In some embodiments, cells are released from tissues or biological samples using physical and/or enzymatic disruption. In some embodiments, one or more enzymes such as collagenase, trypsin, or pronase are used to digest the extracellular matrix. In some embodiments, tissue or biological samples are placed in culture medium (e.g., with or without physical or enzymatic disruption), and cells that are released and that grow in the culture medium can be isolated for further culture.

Cell Culture

As used herein, cell culture refers to a procedure for maintaining and/or growing cells under controlled conditions (e.g., ex vivo). In some embodiments, cells are cultured under conditions to promote cell growth and replication, conditions to promote expression of a recombinant product, conditions to promote differentiation (e.g., into one or more tissue specific cell types), or a combination of two or more thereof.

In some embodiments, cell culture vessels are configured for culturing cells in suspension. In some embodiments, cell culture vessels are configured for culturing adherent cells. In some embodiments, cell culture vessels are configured for 2D or 3D cell culture. In some embodiments, cell culture vessels include one or more surfaces or micro-carriers to support cell growth. In some embodiments, these are coated with extracellular matrix components (e.g., collagen, fibrin, and/or laminin components) to increase adhesion properties and provide other signals needed for growth and differentiation. In some embodiments, cell culture vessels include one or more synthetic hydrogels such as polyacrylamide or polyethylene glycol (PEG) gels to support cell growth. In some embodiments, cell culture vessels include a solid support with embedded nutrients (e.g., a gel or agar, for example, for certain bacterial or yeast cultures). In some embodiments, cell culture vessels include a liquid culture medium.

In some embodiments, cells are cultured in one of any suitable culture media. Different culture media having different ranges of pH, glucose concentration, growth factors, and other supplements can be used for different cell types or for different applications. In some embodiments, custom cell culture media or commercially available cell culture media such as Dulbecco's Modified Eagle Medium, Minimum Essential Medium, RPMI medium, HA or HAT medium, or other media available from Life Technologies or other commercial sources can be used. In some embodiments, cell culture media include serum (e.g., fetal bovine serum, bovine calf serum, equine serum, porcine serum, or other serum). In some embodiments, cell culture media are serum-free. In some embodiments, cell culture media include human platelet lysate (hPL). In some embodiments, cell culture media include one or more antibiotics (e.g., actinomycin D, ampicillin, carbenicillin, cefotaxime, fosmidomycin, gentamycin, kanamycin, neomycin, penicillin, penicillin streptomycin, polymyxin B, streptomycin, tetracycline, or any other suitable antibiotic or any combination of two or more thereof). In some embodiments, cell culture media include one or more salts (e.g., balanced salts, calcium chloride, sodium chloride, potassium chloride, magnesium chloride, etc.). In some embodiments, cell culture media include sodium bicarbonate. In some embodiments, cell culture media include one or more buffers (e.g., HEPES or other suitable buffer). In some embodiments, one or more supplements are included. Non-limiting examples of supplements include reducing agents (e.g., 2-mercaptoethanol), amino acids, cholesterol supplements, vitamins, transferrin, surfactants (e.g., non-ionic surfactants), CHO supplements, primary cell supplements, yeast solutions, or any combination of two or more thereof. In some embodiments, one or more growth or differentiation factors are added to cell culture media. Growth or differentiation factors (e.g., WNT-family proteins, BMP-family proteins, IGF-family proteins, etc.) can be added individually or in combination, e.g., as a differentiation cocktail comprising different factors that bring about differentiation toward a particular lineage. Growth or differentiation factors and other aspects of a liquid media can be added using automated liquid handlers integrated as part of an incubator provided herein.

In some aspects, the incubators and methods described herein provide and maintain appropriate temperature, and gas mixtures for cell growth. It should be appreciated that cell growth conditions differ for different cell types and that the incubators described herein can be programmed to maintain different conditions. In some embodiments, conditions of approximately 37 degrees C., and 5% $CO_2$ are used for mammalian cells.

In some embodiments, the incubators and methods described herein are used to monitor or assay the culture media for nutrient depletion, changes in pH, changes in temperature, accumulation of apoptotic or necrotic cells, and/or cell density. In some embodiments, the incubators and methods described herein are used to modify or change the culture media or conditions and/or to passage the cell cultures when appropriate. In some embodiments, these procedures are automated.

In some embodiments (e.g., for adherent cell cultures), culture media can be removed directly by aspiration and replaced with fresh media. In some embodiments (e.g., for non-adherent/suspension cultures), media changes can involve centrifuging a cell culture, removing the old culture media and replacing it with fresh media. In some embodiments, the centrifuge is located in the internal chamber of an incubator. In some embodiments, culture vessels allow for continuous media replacement. In some embodiments, the incubators described herein may include one or more components that can be used to process, replace, supply, and/or maintain different aspects of a culture media to support cells. Incubators may include a reservoir containing waste media and/or a reservoir containing fresh media. Such reservoirs may be present (e.g., for temporary storage) within a refrigerator inside the incubator or a refrigerated section of the incubator. In some embodiments, one or more reservoirs are provided outside the incubators and piping is provided into and out from the incubator space to supply or draw from a liquid handler units (e.g., liquid handle units having an aspirator) or temporary reservoir within the incubator to facilitate cells feeding, media changes, and other related needs. For suspension cells, devices may be provided within the incubator to separate cells from waste media (e.g., centrifuge(s) to facilitate cell pelleting) to facilitate automated media changes as part of an incubator provided herein. In some embodiments, the document provides a system comprising a cell culture incubator connected to a computer, capable of automatically monitoring and adjusting cell culture conditions for optimal growth of the cell culture.

In some embodiments, cells are passaged within an incubator cabinet described herein. In some embodiments, a cell culture is split and a subset of the cell culture is transferred to a fresh culture vessel for further growth. In some embodiments (e.g., for adherent cell cultures), cells are detached (e.g., mechanically, for example using gentle scraping, and/or enzymatically, for example, using trypsin-EDTA or one or more other enzymes) from a surface prior to being transferred to a fresh culture vessel. In some embodiments (e.g., for suspension cell cultures), a small volume of a cell culture is transferred to a fresh culture vessel.

In some embodiments, cell cultures are manipulated in other ways during culture within an incubator cabinet of an incubator provided herein. For example, cell cultures may be transfected with nucleic acids (e.g., DNA or RNA) or exposed to viral infection (e.g., using recombinant virus particles to deliver DNA or RNA).

Aseptic techniques can be used to prevent or minimize contamination of cell cultures during growth and manipulation. In some embodiments, equipment (e.g., pipettes, fluid handling devices, manipulating devices, other automated or robotic devices, etc.) that is used for cell culture is sterilized using an appropriate technique. Non-limiting techniques include heat exposure (e.g., autoclaving), surface disinfection (e.g., using alcohol, bleach, or other disinfectant), irradiation, and/or exposure to a disinfectant gas (e.g., ozone, hydrogen peroxide, etc.) as described herein. In some embodiments, media is sterilized using an appropriate technique. Non-limiting techniques include heat exposure (e.g., autoclaving), antimicrobial/antiviral treatment, filtration, and/or irradiation.

In some embodiments, manipulations of cell cultures are performed under aseptic conditions, for example, in an environment (e.g., within an incubator chamber) that has been disinfected and in which the air has been filtered to remove potential contaminants.

In some embodiments, cell cultures are grown and maintained under GMP-compliant conditions, including those that include using GMP-compliant media or GMP-compliant liquid handling equipment. In some cases, cell cultures are grown and maintained by performing methods in conjunction with standard operation procedures (SOPs).

In some embodiments, cell cultures can be monitored and/or evaluated to detect contamination. In some embodiments, contamination by cells from a different type of organism can be detected. In some embodiments, contamination of a mammalian cell culture by *mycoplasma*, bacteria, yeast, or viruses can be detected using any suitable technique. In some embodiments, cell culture contamination can be detected by assaying for changes or for rates of change of one or more culture properties such as pH, turbidity, etc., that are characteristic of contamination (e.g., by bacteria or yeast) and not characteristic of the cells (e.g., mammalian cells) being grown in culture. In some embodiments, one or more molecular detection assays (e.g., PCR, ELISA, RNA labeling or other enzymatic techniques) or cell-based assays can be used to detect contamination (e.g., *mycoplasma*, bacterial, yeast, viral, or other contamination).

In some embodiments, cell cultures can be monitored and/or evaluated to detect contamination with cells of similar types (e.g., a human cell line contaminated by different human cells or by different mammalian cells). In some embodiments, cell cultures and their potential contamination can be evaluated using DNA sequencing or DNA fingerprinting (e.g., short tandem repeat—STR—fingerprinting), isoenzyme analysis, human lymphocyte antigen (HLA) typing, chromosomal analysis, karyotyping, cell morphology, or other.

In some embodiments, cells produced using the incubators or methods described herein can be frozen to preserve them for later use and/or for transport. In some embodiments, cells are mixed with a cryopreservation composition after growth and/or differentiation and prior to freezing. A cryopreservation composition can be added to a cell culture vessel or cells can be transferred from a cell culture vessel to a cryopreservation vessel along with a cryopreservation composition. Non-limiting examples of cryoprotectants that can be included in a cryopreservation composition include DMSO, glycerol, PEG, sucrose, trehalose, and dextrose. In some embodiments, a freezer may be provided as a component of an incubator to facilitate freezing of cells isolated from cell cultures. For example, one or more freezers may be located in an internal chamber and/or integrated into the incubator cabinet (e.g., into a wall of the incubator cabinet).

Cell Culture Incubators

This embodiment relates to incubator and methods for culturing, manipulating, and/or monitoring cells under controlled conditions (e.g., under aseptic and/or sterile conditions). In some embodiments, the cell culture incubators provided herein include an incubator cabinet defining an internal chamber for incubation of cells in one or more cell culture vessels, in which the internal chamber is configured to hold the one or more cell culture vessels. In some cases, in addition to an internal door from the transfer chamber to the internal chamber, the incubators include at least one external door (e.g., 1, 2, 3, 4, or more external doors) opening from an external environment directly to the internal chamber, for example, to provide alternative access to the internal chamber during periods of time when the incubator is not operational, e.g., during maintenance of the incubator. In some embodiments, the incubators include a storage location within the internal chamber for storing one or more cell culture vessels.

As used herein, an "incubator cabinet" is a housing that includes one or more chambers configured to hold one or more cell culture vessels. In some embodiments, an incubator cabinet includes a transfer chamber and an internal chamber, one or both of which are configured to hold one or more cell culture vessels. In some embodiments, an incubator may include one or more other elements such as one or more gas sources (e.g., a gas cylinder or ozone generator), tubing (e.g., to convey one or more liquids or gases such as water, distilled water, deionized water, cell culture medium, air, carbon dioxide, ozone, and oxygen), airflow mechanisms (e.g., valves, release valves, pinholes, gas regulators, and mass flow regulators), pressure mechanisms (e.g., a pump such as a dry scroll pump, rotary pump, momentum transfer pump, diffusion pump, or diaphragm pump; a suction tube; a vacuum system; and an air blower), environmental monitors and controls (e.g., a gas sensor and/or monitor to sense and/or control concentrations of gases such as carbon dioxide, oxygen, and ozone; heat sources or sinks; temperature monitors and controls; humidity monitors; gas scrubbers; air filters; instrumentation for measuring particulate matter; pressure gauges; and flow meters), doors (e.g., openings or panels) windows (e.g., optical windows made of glass, plastic, composite, or other substantially transparent material for viewing an area inside the incubator), ports (e.g., to permit the introduction or removal of one or more gases or liquids), light sources (e.g., lamps, bulbs, lasers, and diodes), optical elements (e.g., microscope objectives, mirrors, lenses, filters, apertures, wave plates, windows, polarizers, fibers, beam splitters, and beam combiners), imaging elements (e.g., cameras, barcode readers), electrical elements (e.g., circuits, cables, power cords, and power supplies such as batteries, generators, and direct or alternating current supplies), computers, mechanical elements (e.g., motors, wheels, gears, robotic elements, and actuators such as pneumatic actuators, electromagnetic actuators, motors with cams, piezoelectric actuators, and motors with lead screws), and control elements (e.g., spin-wheels, buttons, keys, toggles, switches, cursors, screws, dials, screens, and touch-screens). In some embodiments, one or more of these other elements are part of the incubator but are external to the incubator cabinet. In some embodiments, one or more of these other elements are included within the incubator cabinet.

In some embodiments, incubators or incubator cabinets provided herein are rectangularly cuboidal in shape. In some embodiments incubators or incubator cabinets provided herein have a rectangular footprint in a range of 1 sq. ft. to 16 sq. ft. In some embodiments incubators or incubator cabinets provided herein have a rectangular footprint of up to about 1 sq. ft., 2 sq. ft., 3 sq. ft., 4 sq. ft., 5 sq. ft., 6 sq. ft., 7 sq. ft., 8 sq. ft., 9 sq. ft., 10 sq. ft., 11 sq. ft., 12 sq. ft., 13 sq. ft., 14 sq. ft., 15 sq. ft., or 16 sq. ft. In some embodiments incubators or incubator cabinets provided herein have a total chamber volume in a range of 1 cu. ft. to 100 cu. ft. In some embodiments incubators or incubator cabinets provided herein have a chamber volume of up to about 1 cu. ft., 5 cu. ft., 10 cu. ft., 25 cu. ft., 50 cu. ft. or 100 cu. ft. In some embodiments incubators or incubator cabinets provided herein have a rectangular footprint in a range of 0.09 sq. m. to 1.78 sq. m. In some embodiments incubators or incubator cabinets provided herein have a rectangular footprint of up to about 0.1 sq. m., 0.2 sq. m., 0.3 sq. m., 0.4 sq. m., 0.5 sq. m., 0.6 sq. m., 0.7 sq. m., 0.8 sq. m., 0.9 sq. m., 1.0 sq. m., 1.1 sq. m., 1.2 sq. m., 1.3 sq. m., 1.4 sq. m., 1.5 sq. m., 1.6 sq. m., or 1.7 sq. m. In some embodiments, incubators or incubator cabinets provided herein have a total chamber volume in a range of 0.03 cu. m. to 3 cu. m. In some embodiments incubators or incubator cabinets provided herein have a chamber volume of up to about 0.03 cu. m., 0.1 cu. m., 0.3 cu. m., 1 cu. m. or 3 cu. m.

Storage Locations

As used herein, a "storage location" refers to a location at which one or more cell culture vessels is stored (e.g., within an incubator cabinet). For example, one or more cell culture vessels may be stored at a storage location and later transferred to a different location (e.g., an imaging location). The storage location may be disposed in the internal chamber of the incubator cabinet. A storage location may be configured for storing a plurality of cell culture vessels. For example, a storage location may include one or more storage arrays, racks, shelves, pigeon-holes, cubbies, trays, slots, or other positions or mechanisms. In some embodiments, a storage location may be configured to store cell culture vessels horizontally, while in other embodiments it may be configured to store cell culture vessels vertically. For example, a storage location may include a plurality of slots to receive cell culture vessels stacked vertically over one another. A storage location may be configured to hold 1, 2, 3, 4, 5, 6, 7, 8, 9, 10, 15, 20, 25, 30, 35, 40, 45, 50, 100, or any other number of cell culture vessels. In some embodiments, a storage location may be configured to hold greater than 100 cell culture vessels. In some embodiments, a storage location may include a mechanism for moving one or more storage arrays, racks, shelves, pigeon-holes, cubbies, trays, slots, or other positions or mechanisms. For example, a storage location may include one or more motors and movable stages (e.g., an xy or xyz stage) to move a storage rack from one position in an internal chamber to another position in an internal chamber, e.g., to facilitate access to one or more cell culture vessels stored in different locations. In some embodiments, the incubator cabinet may include one or more cell culture vessel transfer devices for moving one or more cell culture vessels.

A storage location may be configured to securely hold or receive one or more cell culture vessels. For example, one or more components of the storage location may include one or more locking mechanisms that have one or more adhesive, magnetic, electrical, and/or mechanical components (e.g., snaps, fasteners, locks, clasps, gaskets, o-rings, septa, springs, and other engagement members). In some embodiments, a storage location and/or cell culture vessel may include one or more grooves or depressions and/or may involve pieces of molded plastic. For example, a cell culture vessel may include one or more protruded features (e.g., a rim or knob) that is molded for insertion into one or more corresponding grooves, holes, or depressions at a storage location. In some cases, a cell culture vessel may include one or more grooves, holes, or depressions that are molded to fit one or more corresponding protruded features at a storage location.

As used herein, a "fiducial mark" refers to a feature that facilitates alignment of one or more components. In some embodiments, fiducial marks may include one or more hole apertures over a fluorescent media or printed or embossed fluorescent material. In other embodiments, fiducial marks may include grids, lines, or symbols. In some embodiments, one or more cell culture vessels include one or more fiducial marks to facilitate alignment of one or more cell culture vessels with an imager. In some embodiments, fiducial marks may be associated with moving parts, including transfer devices and robotics devices.

Materials

In some embodiments, an incubator cabinet is single-walled. In some embodiments, an incubator is double-walled. In some embodiments, insulation material is provided between the double walls of an incubator cabinet to control heat loss from the cabinet and facilitate temperature control in the cabinet. In some embodiments, the outer wall of an incubator cabinet includes a sheet metal, e.g., a 14-20 gauge cold rolled steel. In some embodiments, an inner wall (e.g., a chamber surface) of an incubator cabinet includes electro-polished stainless steel. In some embodiments, an inner wall (e.g., a chamber surface) of an incubator cabinet includes corrosion resistant materials, such as, titanium, cobalt-chrome, tantalum, platinum, zirconium, niobium, stainless steel, and alloys thereof. However, in some embodiments, a chamber surface of an incubator cabinet includes a polymeric material such as polytetrafluoroethylene (PTFE), or a polymeric material know under the trade name of Parylene. In some embodiments, a chamber surface may have anti-microbial properties, such as copper or silver or anti-microbial compounds incorporated into a polymeric surface coating.

Cell Assays

In certain embodiments, incubators provided herein are configured to permit one or more assays to be performed within an incubator cabinet or within a chamber operably connected to an incubator cabinet, e.g., a separate assay chamber that is part of the incubator. In some embodiments, incubators provided herein are configured to permit performance of a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, a nuclear fragmentation assay, or a combination thereof. Other exemplary assays include BrdU, EdU, or H3-thymidine incorporation assays; DNA content assays using a nucleic acid dye, such as Hoechst Dye, DAPI, actinomycin D, 7-aminoactinomycin D, or propidium iodide; cellular metabolism assays such as AlamarBlue, MTT, XTT, and CellTitre Glo; nuclear fragmentation assays; cytoplasmic histone associated DNA fragmentation assays; PARP cleavage assays; and, TUNEL staining assays.

Treatments and Experimental Interventions

In certain embodiments, incubators provided herein are configured to permit high-throughput screening (HTS) within an incubator cabinet. In some embodiments, HTS refers to testing of up to, for example, 100,000 compounds per day. In some embodiments, screening assays may be carried out in a multi-well format, for example, a 96-well, 384-well format, or 1,536-well format, and can be performed using automated protocols. In such high throughput assays, it is possible to screen several thousand different compounds or compositions in a single day. In particular, each well of a microtiter plate can be used to run a separate assay against a selected test compound, or, if concentration or incubation time effects are to be observed, a plurality of wells can contain test samples of a single compound. It is possible to assay many plates per day; assay screens for up to about 6,000, 20,000, 50,000, or more than 100,000 different compounds are possible using the assays. Typically, HTS implementations of the assays described herein involve the use of automation. In some embodiments, an integrated robot system that includes of one or more robotic arms transports assay microplates between multiple assay stations for compound, cell, and/or reagent addition, mixing, incubation, and finally readout or detection. In some aspects, an HTS assay may include preparing, incubating, and analyzing many plates simultaneously, further speeding the data-collection process.

In some embodiments, assays can include test cells, control cells, and one or more test compounds, e.g., 10, 100, 1000, 10,000, or more test compounds. The cells and test agents can be arranged in one or more vessels in a manner suitable for assessing effect of the test compound(s) on the cells. These assays can be performed within one or more incubator cabinets of one or more incubators described herein. Typically, the vessels contain a suitable tissue culture medium, and the test compounds are present in the tissue culture medium and may be delivered to the culture medium within an incubator cabinet of an incubator provided herein in an automated fashion. A medium appropriate for culturing a particular cell type can be selected for use. In some embodiments, a medium is free or essentially free of serum or tissue extracts, while in other embodiments such a component is present. In some embodiments, cells are cultured on a plastic or glass surface.

Microscopy

In some embodiments, an incubator provided herein is configured with a microscope or other imager for purposes of monitoring cell growth, viability or other aspect of cells. In some embodiments, the microscope or imager is used in conjunction with an assay performed within an incubator cabinet, such as an image based phenotypic screen or assay.

As used herein, an "imager" refers to an imaging device for measuring light (e.g., transmitted or scattered light), color, morphology, or other detectable parameters such as a number of elements or a combination thereof. An imager may also be referred to as an imaging device. In certain embodiments, an imager includes one or more lenses, fibers, cameras (e.g., a charge-coupled device or CMOS camera), apertures, mirrors, light sources (e.g., a laser or lamp), or other optical elements. An imager may be a microscope. In some embodiments, the imager is a bright-field microscope. In other embodiments, the imager is a holographic imager or microscope. In other embodiments, the imager is a fluorescence microscope.

As used herein, a "fluorescence microscope" refers to an imaging device which is able to detect light emitted from fluorescent markers present either within and/or on the surface of cells or other biological entities, said markers emitting light at a specific wavelength in response to the absorption a light of a different wavelength.

As used herein, a "bright-field microscope" is an imager that illuminates a sample and produces an image based on the light absorbed by the sample. Any appropriate bright-field microscope may be used in combination with an incubator provided herein.

As used herein, a "holographic imager" is an imager that provides information about an object (e.g., sample) by measuring both intensity and phase information of electromagnetic radiation (e.g., a wave front). For example, a holographic microscope measures both the light transmitted after passing through a sample as well as the interference pattern (e.g., phase information) obtained by combining the beam of light transmitted through the sample with a reference beam.

A holographic imager may also be a device that records, via one or more radiation detectors, the pattern of electromagnetic radiation, from a substantially coherent source, diffracted or scattered directly by the objects to be imaged, without interfering with a separate reference beam and with or without any refractive or reflective optical elements between the substantially coherent source and the radiation detector(s).

In some embodiments, an incubator cabinet includes a single imager. In some embodiments, an incubator cabinet includes two imagers. In some embodiments, the two imagers are the same type of imager (e.g., two holographic imagers or two bright-field microscopes). In some embodiments, the first imager is a bright-field microscope and the second imager is a holographic imager. In some embodiments, an incubator cabinet comprises more than 2 imagers. In some embodiments, cell culture incubators comprise three imagers. In some embodiments, cell culture incubators having 3 imagers comprise a holographic microscope, a bright-field microscope, and a fluorescence microscope.

As used herein, an "imaging location" is the location where an imager images one or more cells. For example, an imaging location may be disposed above a light source and/or in vertical alignment with one or more optical elements (e.g., lens, apertures, mirrors, objectives, and light collectors).

Modular Incubator Systems

In some embodiments, incubators described herein can be configured to form a plurality of modular workstations. Modular workstations may provide adequate processing capability for parallel cell culture, for example, each workstation performing a specific function in a protocol (e.g., a liquid handling workstation, a bright field imaging workstation, a bright field and/or fluorescent workstation, etc.). In some embodiments, workstations may also be configured for cell or stem cell colony identification and digital marking, cell manipulation, cell re-plating, and elimination of colonies, etc. In some embodiments, incubators described herein can be joined in an airtight manner (e.g., via transfer chambers each configured to connect incubator cabinets via internal doors) to form a modular complex of workstations. In some embodiments, workstations may comprise an imager, a cell culture transfer device, a manipulator, one or more storage locations, or a combination of the foregoing.

As used herein, a "fiducial mark" refers to a feature that facilitates alignment of one or more components. In some embodiments, fiducial marks may include one or more hole apertures over a fluorescent media or printed or embossed fluorescent material. In other embodiments, fiducial marks may include grids, lines, or symbols. In some embodiments, one or more cell culture vessels include one or more fiducial marks to facilitate alignment of one or more cell culture vessels with an imager. In some embodiments, fiducial marks may be associated with moving parts, including transfer devices and robotics devices.

In some embodiments, a cell culture vessel is substantially aligned with an imager. In some embodiments, a cell culture vessel is substantially aligned with an imager via the use of at least one fiducial mark. As used herein, the term "substantially aligned" implies that one or more elements are substantially overlapping, identical, and/or in line with one another. The substantial alignment of one or more cell culture vessels at one or more locations (e.g., imaging locations) may facilitate the analysis of a sample by permitting overlapping images of the cell culture vessel to be obtained. For example, a cell culture vessel may be imaged at a first imaging location by a first imager and subsequently imaged at a second imaging location by a second imager. If the imaging fields of the respective imagers are substantially aligned, the images recorded by the first and second imagers may be combined ("stitched together") for analysis. One or more fiducial marks present on one or more cell culture vessels may facilitate substantial alignment. In some cases, one or more fiducial marks present at one or more imaging or other locations (e.g., manipulation or maintenance locations) may facilitate substantial alignment.

In some embodiments, an opening (e.g., orifice) configured for transporting (e.g., aspirating, depositing, or aspirating and depositing) cells and/or cell culture media forms part of a channel. As used herein, a "channel" refers to a partially enclosed conduit (e.g., a cylindrical, tubular, or cuboid passage) designed to allow the transport of a objects (e.g., cell culture media, cells) from one location to another location. In some embodiments, a channel is integrated into a cell scraper (e.g., running along the inside or outside of a cell scraper handle and/or scraping blade). For example, in some embodiments, a cell scraper comprises a hollow handle configured to contain a channel comprising an opening, wherein the opening is located in or on the scraping blade (e.g., scraping edge) of the cell scraper. A channel residing within the interior of a hollow scraper handle (e.g., in a scraper handle cavity) can have a volume ranging from about 0.1% of the volume within the handle cavity to about 99% of the volume within the handle. For example, a channel can be a separate capillary tube or hollow needle (e.g., a needle having a gauge between 28 gauge and 10 gauge) that is directly connected or attached to a wall (e.g., running along an interior wall or exterior wall) of a hollow scraper handle. In some embodiments, the entire volume within a hollow scraper handle forms a channel. For example, in some embodiments, a cell scraper comprises a hollow handle and a scraper blade having an opening which is connected to the hollow interior (e.g., channel) of the handle. In some embodiments, internal structures such as a mesh, grill, screen, or star-shaped structure, to facilitate the mixing or breaking apart of aggregated cells, are integrated into the channel of a cell scraper handle and/or scraping blade. Without wishing to be bound by any particular theory, a cell scraper comprising an opening and a channel is capable of simultaneously performing cell scraping and liquid handling functions (e.g., simultaneously triturating cells and removing debris, such as triturated cells and cell culture media).

In some embodiments, a manipulator comprises at least one cell scraper. For example, a manipulator may comprise between about 1 and about 100, about 10 and about 100, about 20 and about 1000, or about 50 and about 500 cell scrapers. In some embodiments, a manipulator comprises 2, 3, 4, 5, 6, 7, 8, 9, 10, 15, 20, 24, 48, 96, 384, or 1536 cell scrapers. In some embodiments, a manipulator having a plurality of cell scrapers is referred to as having a "bank" of cell scrapers, as shown in FIG. 4B. In some embodiments, a manipulator comprises a single cell scraper. In some embodiments, an incubator may comprise multiple manipulators, each manipulator having at least one cell scraper.

In some embodiments, cell scrapers are useful for dissociating adherent cells from the surface (or surfaces) of a cell culture vessel. For example, cell scrapers may be utilized for manual, mechanical loosening of protein bonds of adherent cells to a culture vessel. In some instances, mechanical dissociation by scraping is aided by the use of an enzyme such as trypsin or ACCUTASE®. However, in certain embodiments, cell scraping is the preferred method of cell dissociation, primarily because the use of enzymes as the primary means of dissociation requires relatively long exposure of the cells to the enzyme in order to insure sufficient cellular detachment from the substrate. In some embodiments, scraping is the preferred methods for passaging stem cells during expansion.

A manipulator may include a cell picker. A manipulator for manipulating cells may operate by detecting desirable cells or groups thereof present at a first location based on a predetermined criterion and transferring the desired cells or groups thereof from the first location to a second location. A cell picker may detect, pick, and/or transfer desirable or undesirable (e.g., pre-differentiated cell weeding) cells or groups thereof based on a manual or automated analysis. In some embodiments, information produced by an imager may be analyzed to detect desirable or undesirable cells. The cell picker may then transfer the desirable or undesirable cells to the second location. For example, an imager may image cells in or on a cell culture vessel at an imaging location, and the image used to identify desirable or undesirable cells or groups thereof. The cell picker may then transfer the desirable or undesirable cells, e.g., by contacting each desired cell or cells with a needle, capillary, pipette, or micromanipulator and effecting a movement of the cell or cells, from their first location to a second location in or on the cell culture vessel or elsewhere in the internal chamber. In some embodiments, the first location of the cells may be in or on a cell culture vessel. In particular embodiments, a cell picker transfers cells from a first location in or on a cell culture vessel to a second location on the same cell culture vessel. In other embodiments, a cell picker transfers cells from a first location in or on a first cell culture vessel to a second location in or on a second cell culture vessel. In certain other embodiments, a cell picker transfers cells from a first location in or on a cell culture vessel to a second location in the internal chamber that is not in or on a cell culture vessel.

In some embodiments, the manipulator includes at least one microelectrode. As used herein, the term "microelectrode" refers to an electrical conductor used to deliver electrical stimulation to a cell. For example, microelectrodes can be used to deliver genetic material into a cell by electroporation. In some embodiments, the manipulator includes at least one microinjector. Generally, microinjectors are glass micropipettes that have been pulled to form a sharp, hollow structure capable of piercing the membrane of a cell and serving as a conduit for the introduction of genetic material into the cell.

In some embodiments, a manipulator is manually operated. For example, a manipulator having a cell picker located inside the internal chamber of an incubator cabinet may be electronically-linked to and controlled by a user-directed joystick located outside the internal chamber of the incubator cabinet. In some embodiments, the user-directed joystick is connected to a display device. In some embodiments, the display device shows images captured by an imaging device inside the internal chamber of the incubator cabinet.

In some embodiments, a manipulator is automated. For example, a manipulator inside an internal chamber of an incubator cabinet may be electronically connected to a controller outside of the incubator cabinet, which is electronically connected to a computer that directs the manipulator. In some embodiments, a controller interfaces with hardware configured for quantifying and modulating contact force between a scraping edge and the surface of the cell culture vessel to which the cells are adhered. For example, a manipulator or cell scraper may further comprise a sensor (e.g., a pressure sensor) that provides signal to a controller informative of a sensed pressure, which in response to the controller transmits a signal (e.g., to a manipulator) to increase or reduce the pressure which the manipulator exerts upon the scraping edge (e.g., a blade) of the cell scraper. In some embodiments, a controller comprises software and/or hardware configured for programming up to 360.degree. rotation of the scraper tip/blade, thus allowing for programming of scraping motion in coordination with linear motion in the x-, y-. and z-axis such that a constant angle of attack is maintained between the scraper blade and the cells being scraped, regardless of culture vessel well geometry. In some embodiments, the controller interfaces with one or more components or hardware configured to permit location and determination, e.g., via imaging, of aggregated clump(s) of cells, thus allowing subsequent scraping/aspiration via the manipulator-controlled cell scraper.

One or more elements of the manipulator for manipulating cells may be sterilized, for example using a sterilizing composition or method (e.g., ethanol or ozone gas, UV Light, Hydrogen peroxide), prior to manipulation.

As used herein, "manipulation location" or station refers to the location at which cells are manipulated by a manipulator for manipulating cells (e.g., a cell picker). In certain embodiments, the manipulation location may be the same as the imaging location.

According to one aspect, the cell culture incubator includes an incubator cabinet with an imaging location and a manipulating location. Cells of a cell culture vessel are imaged at the imaging location by an imager and manipulated at the manipulating location by a manipulator. In some embodiments, the imaging location and the manipulating location are two distinct locations within the incubator cabinet. The cell culture incubator may include a transfer device that moves cell culture vessels between the imaging location and the storage location. In other embodiments, the imaging location and the manipulating location are the same, such that the cells of culture vessels are imaged at the manipulation location.

In some embodiments, an imager may be used in conjunction with a manipulator. For example, an imager may image cells in or on a cell culture vessel at an imaging location, and the image used to identify desirable cells or groups thereof. The cell picker, which may or may not be resident at the imaging location, may then transfer the desirable or undesirable cells, e.g., by contacting each desired cell or cells with a needle, capillary, pipette, or micromanipulator and effecting a movement of the cell or cells, from their first location to a second location in or on the cell culture vessel or elsewhere in the internal chamber. In some embodiments, a cell picker transfers cells from a first location in or on a cell culture vessel to a second location on the same cell culture vessel. In other embodiments, a cell picker transfers cells from a first location in or on a first cell culture vessel to a second location in or on a second cell culture vessel. In certain other embodiments, a cell picker transfers cells from a first location in or on a cell culture vessel to a second location in the internal chamber that is not in or on a cell culture vessel.

In some embodiments, a single location within the incubator cabinet may serve as an imaging location and a manipulating location. In one embodiment, cells are imaged as they are manipulated by the manipulator. In some embodiments, the imaging location and imaging location may be at separate locations within the incubator cabinet.

In some embodiments, the manipulator includes sensors that allow it to report its position and determine when it has touched the bottom of the cell culture vessel. In some embodiments, an imager may be used to guide the manipulator in order to achieve repeatability and accuracy. In some embodiments, compliance (e.g., springiness) in the manipulator may be used to relax the need for extreme mechanical accuracy.

Figure 10:
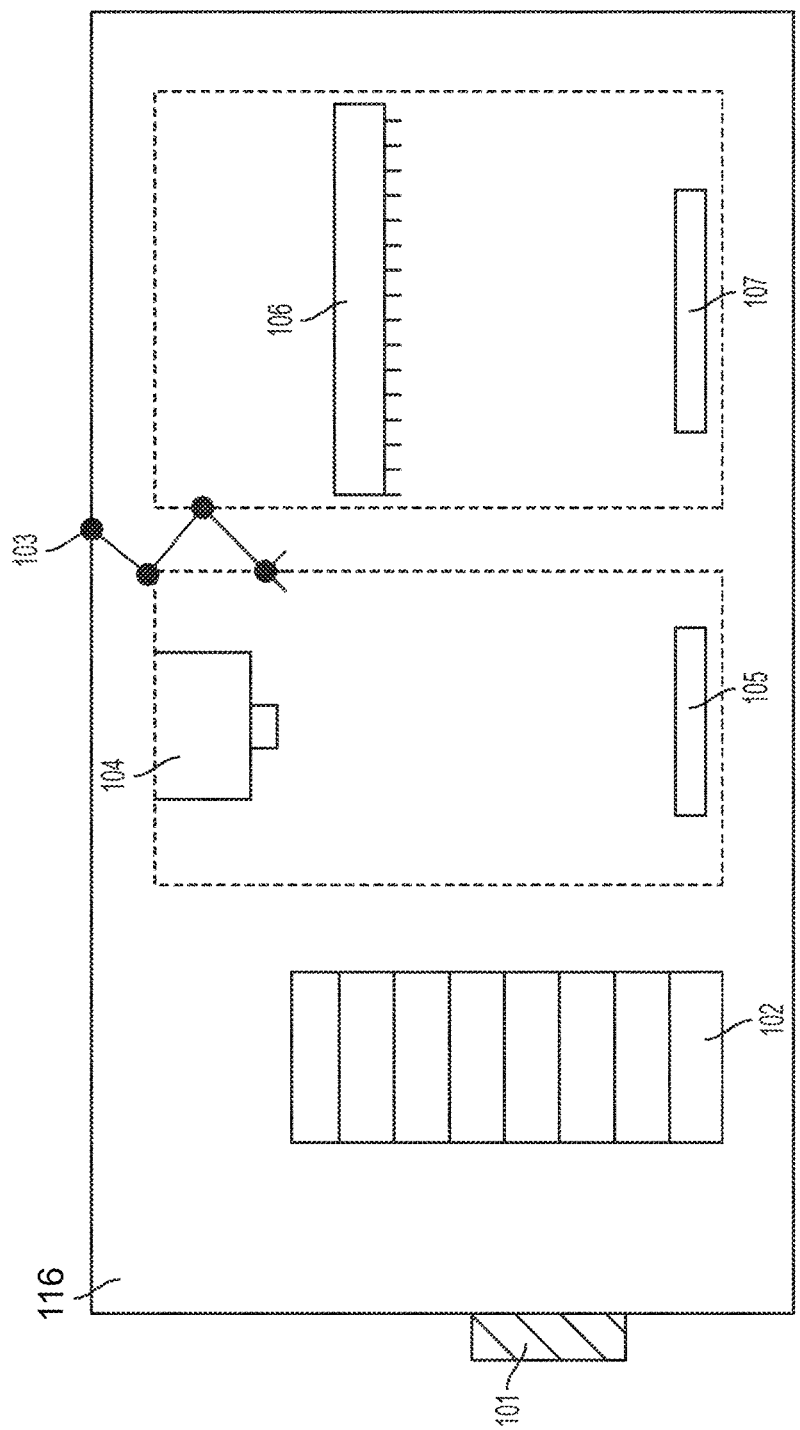
FIG. 10 is a schematic of an illustrative embodiment of a cell culture incubator having an imager and a manipulator.

Turning to the figures, FIG. 10 depicts one illustrative embodiment of a cell culture incubator. The cell culture incubator includes an incubator cabinet having an internal chamber (116) for incubation of cells in one or more cell culture vessels. The incubator cabinet includes an external door (101) that opens and closes to permit communication between an external environment and the incubator cabinet. In some embodiments, the external door opens and closes to permit communication between an external environment and the internal chamber. The internal chamber is configured to hold one or more cell culture vessels. The one or more cell culture vessels are stored in a storage location (102). In some embodiments, the storage location is a free-standing structure. For example, a storage location may be a test tube or culture flask rack that can be removed from the internal chamber of the incubator for loading and unloading of culture vessels. In some embodiments, the storage location is affixed to a surface of the internal chamber. For example, the storage location may be a series of racks or shelves that are connected to the walls or floor of the internal chamber and are thus not able to be removed from the incubator cabinet.

In some embodiments, the cell culture incubator includes a cell culture vessel transfer device (103) for moving one or more cell culture vessels. The cell culture transfer device may be affixed to any appropriate surface of the internal chamber of the incubator. For example, the cell culture vessel transfer device may be affixed to the top or ceiling of the internal chamber. Alternatively, the cell culture vessel transfer device may be affixed to a side wall of the internal chamber. In some embodiments, the cell culture vessel transfer device is not affixed to the wall of the internal chamber. For example, the cell culture vessel transfer device may rest on a wheeled tripod or other mobile structure that can be moved around the internal chamber.

In some embodiments, the transfer device moves one or more cell culture vessels from a storage location (102) to an imaging location (105) or to a manipulation location (107). The transfer device (103) can also move one or more cell culture vessels from an imaging location (105) to a manipulation location (107) or from a manipulation location (107) to an imaging location (105). When imaging or manipulation are complete, the transfer device (103) moves one or more cell culture vessels from an imaging location (105) or a manipulation location (107) to a storage location (102).

In some embodiments, the incubator cabinet includes a first imaging location (105) and a manipulation location (107). In some embodiments, one or more imaging locations are located on a surface of the internal chamber opposite from an imager. In some embodiments, imaging locations are platforms, either free-standing or affixed to a surface of the internal chamber. In some embodiments, the platform is movable. For example, a movable platform may be affixed to two or more rods that allow the platform to be moved left, right, forward, backward, up or down in relation to an imager. In some embodiments, the movable platform is motorized.

In some embodiments, the incubator cabinet includes a first imager (104) that images the cells of cell culture vessels when the vessels are at the first imaging location (105). In some embodiments, the first imager is a bright-field microscope. In some embodiments, the first imager is a holographic microscope. In some embodiments, the first imager is a phase-contrast microscope.

In some embodiments, a manipulator (106) manipulates the cells of cell culture vessels when the vessels are at the manipulation location (107). In some embodiments, the manipulator has an array of needles, capillaries, pipettes, and/or micromanipulators. For example, the manipulator may include a cell picker. In some embodiments, a manipulator comprises one or more cell pickers. In some embodiments, the manipulator may include a cell scraper. In some embodiments, a manipulator comprises one or more cell scrapers. Generally, manipulation locations share many characteristics with imaging locations, as described herein.

Figure 11:
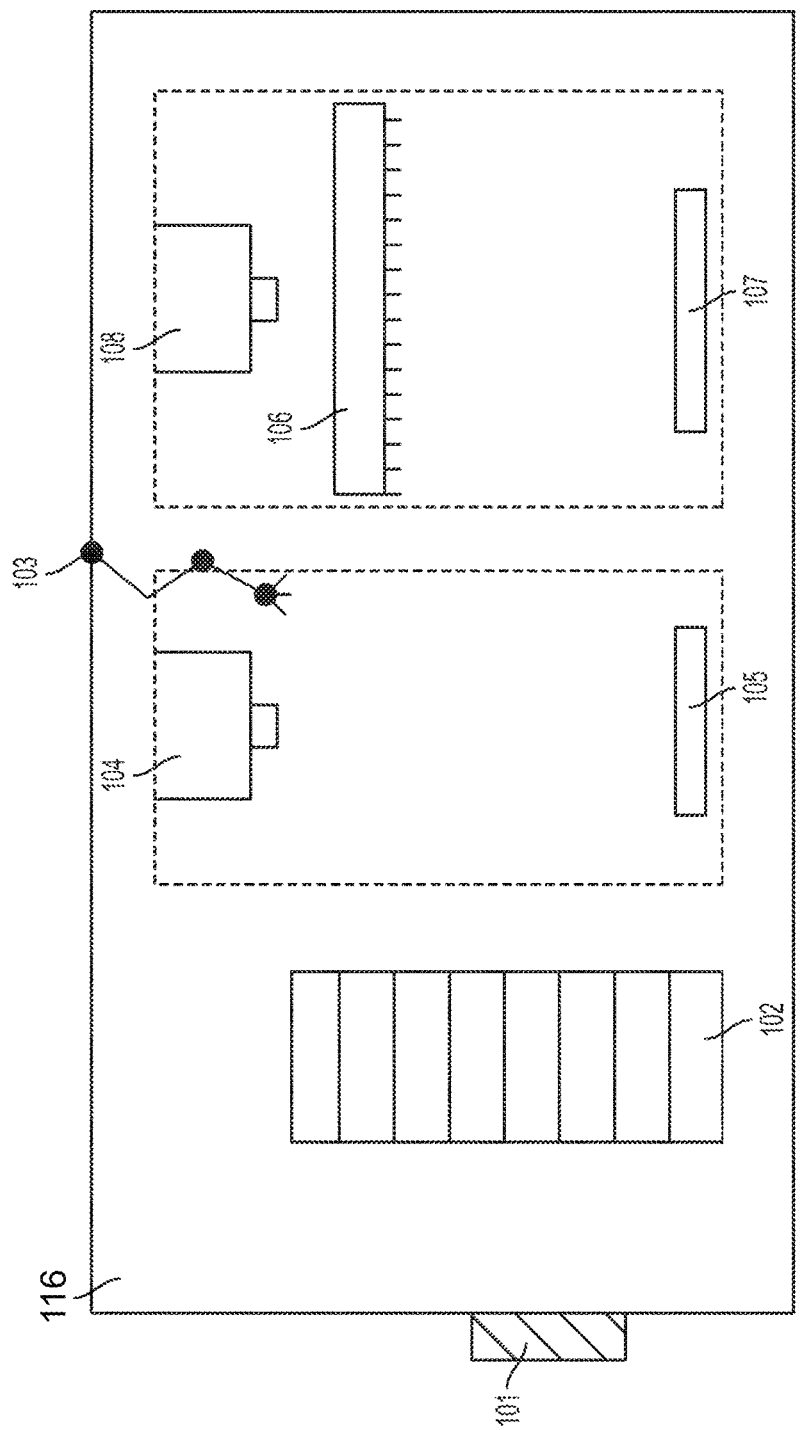
FIGS. 11-12 are schematics of illustrative embodiments of cell culture incubators.

FIG. 11 depicts one illustrative embodiment of a cell culture incubator. In some embodiments, the incubator cabinet has a second imager (108). The second imaging location may be at or near the manipulation location (107). In some embodiments, the second imaging location and the manipulation location (107) are the same location. In some embodiments, a second imager (108) images the cells of cell culture vessels while the cells are manipulated by the manipulator (106). In some embodiments, the second imager is a bright-field microscope. In some embodiments, the second imager is a holographic microscope. In some embodiments, the first imager is a phase-contrast microscope.

Figure 12:
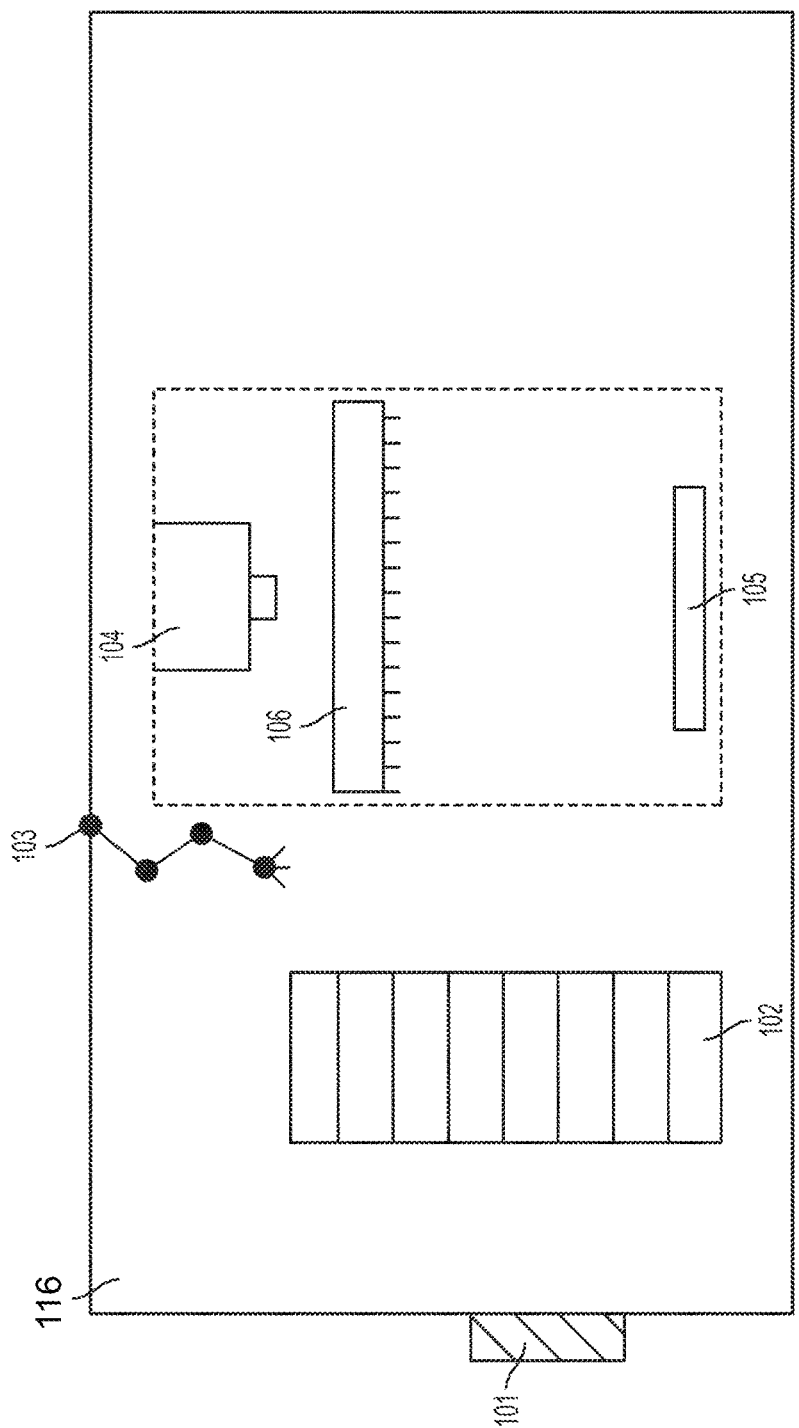

FIG. 12 depicts one illustrative embodiment of a cell culture incubator. In some embodiments, the cell culture incubator has an imaging location and a manipulation location that are the same location (105).

Figure 13:
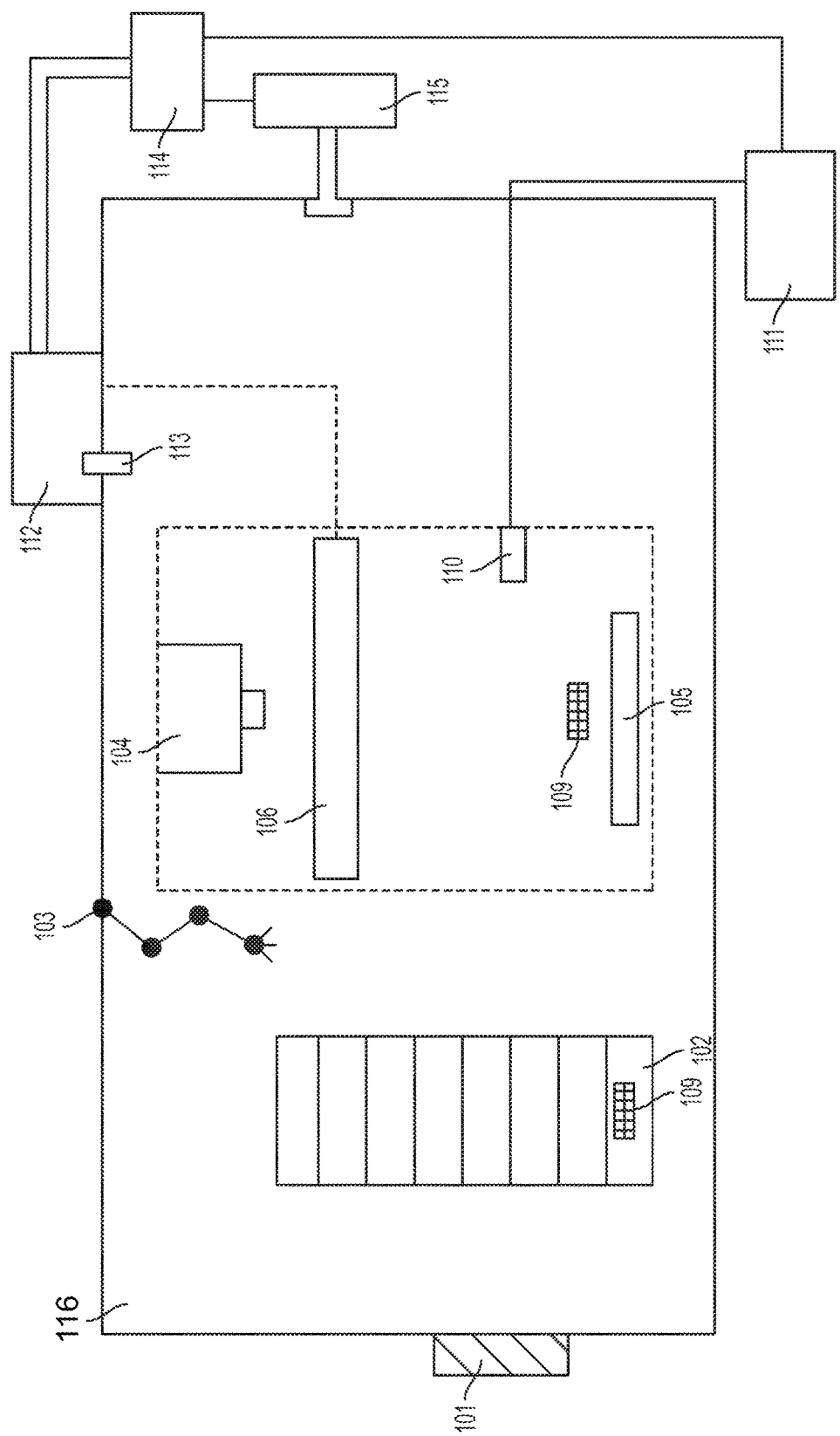
FIG. 13 is a schematic depicting further components of cell culture incubators.

FIG. 13 depicts illustrative embodiments of further components of a cell culture incubator. Further components are any component of the incubator that is not listed in FIGS. 10-12. In some embodiments, a cell culture incubator contains barcoded cell culture vessels (109). Thus, in some embodiments, a cell culture incubator has a barcode scanner (110) located inside the internal chamber of the incubator cabinet. In some embodiments, the barcode reader communicates with a computer (111) to relay information about the cell culture vessel for which the barcode has been scanned. In some cases, a barcode scanner may be affixed to any surface of the internal chamber. For example, a barcode scanner can be affixed to a wall of the internal chamber in close proximity to an imaging location (105).

In some embodiments, the cell culture incubator contains at least one probe and/or at least one sensor (113) that measures environmental conditions within the internal chamber. Examples of probes to measure environmental conditions include but are not limited to temperature probes, pressure probes, carbon dioxide ($CO_2$) sensors, oxygen ($O_2$) sensors and relative humidity sensors. In some embodiments, the at least one probe and/or at least one sensor located within an instrument housing (112). The at least one probe and/or at least one sensor is connected to a controller (114). In some embodiments, the controller (114) communicates with a computer (111). Additionally, the controller (114) may communicate with a fluid dispensing system (115). For example, if a $CO_2$ sensor indicates a low $CO_2$ level in the internal chamber, the controller (114) may direct the fluid dispensing system to inject $CO_2$ gas into the internal chamber in order to increase the $CO_2$ level of the internal chamber.

Figure 14:
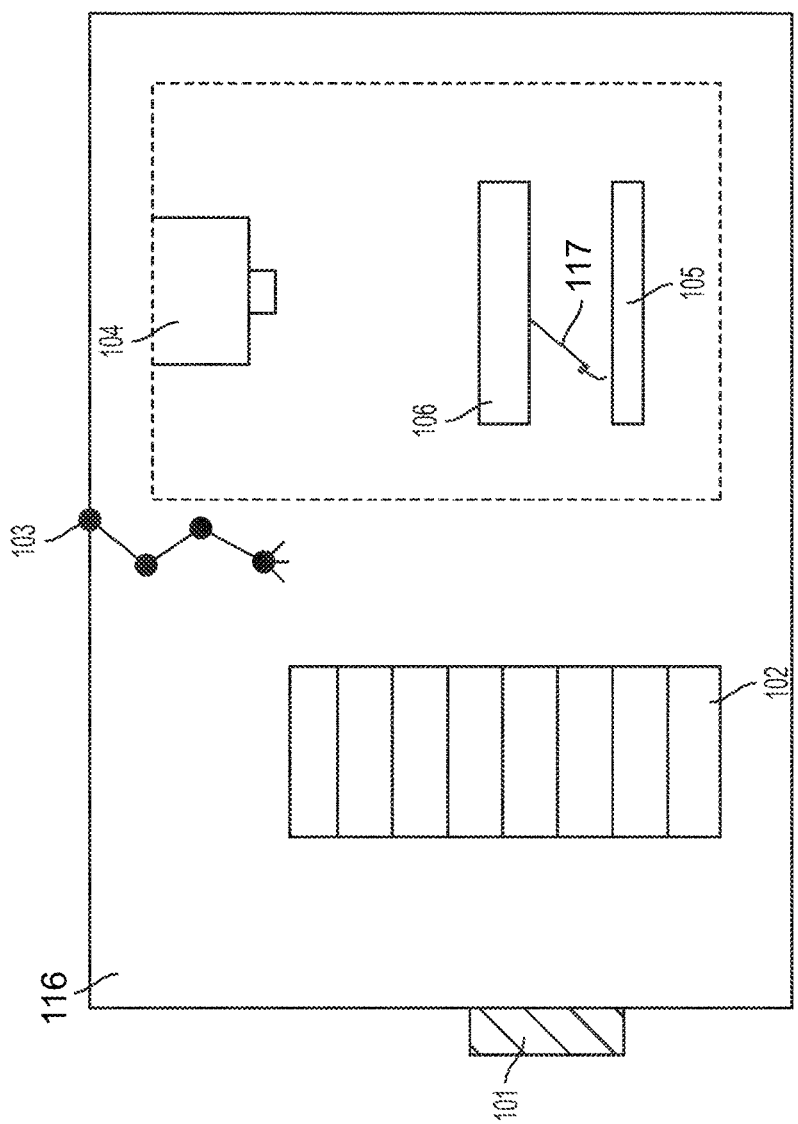
FIGS. 14-15 are schematics of illustrative embodiments of cell culture incubators.

FIG. 14 depicts a schematic of an illustrative embodiment of a cell culture incubator. In some embodiments, a manipulator (106) comprises one or more cell scrapers (117), as shown in FIG. 14. In some embodiments, a manipulator (106) comprises a plurality of cell scrapers (e.g., a bank of cell scrapers. In some embodiments, the incubator comprises two manipulators wherein each manipulator comprises a cell scraper. In some embodiments, the manipulator (106) is controlled by a controller (object (114) of FIG. 13) that is configured for programming of up to 360 degree rotation of the scraper tip/blade of the cell scraper, thus allowing for programming of scraping motion in coordination with linear motion in the x-, y-. and z-axis, e.g., such that a constant angle of attack is maintained between the scraper blade and the cells being scraped, regardless of culture vessel well geometry.

In some aspects, this document relates to cell culture systems including an incubator cabinet. As used herein, an "incubator cabinet" is a housing that includes one or more chambers configured to hold one or more cell culture vessels. In some embodiments, an incubator cabinet includes a transfer chamber and an internal chamber, one or both of which are configured to hold one or more cell culture vessels. In some embodiments, an incubator may include one or more other elements such as one or more gas sources (e.g., a gas cylinder or ozone generator), tubing (e.g., to convey one or more liquids or gases such as water, distilled water, deionized water, cell culture medium, air, carbon dioxide, ozone, and oxygen), airflow mechanisms (e.g., valves, release valves, pinholes, gas regulators, and mass flow regulators), pressure mechanisms (e.g., a pump such as a dry scroll pump, rotary pump, momentum transfer pump, diffusion pump, or diaphragm pump; a suction tube; a vacuum system; and an air blower), environmental monitors and controls (e.g., a gas sensor and/or monitor to sense and/or control concentrations of gases such as carbon dioxide, oxygen, and ozone; heat sources or sinks; temperature monitors and controls; humidity monitors; gas scrubbers; air filters; instrumentation for measuring particulate matter; pressure gauges; and flow meters), doors (e.g., openings or panels), windows (e.g., optical windows made of glass, plastic, composite, or other substantially transparent material for viewing an area inside the incubator cabinet), ports (e.g., to permit the introduction or removal of one or more gases or liquids), light sources (e.g., lamps, bulbs, lasers, and diodes), optical elements (e.g., microscope objectives, mirrors, lenses, filters, apertures, wave plates, windows, polarizers, fibers, beam splitters, and beam combiners), imaging elements (e.g. cameras, barcode readers), electrical elements (e.g., circuits, cables, power cords, and power supplies such as batteries, generators, and direct or alternating current supplies), computers, mechanical elements (e.g., motors, wheels, gears, robotic elements, and actuators such as pneumatic actuators, electromagnetic actuators, motors with cams, piezoelectric actuators, and motors with lead screws), and control elements (e.g., spin-wheels, buttons, keys, toggles, switches, cursors, screws, dials, screens, and touchscreens). In some embodiments, one or more of these other elements are part of the incubator but are external to the incubator cabinet. In some embodiments, one or more of these other elements are included within the incubator cabinet.

In some embodiments this document relates to incubators and methods for culturing, manipulating, and/or monitoring cells under controlled conditions (e.g., under aseptic and/or sterile conditions). In some embodiments, the cell culture incubators included an incubator cabinet having an internal chamber for incubation of cells in one or more cell culture vessels. In some cases, in addition to an internal door from the transfer chamber to the internal chamber, the incubators include at least one external door (e.g., 1, 2, 3, 4, or more external doors) opening from an external environment directly to the internal chamber, for example, to provide alternative access to the internal chamber during periods of time when the incubator is not operational, e.g., during maintenance of the incubator. In some embodiments, incubators include a storage location within the internal chamber for storing one or more cell culture vessels.

Figure 15:
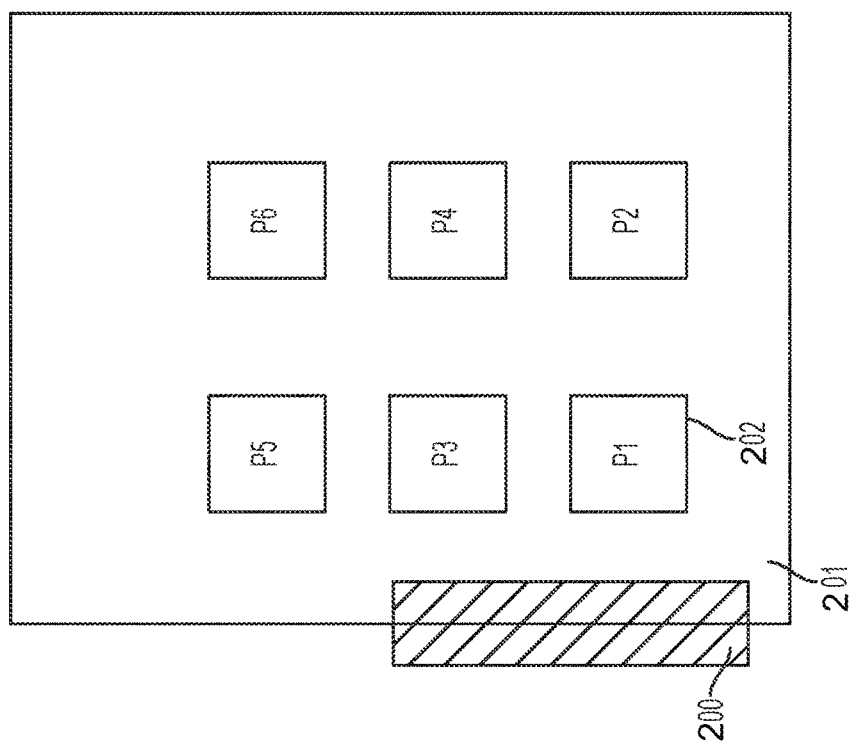

Turning to the figures, FIG. 15 shows a schematic of an illustrative embodiment of a cell culture system. In some embodiments, a cell culture system includes an incubator cabinet having an external door (200) which opens into an internal chamber (201). Inside the internal chamber are a plurality cell culture vessels (202), each vessel having a passage configured to permit materials to be aseptically passed into or out from the vessel; each cell culture vessel (P1, P2, P3, P4, P5, and P6) may contain a cell sample from a different subject.

Figure 16A:
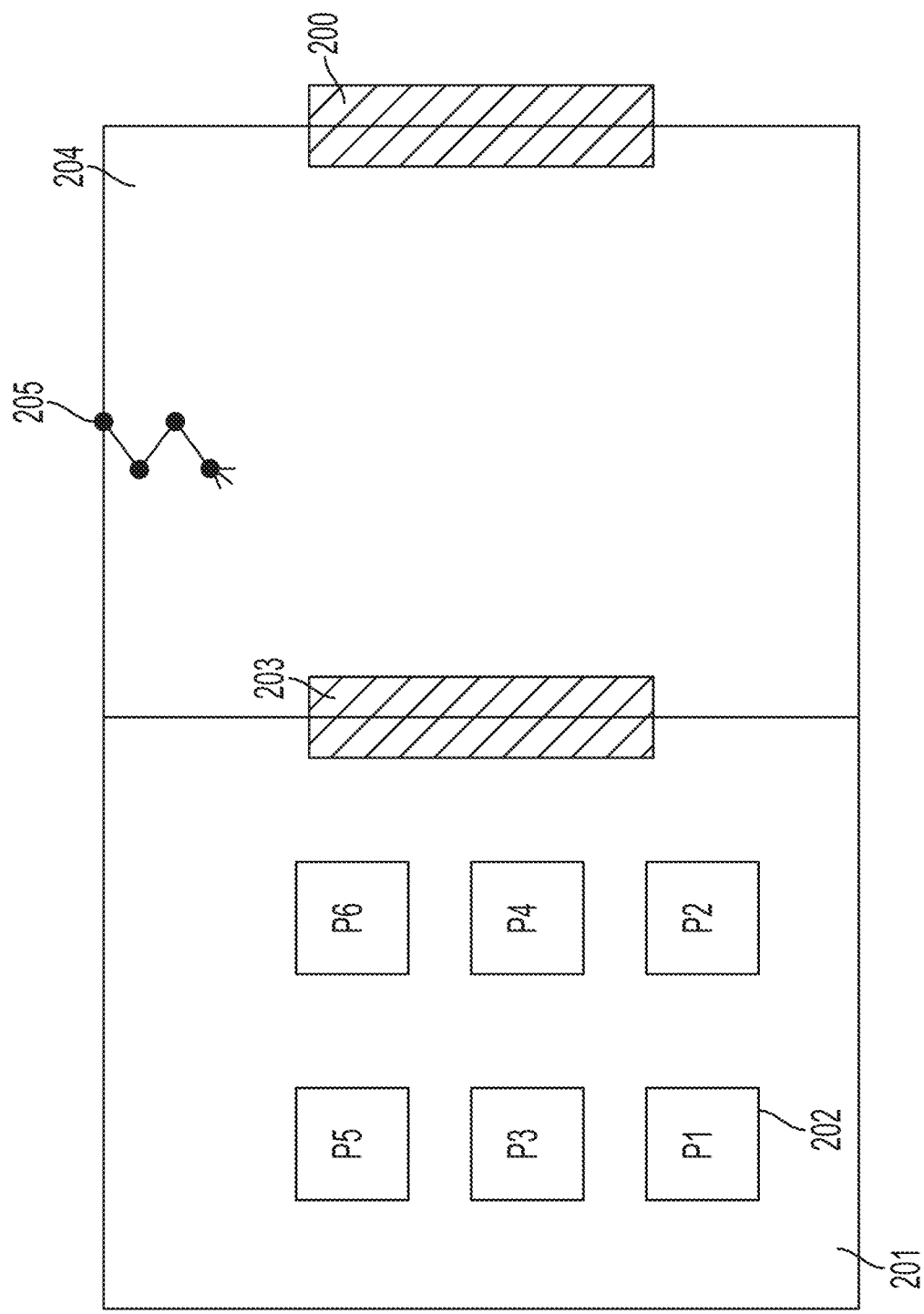
FIGS. 16A-16B are schematics of illustrative embodiments of cell culture systems.
Figure 16B:
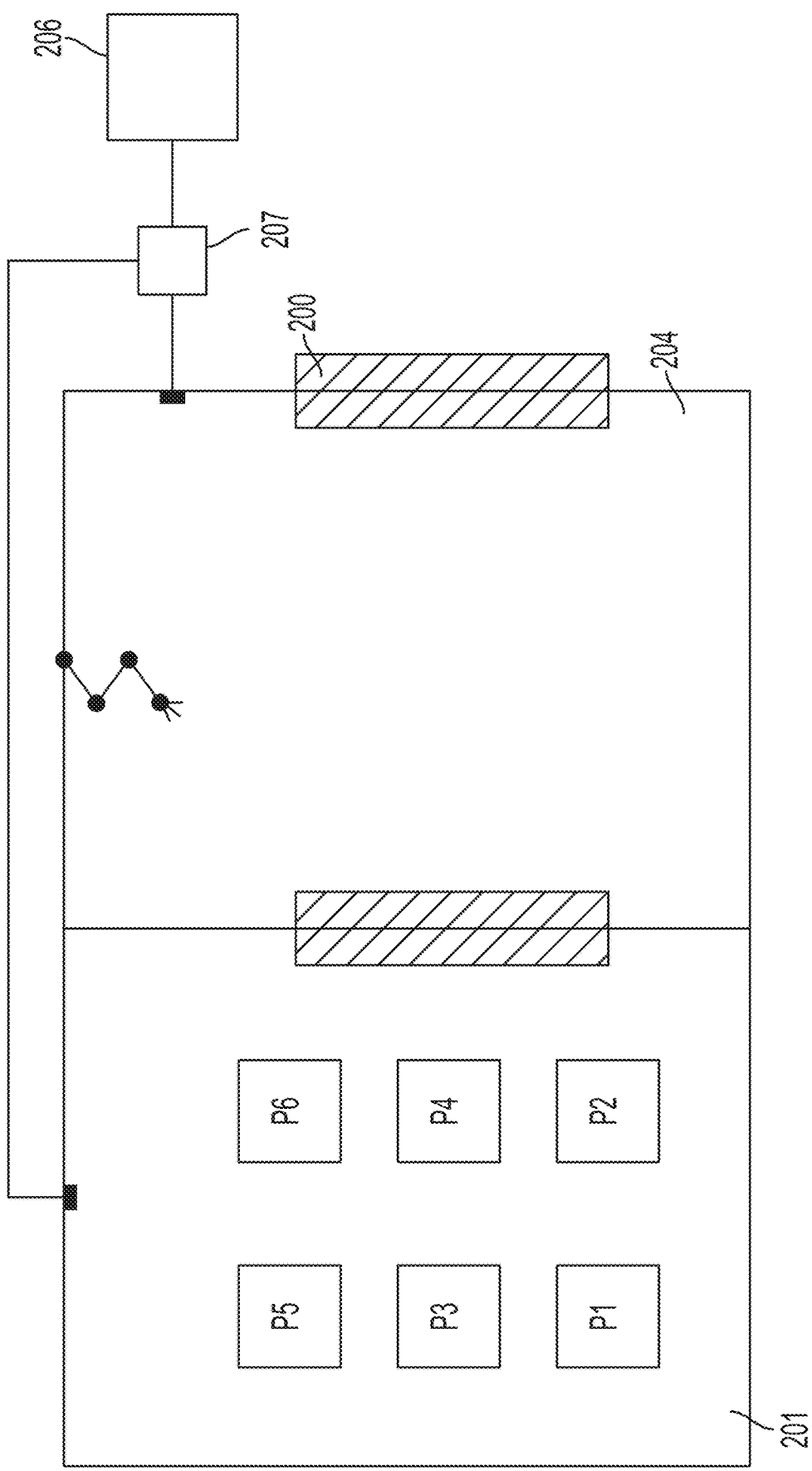

FIGS. 16A-16B show schematics of illustrative embodiments of a cell culture systems. FIG. 16A depicts a cell culture system including an incubator cabinet having an internal chamber (201) housing a plurality of cell culture vessels (202), each vessel having a passage configured to permit materials to be aseptically passed into or out from the vessel; an internal door (203), which opens into a transfer chamber (204), and forms a gas-tight seal when closed; a cell culture vessel transfer device (205); and, an external door (200) that connects the transfer chamber to the exterior of the incubator cabinet when open. FIG. 16B depicts a schematic of the cell culture system embodied in FIG. 16A, further including an ozone generator (206) and a pump (207). In some embodiments, the ozone generator and pump are in fluid communication. In some embodiments, the ozone generator and the incubator cabinet are in fluid communication. For example, the ozone generator can be in fluid communication with the internal chamber and/or the transfer chamber of the incubator cabinet via a pipe or tubing connected to an inlet or outlet of the incubator cabinet. In some embodiments, the pump and the incubator cabinet are in fluid communication. For example, the pump can be in fluid communication with the internal chamber and/or the transfer chamber of the incubator cabinet via a pipe or tubing connected to an inlet or outlet of the incubator cabinet. In some embodiments, the pump is used to remove ozone gas from the internal chamber and/or transfer chamber of the incubator cabinet.

Figure 17:
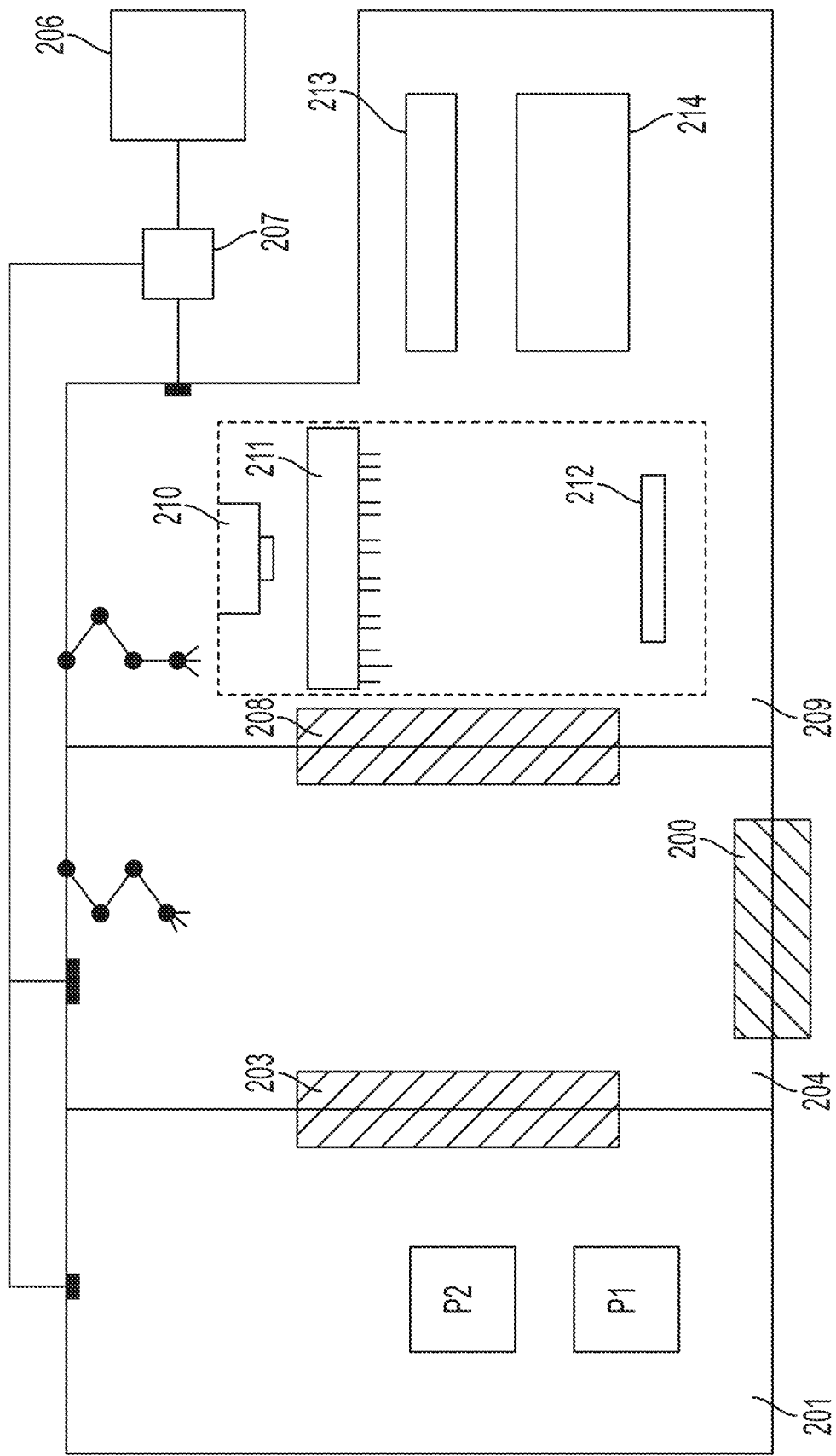
FIG. 17 is a schematic of an illustrative embodiment of a cell culture system comprising an incubator cabinet comprising a transfer cabinet, a first internal chamber containing a plurality of cell culture vessels, and a second internal chamber comprising an imager and a manipulator.

FIG. 17 shows a schematic of an illustrative embodiment of a cell culture system. In some embodiments, the cell culture system includes an incubator cabinet having an external door 2100), which opens into a transfer chamber (204). The transfer chamber has two internal doors (203, 208). The first internal door (203) opens into a first internal chamber (201), which houses a plurality of cell culture vessels, each vessel having a passage configured to permit materials to be aseptically passed into or out from the vessel. The second internal door (208) opens into a second internal chamber (209). The second internal chamber includes an imager (210), a manipulator (211) and a manipulation location (212). In some embodiments, the second internal chamber also includes a fluid reservoir (213) and/or a centrifuge (214). In some embodiments, the second internal chamber includes a FACS machine.

Figure 18:
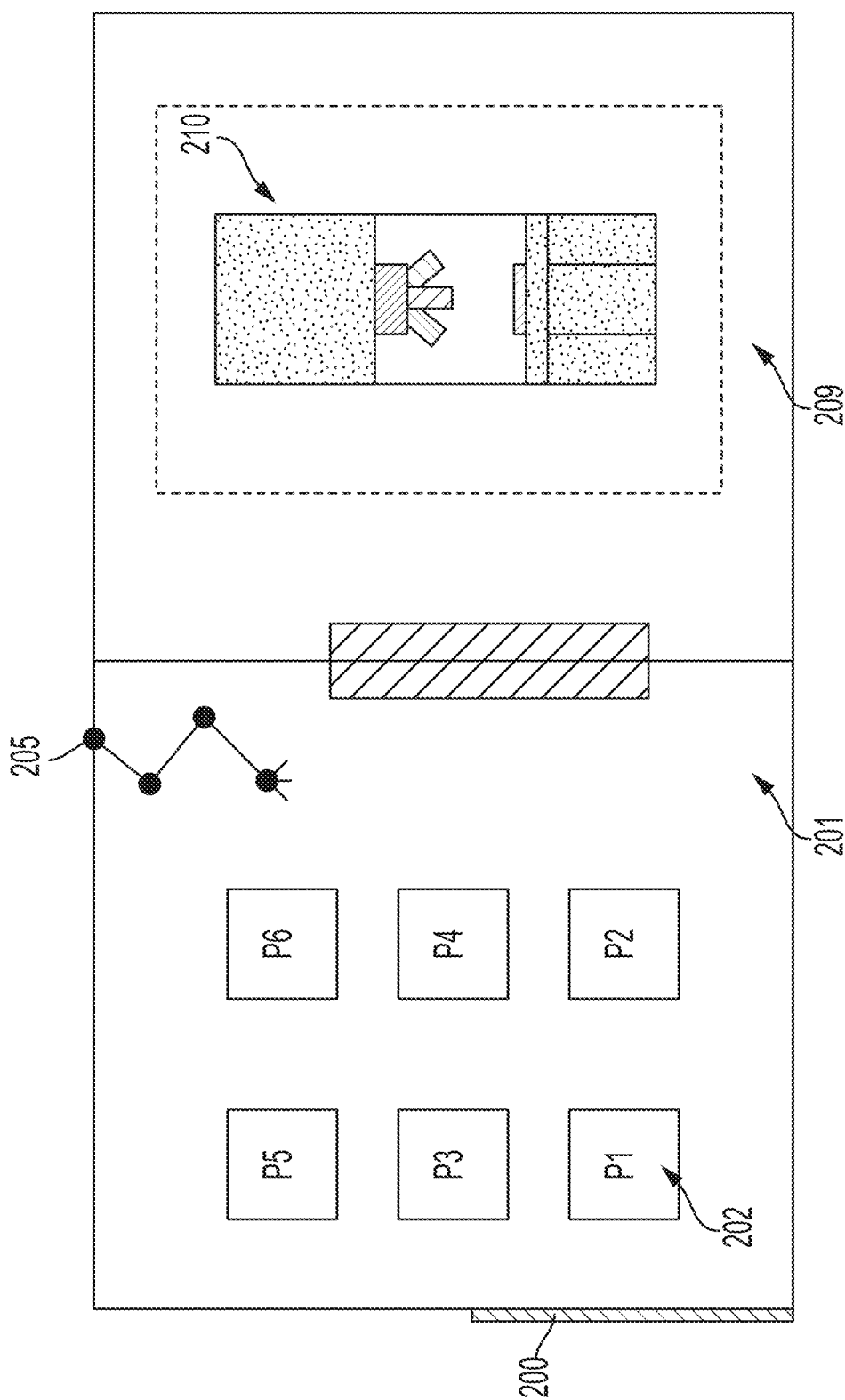
FIG. 18 is a schematic of an illustrative embodiment of a cell culture system comprising an incubator cabinet comprising an internal chamber, a plurality of cell culture vessels, and an imager.

FIG. 18 shows a schematic of an illustrative embodiment of a cell culture system. In some embodiments, the incubator cabinet includes an external door (200) that opens into a first internal chamber (201), which houses a plurality of cell culture vessels, each vessel configured to permit materials to be aseptically passed into or out from the vessel, the incubator cabinet includes a transfer device (205). An internal door connects the first internal chamber to a second internal chamber (209), that includes an imager (210).

Figure 19:
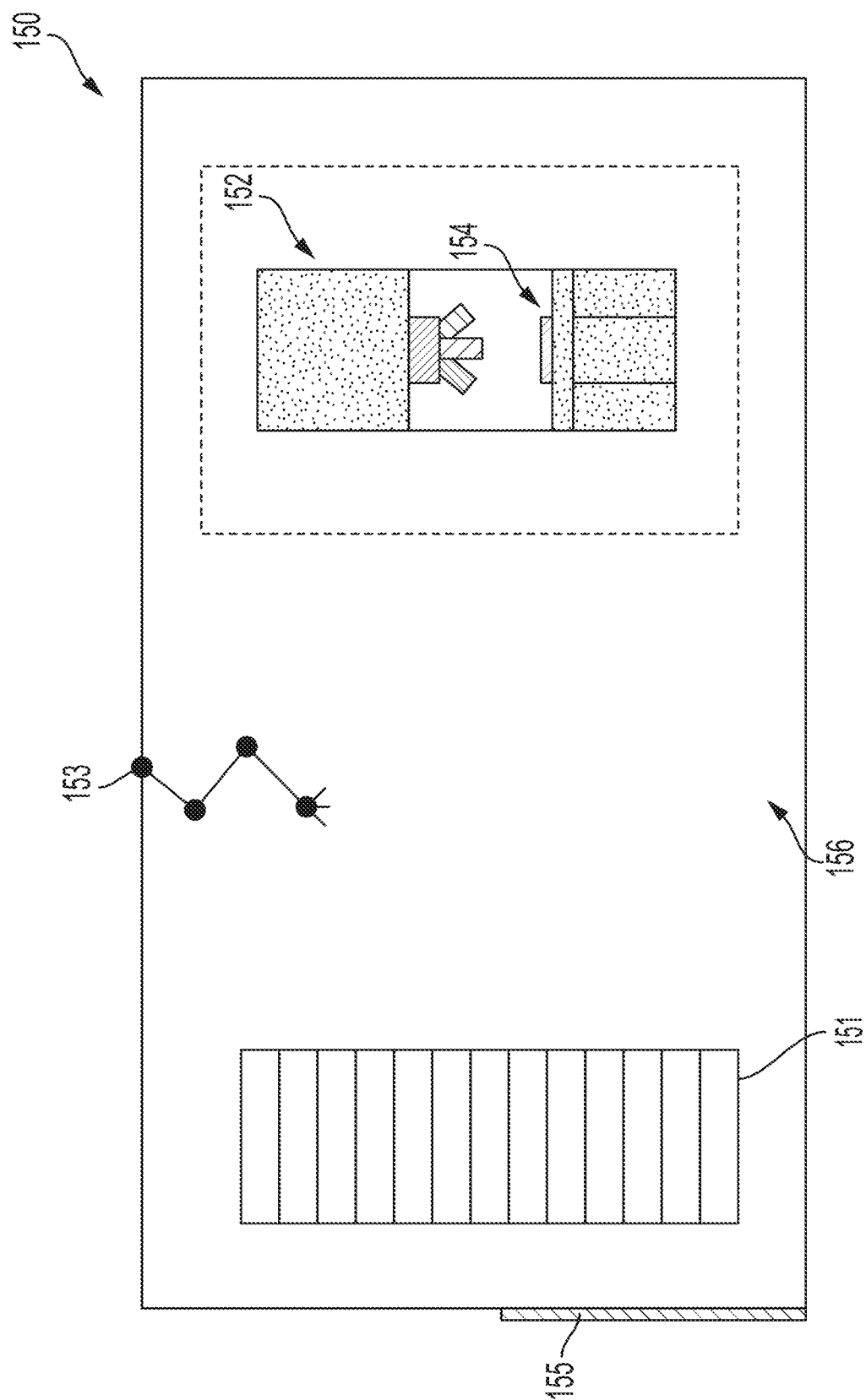
FIG. 19 is a schematic of an automated cell culture incubator having an integrated imaging system.

Turning to the figures, FIG. 19 depicts one illustrative embodiment of a cell culture incubator (150) having a holographic or phase-contrast imager (152). The cell culture incubator includes an incubator cabinet having an internal chamber (156) for incubation of cells in one or more cell culture vessels. The internal chamber is configured to hold one or more cell culture vessels at a storage location or station (151). The incubator cabinet includes an external door (155) that opens and closes to permit communication between an external environment and the internal chamber. In some embodiments, the external door (155) opens and closes to permit communication between an external environment and the internal chamber (156).

The incubator cabinet includes a first imaging location (154) where cells can be imaged. The cell culture incubator includes a holographic imager or phase-contrast (152) that images cells of cell culture vessels that are positioned at the first imaging location 154. In one embodiment, the cell culture incubator includes a second imager that images cells at the first imaging location or at another imaging location.

The cell culture incubator includes a transfer device (153) for moving one or more cell culture vessels between the first imaging location (154) and the storage location (151). In some embodiments, the storage location comprises "pigeon holes", or nests, mounted on a circular platform which may rotate to the imaging location (154). In instances where a second imager is present, the transfer device (153) can be used to move the one or more cell culture vessels between the storage location (151) and different imaging locations.

Figure 20:
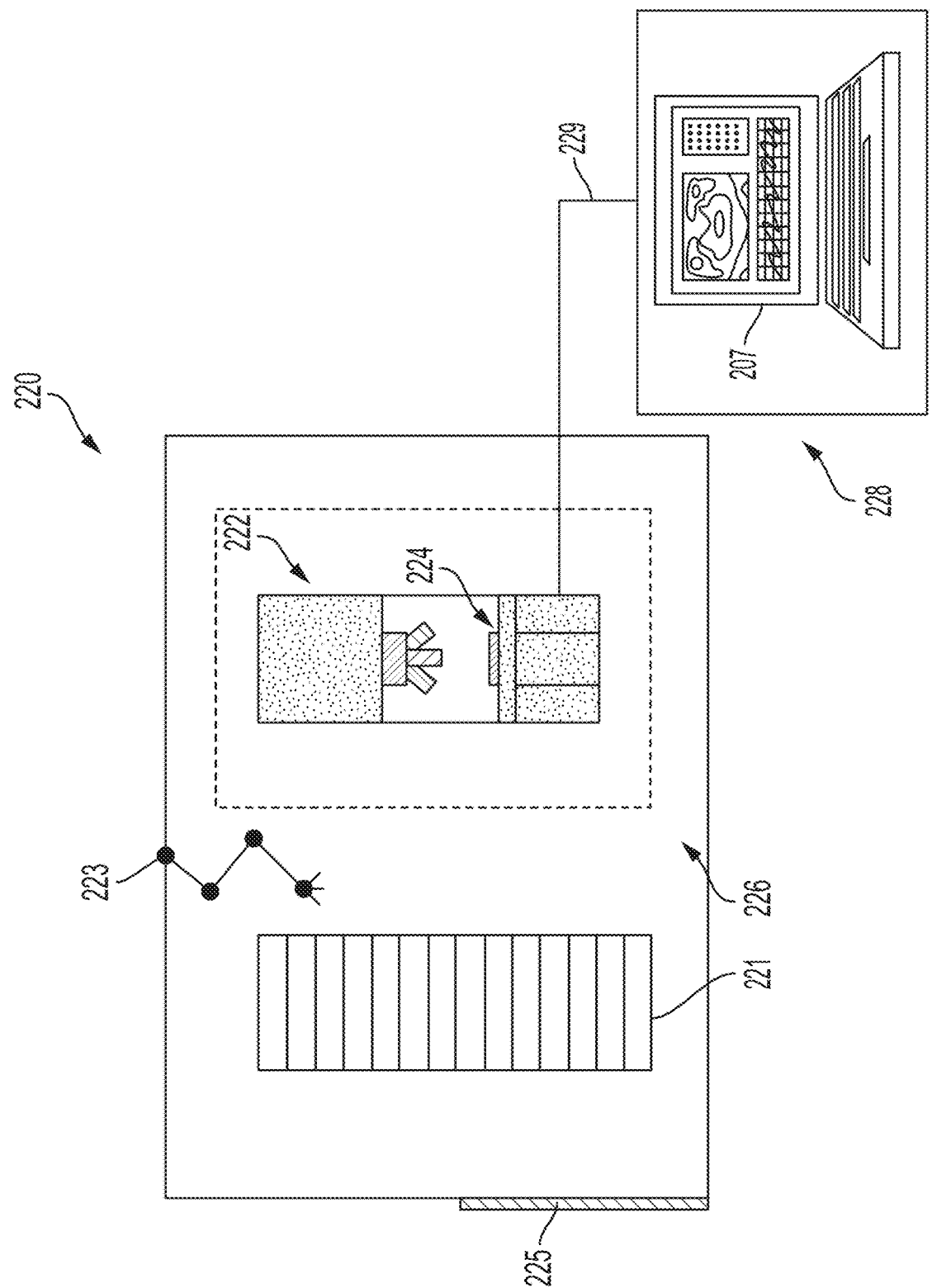
FIG. 20 is a schematic of an automated cell culture incubator having an integrated imaging system, which includes a computer workstation.

FIG. 20 depicts another illustrative embodiment of a cell culture incubator (220) having a holographic or phase-contrast imager (222) and an external computer station (228). As above, the cell culture incubator includes an incubator cabinet having an internal chamber (226) for incubation of cells in one or more cell culture vessels, and the internal chamber (226) is configured to hold one or more cell culture vessels at a storage location (221). The incubator cabinet includes an external door (225) that opens and closes to permit communication between an external environment and the internal chamber. The incubator cabinet includes a first imaging location (224) where cells can be imaged. Cells can be monitored over time (e.g., during a long-term culture) using the holographic or phase-contrast imager (222) by transferring one or more cell culture vessels back and forth between the storage location (221) to the first imaging location (224) using the transfer device (223). The holographic or phase-contrast imager (222) can be used to acquire images of the cells. Image information from the holographic or phase-contrast imager (222) can be transferred to the external computer station (228) via a communication line (229).

A computer (227) is provided with a display to permit a user to monitor cultures externally, e.g., by visualizing images on a display. In some cases, images can be stored, processed and analyzed automatically using image processing and analytical techniques implemented by the computer (227) to produce quantitative information regarding cell growth, development, viability, health, differentiation state, or other parameters. This quantitative information can be used to assess long term cultures and ensure cell health or other desired conditions. This information, along with the images, can be stored in a manner that permits correlation with other acquired data such as timestamps and sensor outputs. Storage can be in a database or in a file system. Storage can consist of selected images or a complete history of every image captured. While a communication line (229) is depicted in this illustrative embodiment for sending image information between the holographic or phase-contrast imager (222) and the computer (227), a hard communication line need not be used in all cases. For example, in some embodiments, information can be communicated between the holographic or phase-contrast imager (222) and a computer (227) wirelessly (e.g., using Bluetooth technology, WIFI, or other means of wireless communication). Similarly, a computer at which images from the holographic or phase-contrast imager (222) are analyzed or viewed need not be in close proximity to the incubator. For example, a computer can be in another room, another building, or at a remote location. In such cases information can be passed between the holographic or phase-contrast imager (222) and computer (227) through a wireless network, a local network, over the Internet, or other appropriate means.

Figure 21:
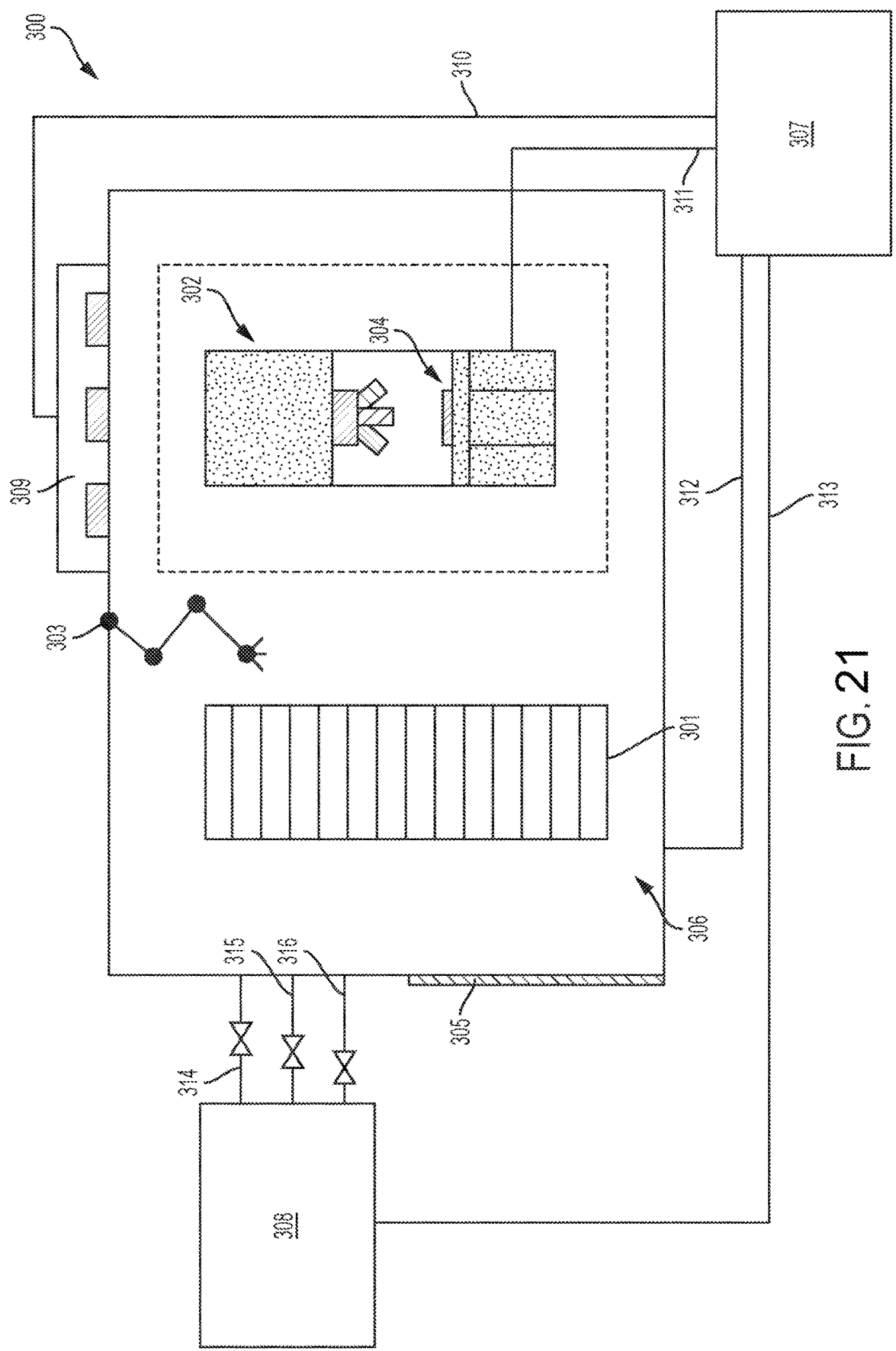
FIG. 21 is a schematic of an automated cell culture incubator having an integrated imaging system and an environmental control system.

FIG. 21 depicts another illustrative embodiment of a cell culture incubator (300) having a holographic or phase-contrast imager (302), a control and monitoring station (307) and an environmental control station (308). As above, the cell culture incubator includes an incubator cabinet having an internal chamber (306) for incubation of cells in one or more cell culture vessels, and the internal chamber is configured to hold one or more cell culture vessels at a storage location (301). The incubator cabinet includes an external door (305) that opens and closes to permit communication between an external environment and the internal chamber. The incubator cabinet includes a first imaging location (304) where cells can be imaged. Here again, cells can be monitored over time (e.g., during a long-term culture) using the holographic or phase-contrast imager (302) by transferring one or more cell culture vessels back and forth between the storage location (301) to the first imaging location (304) using the transfer device (303). The holographic or phase-contrast imager (302) can be used to acquire images of the cells. Image information from the holographic or phase-contrast imager (302) can be transferred to the external control and monitoring station (307) via a communication line (311).

A sensor panel (309) is provided which includes one or more sensors for measuring environmental conditions relevant to maintenance of cell growth, which may include temperature, CO2, O2, humidity or other relevant parameters. A sensor communication line (310) is provided to transfer information between the sensors and the control and monitoring station (307). The control and monitoring station includes a controller that may produce one or more control outputs to the environmental control station (308) in response to input from the sensor panel 309. For example, if the controller receives a signal from the sensor panel that one or more environmental parameters is outside a desired set point, the controller can send an appropriate signal to the environmental control station (308), in response to which the environment control station (308) can control operation of an appropriate fluid supply line (314-316) to introduce an appropriate gas or fluid or other medium into the internal chamber to restore the environmental conditions to a desired state.

In a more specific example, the controller may receive a signal from the sensor panel that CO2 levels are below a desired set point (e.g., below 5% CO2). In response to the signal, the controller can send an appropriate signal to the environmental control station (308), in response to which the environment control station (308) can control operation of a CO2 supply line (314). The CO2 supply line (314) can introduce CO.2 into the internal chamber to restore the CO2 to the desired set point. In another example, the controller may receive a signal from the sensor panel that humidity levels are below a desired set point (e.g., below 80% humidity). In response to the signal, the controller can send an appropriate signal to the environmental control station (308), in response to which the environment control station (308) can control operation of a water vapor supply line (315). The water vapor supply line can introduce water vapor into the internal chamber to restore the humidity to the desired set point. In another example, the controller may receive a signal from the sensor panel that incubator temperature is above or below a desired set point (e.g., above or below 37 degrees C.). In response to the signal, the controller can send an appropriate signal to incubator jacket heater via heater control line (312), in response to which the incubator jacket heater can be appropriately modulated to increase or decrease the temperature in the incubator to restore the temperature to the desired set point.

In some embodiments, the holographic or phase-contrast imager (302) can be used to acquire images of cells. Image information from the holographic or phase-contrast imager (302) can be transferred to the control and monitoring station (307) via a communication line (311). The control and monitoring station (307) can be fitted with a computer configured to process image information and produce appropriate control signals based on the processed image information. In this way, environmental conditions inside the chamber can be adjusted and controlled not only based on information from environmental sensors (e.g., CO2, humidity, or temperature sensors) but also from, or alternatively from, information regarding cell growth or health obtained from imaging cells within the automated incubator that is indicative of a need to alter the environmental conditions. For example, cells may exhibit characteristic changes that can be detected by imaging when the pH of a surrounding medium drops below a physiologically appropriate level which may indicate that CO2 levels in the chamber need to be adjusted. The characteristic changes can be detected by imaging, and the environmental control station (308) can operate to restore the conditions.

Figure 22:
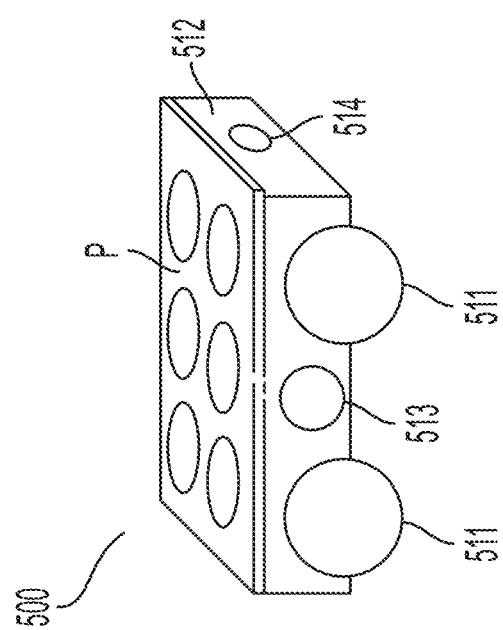
FIG. 22 is a drawing of an embodiment of a robotic transport for moving cell plates between stations.

In some embodiments the transport is robotic and has can be wheeled for moving cell media such as a plate between locations or stations. The robotic transport can have two or more wheels such as a four-wheel version 500 shown in FIG. 22. In some embodiments the plate P sits on the robotic transport and is moved between the storage station, the manipulation station, the imaging station and other stations that may be provided within the system. The wheels 511 can be wheels that permit movement in the x and y directions to steer the plate into position at a location. The body 512 of the transport includes in some embodiments the circuitry needed to guide the transport. While the transport 500 is shown in a car-like configuration, it is understood by those of skill in the art that other configurations are also possible.

In some embodiments the transport includes video sensors for sensing a path on the floor of the incubator, for sensing markings on a grid on the floor of the incubator, for sensing markings on the top of the incubator, for sensing obstacles in its path. In some embodiments, the transport circuitry prepares a map of the environment of the incubator and is able to determine its location be comparing a current snapshot of its surroundings or of the floor or ceiling markings to the ones in the map.

In some embodiments, the guidance circuitry for the transport can be in the incubator itself and the incubator can provide the signals to the motor controllers in the transport to move the transport from location to location.

Figure 23:
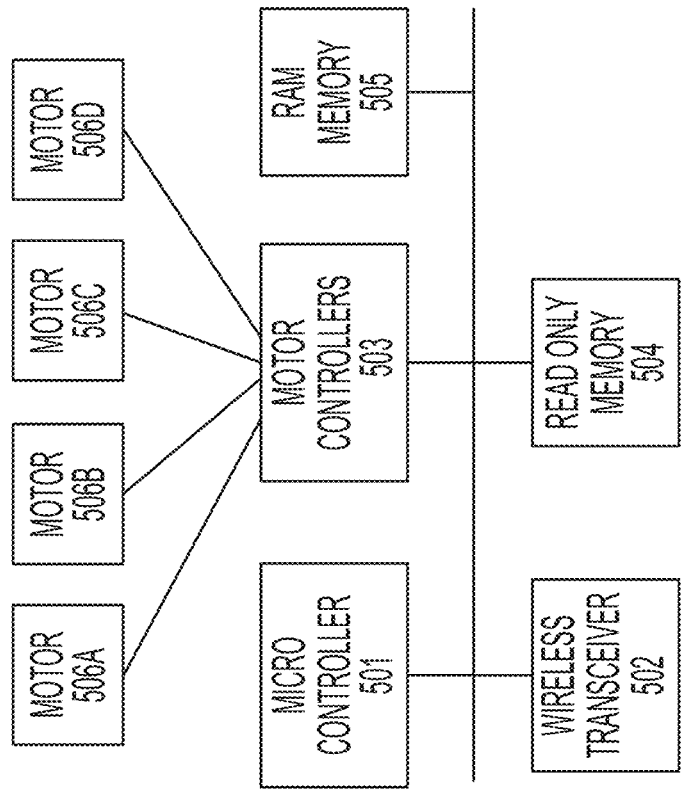
FIG. 23 is a block diagram of the circuitry in the robotic transport of FIG. 22.

The guidance circuitry of the transport 500 is shown by way of example in FIG. 23. Preferably each wheel has a motor 506A-506D for moving a wheel, although in other embodiments fewer motors can be used. The motors 506A-506D are controlled by motor controllers 503 under the control of a microcontroller 501 that works in conjunction with RAM 505 and ROM 504. The transport also has sensors and/or light emitters 512 and 513 as well as others that are not shown in the drawing. These sensors are video, acoustic, light or other sensors for aiding in the locating of the transport in the incubator. The light emitters are laser, infrared or ultraviolet light emitters for locating the transport in the incubator and guiding it.

Communications to the microcontroller 502 are preferably wireless and through a wireless transceiver 502. Communications can be by way of radio waves using Bluetooth, Wi-Fi, Zigbee, 5G cellular or by acoustical waves, light waves such as infrared or ultraviolet. The robotic transport is powered in some embodiments by rechargeable batteries in the body thereof and not shown. In some embodiments the rechargeable batteries can be recharged by charging coils in the floor of the incubator. In some embodiments the robotic transport is both powered and communicated with without wires that tether or limit the motion of the transport.

While a wheeled transport is shown, in some embodiments the transport can be a drone that can move in the X, Y and Z directions within the incubator. This would enable the transport to reach plates that is stacked in storage locations and bring them to another station in the incubator.

Figure 25:
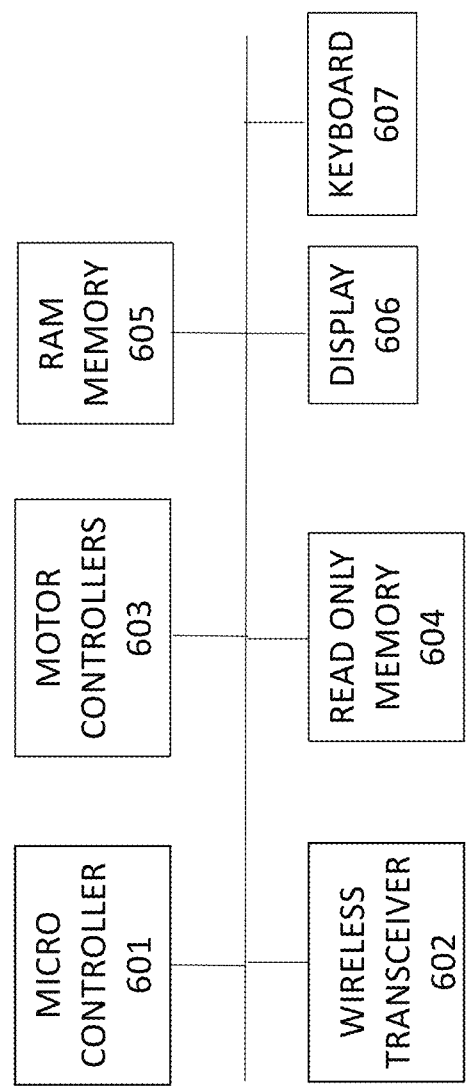
FIG. 25 is a block diagram of the master controller for an incubator and the robotic transport.

In some embodiments the robotic transport is controlled wirelessly by a master controller which can take the form of a laptop, desktop, or tablet computer and/or can be have the circuitry shown in FIG. 25. As shown the master controller has a microcontroller 601, RAM 605, ROM 604 and a wireless transceiver 602. The master controller also preferably has a display 606 and keyboard 607 for a user interface. The master controller has motor controllers for generating the signals for controlling the motors on the robot transport and these signals are sent wirelessly by transceiver 602. Communications can be by way of radio waves using Bluetooth, Wi-Fi, Zigbee, 5G cellular or by acoustical waves, light waves such as infrared or ultraviolet. Alternatively, the master controller and robotic transport can share the responsibilities for moving the transport form location to location, with some of the intelligence in the transport circuitry and some in the master controller.

Figure 26:
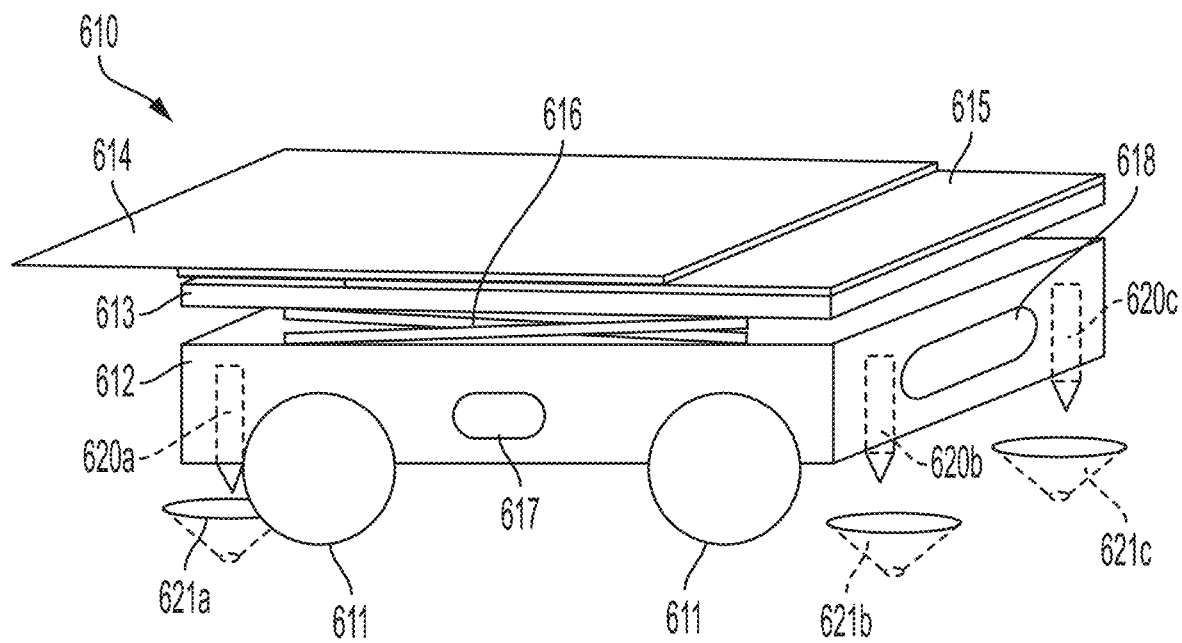
FIG. 26 is another embodiment of the robotic transport for moving cell plates between stations.

FIG. 26 shows another embodiment of a robotic transport 610. The body 612 of the transport has sensors and/or light emitters 617 and 618 and others not shown for guidance purposes. The body also houses the circuitry for the transport, for example the circuitry of FIG. 23. The body also carries wheels 611 which are preferably omni-wheels which allow movement in both the X and Y directions under the control of motors therein.

The top of the transport includes a mechanism for handling cell culture plates to move them from one station to another. There is a scissor mechanism 616 which raises first plate 613 up and down to provide the Z directions movement needed to place a cell culture plate in an imager or a manipulator. The rack and pinion mechanism connected between the second plate 615 and the spatula 614 allows for the spatula to move in the Y direction to aid in the removal and reinsertion of a cell culture plate in a station.

The transport also includes in some embodiments a mechanism for precisely positioning the transport at a station in the incubator. This mechanism includes conical depressions 621a-c (a fourth depression is not shown) which interact with feet 620a-c (a fourth foot is not shown). When the transport 610 is in its approximate position at a station with the feet 620 disposed above the depressions 621, the feet are lowered by a motor downwardly into the depressions. As the feet travel into the depressions, the feet contact the conical walls and are guided so that the pointed end of each foot sits in the bottom of the cone. This precisely positions the transport for the operations on the cell culture plate.

Figure 24:
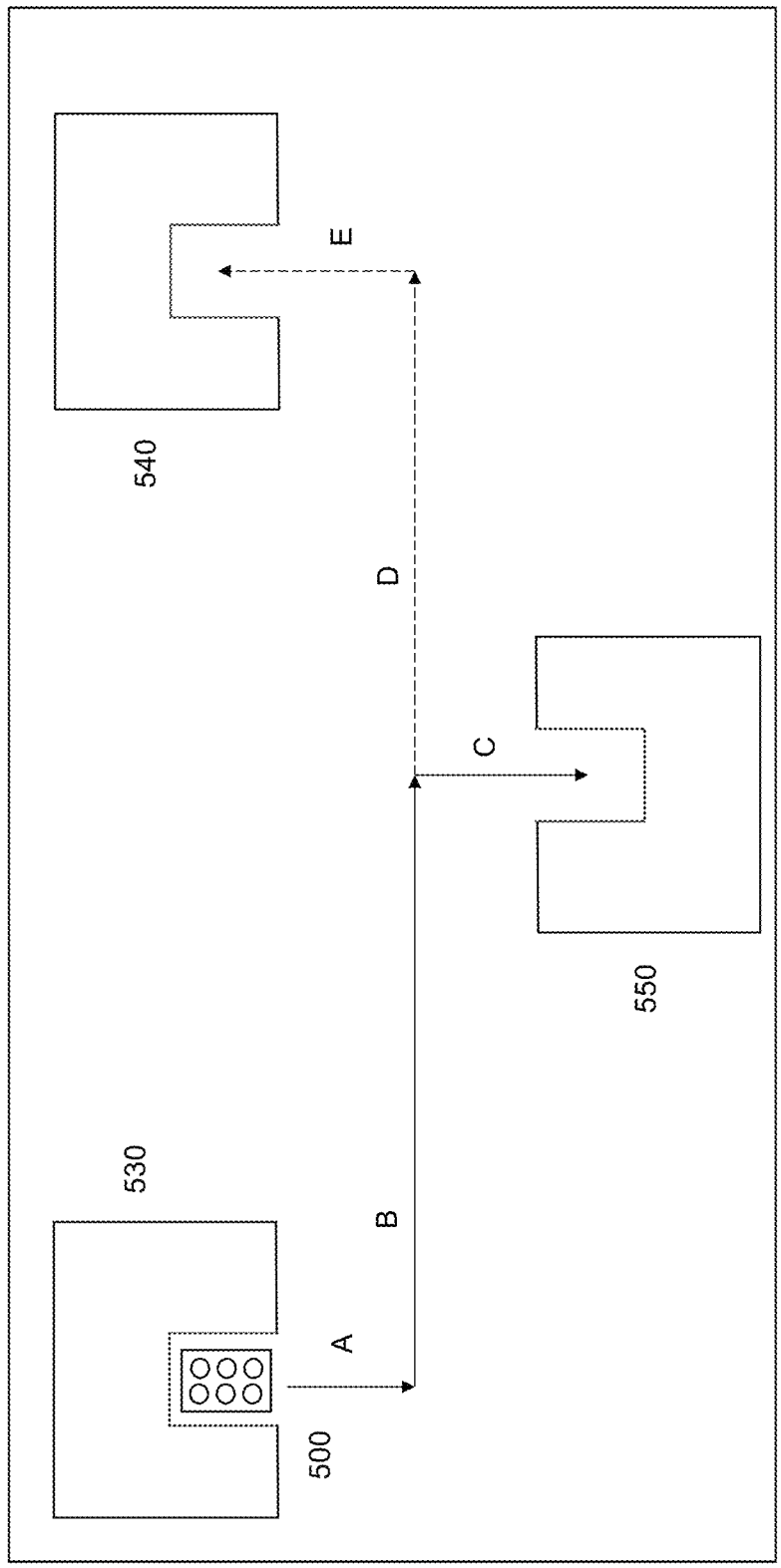
FIG. 24 is a schematic of paths taken by a transport between various stations.

FIG. 24 shows some examples of the paths that the transport 500 can take within the incubator to move between stations. The transport 500 starts at storage station 530 which can hold one or more plates in different manners. For example, the storage station can have a carousel of plates that is rotated until the desired plate is in position to place on the transport. Alternatively, the storage station can have a vertical storage holder that moves plates up and down in the z direction to put a desired plate in position for transport. In some embodiments the storage station can have a combination of a carousel and elevator to store plates. In some embodiments the storage station can have an elevator for lifting the transport in the Z direction to receive or return a cell culture plate.

The transport 500 with a plate is moved along path A and then path B. If the next position for the plate is manipulation station 55, then the plate is moved along path C to the position within the manipulation station 55. If on the other hand, the plate is to be moved to imaging station 540 first, then the transport is moved along paths D and E into position in the imaging station 540.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A cell incubator system comprising:
   a. a housing comprising an internal chamber having a controlled temperature and gas mixture therein appropriate for the growth of particular cells for incubation of the particular cells in a well of one or more cell culture vessels in the internal chamber;
   b. a plurality of cell operation stations in the internal chamber, wherein the stations receive the one or more cell culture vessels and wherein the cell operations stations perform operations on cells in the one or more cell culture vessels;
   c. a trackless robotic transport for moving plates from a first station to a second station, wherein the trackless robotic transport has visual sensors for sensing a path on a surface of the internal chamber and wirelessly transmitting signals representative of the path; and
   d. a microcontroller configured to guide the robotic transport from the first station to the second station, wherein the microcontroller and the robotic transport wirelessly receive the signals from the visual sensors to direct the robotic transport from the first station to the second station.

2. The cell incubator system according to claim 1, wherein at least one of the first and second stations is an imaging station.

3. The cell incubator system according to claim 1, wherein at least one of the first and second stations is a cell manipulation station.

4. The cell incubator system according to claim 1, wherein at least one of the first and second stations is a pipetting station.

5. The cell incubator system according to claim 1, wherein at least one of the first and second stations is a plate storage station.

6. The cell incubator system of claim 1, wherein the surface is a lower surface of the internal chamber that has sensing markings on a grid and wherein the sensors sense the grid markings.

7. The cell incubator system of claim 1, wherein the surface is an upper surface of the internal chamber that has sensing markings on a grid and wherein the sensors sense the grid markings.

8. The cell incubator system of claim 1, wherein the microcontroller maps the surface of the internal chamber using the sensors and determines a location of the robotic transport by comparing a current view of the transport surroundings and the map.

9. The cell incubator system of claim 1, wherein the robotic transport is powered by rechargeable batteries and wherein the internal chamber has charging coils in a lower surface for charging the batteries.

10. The cell incubator system of claim 1, wherein the robotic transport is a drone moveable in X, Y, and Z directions in the internal chamber.

11. The cell incubator system of claim 1, wherein the robotic transport has a scissor mechanism for moving a cell culture vessel up and down.

* * * * *